US012291527B2

(12) United States Patent
De Fatima et al.

(10) Patent No.: US 12,291,527 B2
(45) Date of Patent: May 6, 2025

(54) MOLECULES THAT STIMULATE THE IMMUNE SYSTEM FOR TREATMENT OF DRUG ADDICTION, METHODS OF SYNTHESIS, ANTIDRUG VACCINE AND USES

(71) Applicants: UNIVERSIDADE FEDERAL DE MINAS GERAIS, Belo Horizonte (BR); FUNDACAO DE AMPARO A PESQUISA DO ESTADO DE MINAS GERAIS—FAPEMIG, Belo Horizonte (BR)

(72) Inventors: Angelo De Fatima, Belo Horizonte (BR); Frederico Duarte Garcia, Belo Horizonte (BR); Simone Odilia Antunes Fernandes, Belo Horizonte (BR); Valbert Nascimento Cardoso, Belo Horizonte (BR); Adriana Martins Godin, Belo Horizonte (BR); Angelica Faleiros Da Silva Maia, Belo Horizonte (BR); Leonardo Da Silva Neto, Belo Horizonte (BR); Maila De Castro Lourenco Das Neve, Belo Horizonte (BR); Paulo Sergio De Almeida Augusto, Betim (BR)

(73) Assignees: UNIVERSIDADE FEDERAL DE MINAS GERAIS, Belo Horizonte (BR); FUNDACAO DE AMPARO A PESQUISA DO ESTADO DE MINAS GERAIS—FAPEMIG, Belo Horizonte (BR)

( * ) Notice: Subject to any disclaimer, the term of this patent is extended or adjusted under 35 U.S.C. 154(b) by 658 days.

(21) Appl. No.: 16/633,696

(22) PCT Filed: Jul. 20, 2018

(86) PCT No.: PCT/IB2018/055440
§ 371 (c)(1),
(2) Date: May 12, 2020

(87) PCT Pub. No.: WO2019/021140
PCT Pub. Date: Jan. 31, 2019

(65) Prior Publication Data
US 2020/0385376 A1  Dec. 10, 2020

(30) Foreign Application Priority Data
Jul. 25, 2017  (BR) .......................... 1020170159558

(51) Int. Cl.
*C07D 451/12* (2006.01)
*A61K 39/385* (2006.01)
*A61P 25/36* (2006.01)
*A61K 39/00* (2006.01)
*C07C 69/732* (2006.01)

(52) U.S. Cl.
CPC .......... *C07D 451/12* (2013.01); *A61K 39/385* (2013.01); *A61P 25/36* (2018.01); *A61K 2039/60* (2013.01); *C07C 69/732* (2013.01)

(58) Field of Classification Search
CPC .................................................. C07D 451/12
See application file for complete search history.

(56) References Cited

U.S. PATENT DOCUMENTS

| 5,233,042 A | 8/1993 | Buechler |
| 5,463,028 A | 10/1995 | Landry et al. |
| 6,383,490 B1 | 5/2002 | Wirsching et al. |
| 2009/0105352 A1 | 4/2009 | Bezwada et al. |
| 2010/0314847 A1 | 12/2010 | Sonnendorfer et al. |

FOREIGN PATENT DOCUMENTS

| WO | WO-9721451 A1 * | 6/1997 | ............. A61K 31/46 |
| WO | 2009149252 A1 | 12/2009 | |
| WO | 2011028875 A1 | 3/2011 | |
| WO | 2011116189 A1 | 9/2011 | |
| WO | WO-2016030635 A1 * | 3/2016 | ............. A61K 39/12 |

OTHER PUBLICATIONS

Bonese et al., "Changes in heroin self-administration by a rhesus monkey after morphine immunization", Nature. 1974, vol. 252, pp. 708-710.
Cai et al., "Probing active cocaine vaccination performance through catalytic and noncatalytic hapten design", J. Med. Chem, 2013, vol. 56, pp. 3701-3709.
Carrera et al., "Suppression of psychoactive effects of cocaine by active immunization", Nature, 1995, vol. 378, pp. 727-730.
Du et al., "Spectrofluorimetric study on the inclusion behavior of p-sulfonated calix [4, 6, 8] arene with cocaine hydrochloride", Analytical Chemistry and Indian Journal ACAIJ, 2015, vol. 15, No. 8, pp. 281-289.
Dudic et al., "R.A general synthesis of water soluble upper rim calix[n]arene guanidinium derivatives which bind to plasmid DNA", Tetrahedron, 2004, vol. 60, pp. 11613-11618.
Fetissov, "Neuropeptide autoantibodies assay", Methods Mol Biol, 2011, vol. 789, pp. 295-302.

(Continued)

*Primary Examiner* — Matthew P Coughlin
(74) *Attorney, Agent, or Firm* — LUCAS & MERCANTI, LLP

(57) ABSTRACT

This technology relates to immune system stimulating molecules to be used in the treatment of drug addiction and abuse and their synthesis processes. These molecules have a calixarene chemical structure, preferably calix[4]arene and/or calix[8]arene, coupled to an hapten analogous to cocaine, preferably GNE and/or GNC. An anti-drug vaccine, specifically anti-cocaine, is also described using such molecules. The anti-drug vaccine can be also used to prevent fetal exposure to drugs in pregnant women who use drugs and do not wish or cannot stop their use during pregnancy.

8 Claims, 28 Drawing Sheets

(56) References Cited

OTHER PUBLICATIONS

Findlay, "The three-dimensional structure of the Cocaines: Part I. Cocaine and Pseudococaine", J. Am. Chem. Soc., 1954, vol. 76, No. 11, pp. 2855-2862.

Geraci et al., "Calix[4]arene decorated with four Tn Antigen Glycomimetic Units and P3CS Immunoadjuvant: synthesis, characterization, and Anticancer Immunological Evaluation", Bioconjugate Chem, 2008, vol. 19, No. 3, pp. 751-758.

"Global Illicit Drug Trends", United Nations Office on Drugs and Crime, UNODC, 2003,—ISBN 92-1-148156-2, pp. 1-351.

Gutsche et al., "The synthesis, Characterization, and Properties of the Calixarenes from p-tert-butylphenol.", J. Am. Chem. Soc, 1981, vol. 103, No. 13, pp. 3782-3792.

Gutsche et al., "p-tert-butylcalix[4]arene", Org. Synth, 1990, vol. 68, pp. 234-236.

Haney et al., "Cocaine-specific antibodies blunt the subjective effects of smoked cocaine in humans", Biol Psychiatry. 2010, vol. 67, No. 1, pp. 59-65.

Kenis et al., "Supramolecular materials: molecular packing of tetranitrotetrapropoxycalix[4]arene in highly stable films with second-order nonlinear optical properties", Chem. Eur. J., 1998, vol. 4, No. 7, pp. 1225-1234.

Kosten et al., "Human therapeutic cocaine vaccine: safety and immunogenicity", Vaccine 20, 2002, pp. 1196-1204.

Martell et al. "Cocaine Vaccine for the Treatment of Cocaine Dependence in Methadone-Maintained Patients, A Randomized, Double-Blind, Placebo-Controlled Efficacy Trial", Arch Gen Psychiatry, 2009, vol. 66, No. 10, pp. 1116-1123.

Martell et al., "Vaccine pharmacotherapy for the treatment of cocaine dependence", Biol Psychiatry, 2005, vol. 58, pp. 158-164.

Meijler et al., "Fluorescent cocaine probes: a tool for the selection and engineering of therapeutic antibodies", J. Am. Chem. Soc., 2005, vol. 127, pp. 2477-2484.

Podoprygorina et al., "Supramolecular structures formed by calix[8]arene derivatives", Org. Lett., 2003, vol. 5, No. 26, p. 5071-5074.

Sakurai et al., "Design and synthesis of a cocaine-diamide hapten for vaccine development", Tetrahedron Lett., 1996, vol. 37, No. 31, pp. 5479-5482.

Sansone et al., "DNA Condensation and Cell transfection properties of Guanidinium Calixarenes: Dependence on macrocycle lipophilicity, size, and conformation", J. Am. Chem. Soc., 2006, vol. 128, pp. 14528-14536.

Verboom et al., "Ipso Nitration of p-tert-Butylcalix[4]arenes", J. Org. Chem., 1992, vol. 57, pp. 1313-1316.

Wee et al., "Novel Cocaine Vaccine Linked to a Disrupted Adenovirus Gene Transfer Vector Blocks Cocaine Psychostimulant and Reinforcing Effects", Neuropsychopharmacology, 2012, vol. 37, pp. 1083-1091.

Yi et al., "Synthesis of p-terc-butylcalix[8]arene ether derivatives", Indian Journal of Chemistry, 2008, vol. 47B, pp. 1435-1437.

International Search Report and Written Opinion for Corresponding International Application No. PCT/IB2018/055440 (11 Pages) (Nov. 29, 2018).

\* cited by examiner

MOLECULES THAT STIMULATE THE IMMUNE SYSTEM FOR TREATMENT OF DRUG ADDICTION, METHODS OF SYNTHESIS, ANTIDRUG VACCINE AND USES

CROSS REFERENCE TO RELATED APPLICATION

This Application is a 371 of PCT/IB2018/055440 filed on Jul. 20, 2018 which, in turn, claimed the priority of Brazilian Patent Application No. BR 10 2017 015955 8 filed on Jul. 25, 2017.

This technology relates to immune system stimulating molecules to be used in the treatment of drug addiction and abuse and their synthesis processes. These molecules comprise a calixarene chemical structure, preferably calix[4]arene and/or calix[8]arene, coupled to a hapten analogous to cocaine, preferably GNE and/or GNC. An anti-drug vaccine, specifically anti-cocaine, is also described using such molecules. The anti-drug vaccine can also be used to prevent fetal exposure to drugs in pregnant women who use drugs and do not wish or cannot stop their use during pregnancy.

Cocaine and crack addiction and use are important causes of morbidity and mortality worldwide, being considered a real public health problem that affects up to 1% of the world's population. Currently, the pharmacological treatments available for the rehabilitation of cocaine drug addicts are based on the use of agonist drugs and neurotransmitter antagonists, psychotherapies, and the use of psychosocial rehabilitation techniques. Despite the efforts, the efficacy rate is still less than 45% of cases treated and the lack of specific medicaments is still a significant limiter (Global Illicit Drug Trends—United Nations Office on Drugs and Crime, UNODC 2003-ISBN 92-1-148156-2).

In this context, other pharmacological strategies have been studied for the treatment of substance abuse disorders, such as addictions. Many drug users have anti-drug antibodies, i.e., antibodies that bind to drugs, in their bloodstream, even without a specific immunological stimulation for producing these antibodies (Martell et al., Vaccine pharmacotherapy for the treatment of cocaine dependence. Biol Psychiatry 58(2): 158-164; 2005). These anti-drug antibodies can bind to the drug and prevent their pharmacological action (Kosten et al., Human therapeutic cocaine vaccine: safety and immunogenicity. Vaccine 20(7-8): 1196-1204; 2002). Besides the chelating effect, that is, of blocking the action of the drug in specific receptors in the bloodstream, anti-drug antibodies, when linked to the drug, greatly increase its molecular mass. This phenomenon prevents the passage of the drug through the blood-brain barrier and thereby its entry into the central nervous system. Thus, the drug does not act in its binding sites and does not cause its effect. It is believed that the lack of a "pleasant" psychotropic effect causes the user to decrease or abandon the use of the drug, interrupting the cycle that maintains chemical dependence (Haney et al., Cocaine-specific antibodies blunt the subjective effects of smoked cocaine in humans. Biol Psychiatry 67(1): 59-65; 2010).

Since 1974, other research groups have used immunization strategies for the production of substances capable of producing anti-drug antibodies (Bonese et al. Changes in heroin self-administration by a rhesus monkey after morphine immunization. Nature. 1974; 252:708-710). The use of various immunization strategies is necessary, since the chemical structures of psychotropic drugs are, by essence, molecules of low molecular weight and, therefore, low inductors of immune response against them, that is, low immunogenic.

The strategies already used to make psychotropic drugs immunogenic involve, for the most part, the coupling of the psychotropic drug molecule to a protein with high molecular weight, such as albumin, hemocyanins, or bacterial and viral proteins. In addition, the use of modulating substances of the immune system, known as adjuvants, is associated. To date, the described anti-drug vaccines induce the production of anti-drug antibodies, but the immune response does not produce antibodies in sufficient amount to chelate most of the drug in the bloodstream in approximately 60% of immunized individuals. Even with this limitation, preclinical and clinical phase I and II studies of vaccines for the treatment of cocaine, heroin, nicotine and amphetamines dependence demonstrated a strong potential for this type of treatment for chemical addictions (Kosten et al. 2002, Martell et al. 2005, Haney et al. 2010).

In order to conjugate the chemical structure of cocaine to the structure of a protein, it must be converted into a derivative called hapten. Some cocaine-like haptens have been already described and prepared, such as succinil norcocaine (CNS), GNC and also GNE. Isolated, haptens are not able to induce an immune response because they have a low molecular mass and, therefore, to become immunogenic, they are conjugated to protein structures. Prepared in 2013 by Cai et al. (Cai, X.; Whitfield, T.; Hixon, M. S.; Grant, Y.; Koob, G. F.; Janda, K. D. Probing active cocaine vaccination performance through catalytic and noncatalytic hapten design. J. Med. Chem. 2013, 56, p.3701-3709), GNE hapten is an amide derivative of cocaine that has been conjugated to the structure of serotype 5 adenovirus capside proteins, and called dAd5GNE. Studies reported by Wee et al. have pointed out that rats immunized with dAd5GNE produced high IgG anticocaine titers for up to 20 weeks (Wee, S.; Hicks, M. J.; De, B. P.; Rosenberg, J. B.; Moreno, A. Y.; Kaminsky, S. M.; Janda, K. D.; Crystal, R. G.; Koob, G. F. Novel Cocaine Vaccine Linked to a Disrupted Adenovirus Gene Transfer Vector Blocks Cocaine Psychostimulant and Reinforcing Effects. Neuropsychopharmacology 2012, 37, p.1083-1091). On the other hand, the GNC hapten is an ester derivative of cocaine, prepared in 1995 by Carrera et al. (Carrera, M. R. A.; Ashley, J. A.; Parsons, L. H.; Wirsching, P.; Koob, G. F.; Janda, K. D. Suppression of psychoactive effects of cocaine by active immunization. Nature 1995, 378, p.727-730). In this work, GNC hapten was conjugated to the KLH (Keyhole limpet hemocyanin) protein of mollusc *Megathura crenulata*, and designated (KLH-GNC). Among the main results, the authors observed that rats pre-immunized with the KLH-GNC conjugate presented behavioral changes and suppression in locomotor activity when administered with cocaine.

The following are among the current limitations for the development of an anti-drug vaccine: (1) low immunogenicity; (2) the risk of producing cross-immune reactions between hapten carrier proteins and thereby the development of autoimmune diseases; (3) the nonspecificity of immunogenous molecules and thereby the production of ineffective antibodies in chelating the target drug; (4) the instability of molecules, since they are proteins that can be degraded by temperature differences and exposure to ultraviolet rays.

For example, the anti-cocaine vaccine called TA-CD, which consists of succinyl norcocaine (SNC) combined with cholera toxin subunit B and the adjuvant aluminum hydroxide gel, demonstrated, in clinical trials, a variation in the concentration of produced antibodies. Only patients with high antibody titers have become abstinent (Martell et al. Cocaine Vaccine for the Treatment of Cocaine Dependence in Methadone-Maintained Patients: A Randomized, Double-Blind, Placebo-Controlled Efficacy Trial. Arch Gen Psychiatry. 2009; 66:1116-1123).

The patent document U.S. Ser. No. 19/910,808515, of Dec. 16, 1991, entitled "Cocaine derivatives", describes the synthesis of substances derived from cocaine that can be conjugated to antigenic proteins for the production of antibodies for immunological assays, indicating the possibility of producing antibodies from the cocaine molecule.

Patent document U.S. Ser. No. 19/920,862801, of Apr. 3, 1992, entitled "Reagents for generating a polyclonal hydrolytic antibody response against cocaine and the monoclonal hydrolytic antibodies against cocaine derived through these reagents", describes a substance comprising a methyl ecgonin group linked to a phenylophosphoric group that is analogous to an intermediate of the transitional state of hydrolysis of the benzoyl ester group of cocaine. It also describes these analogues linked to carrier proteins, capable of producing anti-cocaine antibodies.

The patent document U.S. Ser. No. 19/957,2849 of Dec. 14, 1995, entitled "Anti-cocaine vaccine", describes an anti-cocaine vaccine comprising the conjugation of an hapten to a carrier protein capable of producing an immune response that reduces the psychoactive effect of cocaine.

Other strategies for antibody production have been already described, as in patent document US20100314847 of Mar. 17, 2010, entitled "Disrupted adenovirus-based vaccine against drugs of abuse", which describes the use of a viral vector comprising a sequence of nucleic acid encoding for an anti-cocaine antibody.

In the article published by Quian Du et al. (Du Q, Chen C P, Du L M; "Spectrofluorimetric study on the inclusion behavior of p-sulfonated calix [4, 6, 8]arene with cocaine hydrochloride", Analytical Chemistry and Indian Journal ACAIJ, 15 (8) 2015, pages 281-289), the authors describe the use of calix[n]arene p-sulphonic acids (n=4, 6 or 8) as guest molecules for cocaine, aiming at establishing an analytical method for cocaine determination in samples. For this, Du et al. conducted several studies of fluorescence and nuclear magnetic resonance (NMR) on the stability of the supramolecular complex formed between calix[n]arene p-sulphonic acids (n=4, 6 or 8) and cocaine. The purpose of these authors did not include or cite the use of this supramolecular complex as a potential immunogen for cocaine.

In the state of the art, no technology similar to that described in the present invention was found, which proposes the use of non-protein molecules, calix[n]arene p-sulphonic acids (n=4, 6 or 8), as hapten carrier structural platforms in the synthesis of vaccines for treating abuse substance addictions.

The present invention proposes substances with a well-defined structure, that can be easily obtained, purified and characterized; easy to escalate; having considerable stability at high temperatures and light; and with high molecular weight g mol$^{-1}$, a fundamental factor in promoting the induction of an immune response. Moreover, in view that they are not protein molecules, they have a lower potential to cross-immune reactions. This causes them to have less risk for the development of autoimmune diseases or interference in the immunized organism.

The molecules proposed in the present invention were able to actively immunize patients treated with them. This immunization causes the immunized organism to produce specific antibodies against the drug. These antibodies are able to bind to the drug in the bloodstream, preventing its pharmacological action in the central nervous system and peripheral organs.

DETAILED DESCRIPTION OF THE TECHNOLOGY

This technology relates to immune system stimulating molecules to be used in the treatment of drug addiction and abuse and their synthesis processes. These molecules comprise a calixarene chemical structure, preferably calix[4]arene and/or calix[8]arene, coupled to an hapten analogous to cocaine, preferably GNE and/or GNC. It further describes an anti-drug vaccine, specifically anti-cocaine, using such molecules. The anti-drug vaccine can be also used to prevent fetal exposure to drugs in pregnant women who use drugs and do not wish or cannot stop their use during pregnancy.

Figure 1:
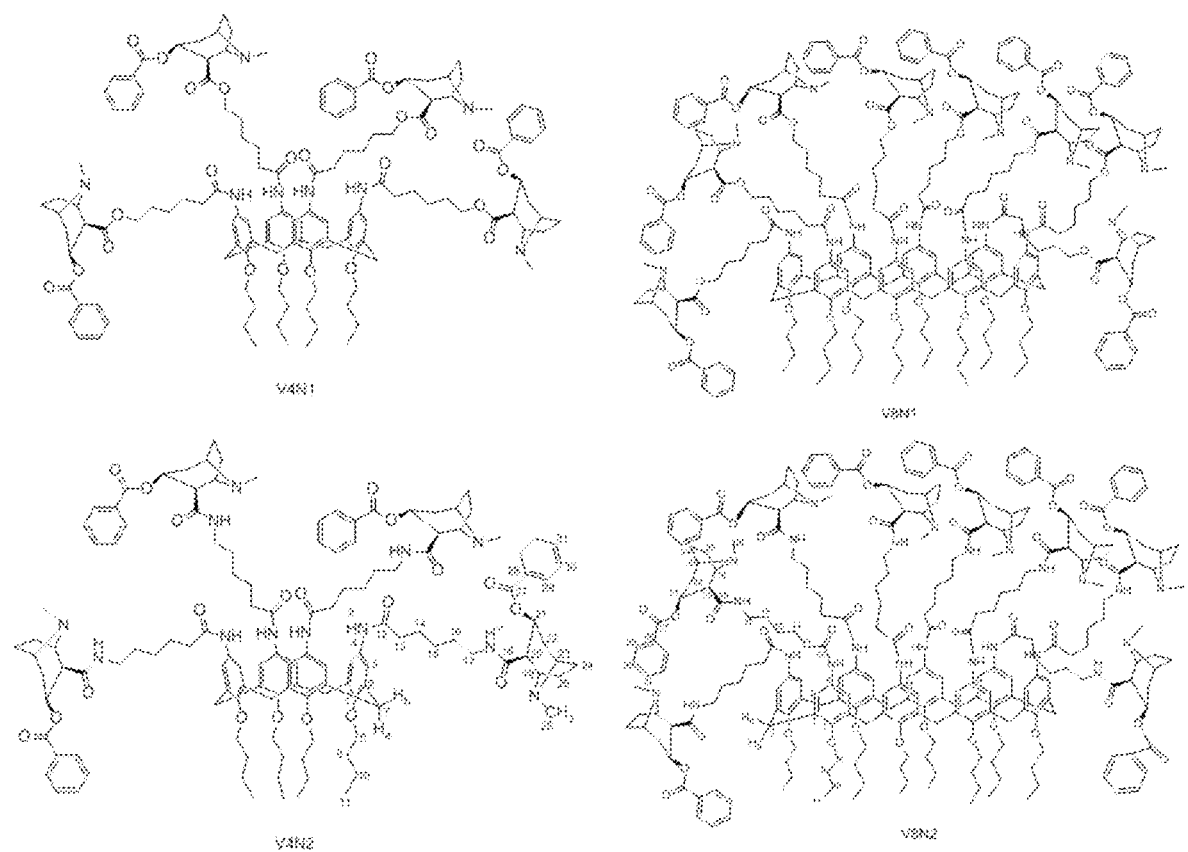
FIG. 1 presents the structures of the substances V8N1, V8N2, V4N1 and V4N2.

More specifically, the present invention comprises molecules formed by coupling calixarenes to hapten GNE (6-((1R,2R,3S,5S)-3-(benzoyloxy)-8-methyl-8-azabicyclo[3.2.1]octane-2-carboxamido)-hexanoic acid) and/or to hapten GNC (6-(((1R,2R,3S,5S)-3-(benzoyloxy)-8-methyl-8-azabicyclo[3.2.1]octane-2-carbonyl)oxy)-hexanoic acid), preferably molecules formed by calix[4]arene coupling to hapten GNC or GNE, herein referred to as V4N1 and V4N2, respectively; and molecules formed by calix[8]arene coupling to hapten GNC or GNE, referred to as V8N1 and V8N2, respectively; as represented in FIG. 1.

Figure 2:
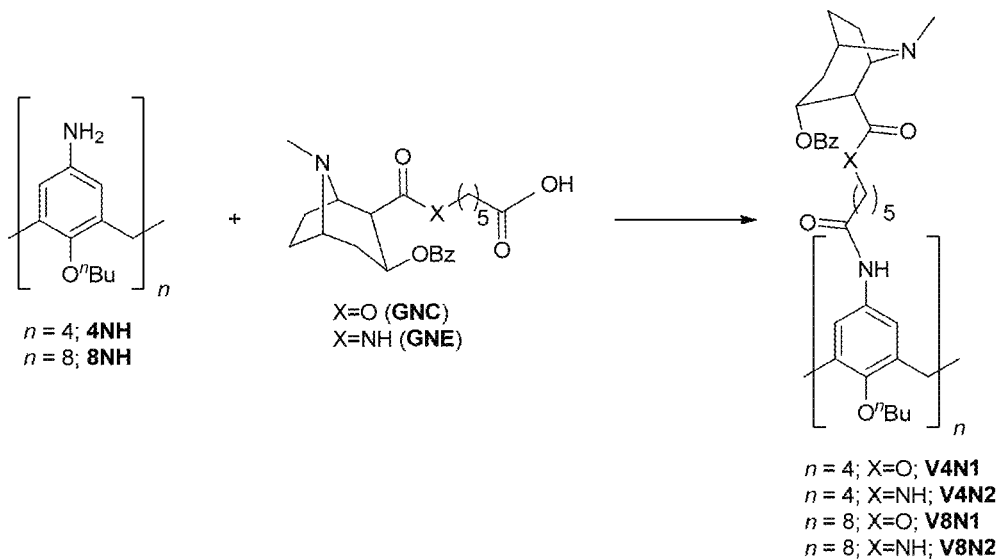
FIG. 2 presents the coupling reaction scheme between GNC and GNE haptens to calixarenes 4NH and 8NH.
Figure 4:
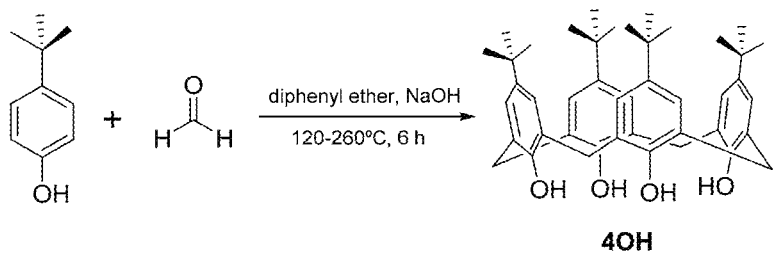
FIG. 4 presents the reaction scheme of obtaining the substance 4OH.
Figure 6:
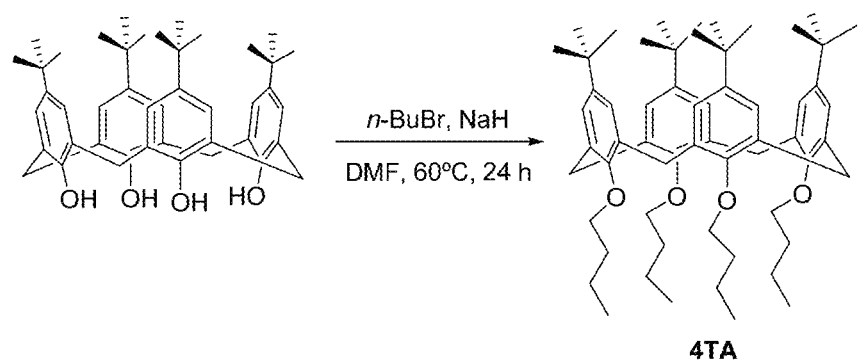
FIG. 6 presents the reaction scheme of obtaining the substance 4TA.
Figure 8:
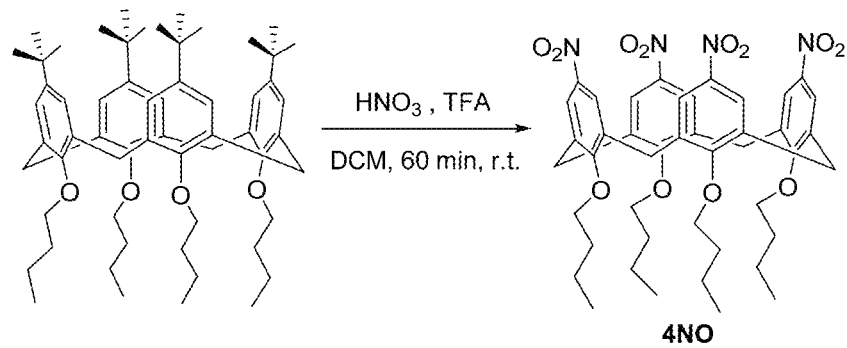
FIG. 8 presents the reaction scheme for obtaining structure 4NO.
Figure 10:
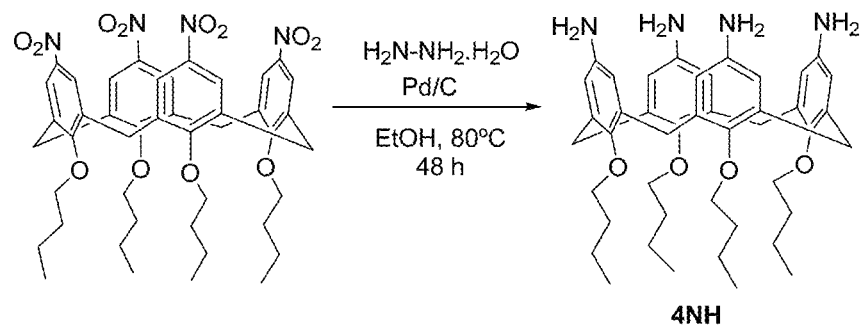
FIG. 10 presents the reaction scheme for obtaining substance 4NH.

The process proposed for the synthesis of the immune system stimulating molecules V4N1 and V4N2 comprises the following steps:

a. Obtainment of substance 4OH, as illustrated in FIG. 4:
  i. Prepare a mixture of p-tert-butylphenol (0.141 to 14.100 g mL$^{-1}$) and sodium hydroxide (0.002 to 0.200 g mL$^{-1}$) in formaldehyde;
  ii. Heat to 110-120° C. and stir the system until formation of a yellow solid;
  iii. Add diphenyl ether to make a solution 0.3 to 0.7, w/v (from p-tert-butylphenol in relation to diphenyl ether). Stir and maintain under reflux conditions for 150 to 210 minutes;
  iv. Cool to room temperature, add of ethyl acetate (180 to 220% v/v), stir for 90 to 150 minutes and rest;
  v. Filter and wash the solid using successively ethyl acetate, acetic acid and distilled water;
b. Obtainment of substance 4TA, as illustrated in FIG. 6:
  i. Prepare a solution of the solid obtained in step "a" (0.003 to 0.300 g·mL$^{-1}$) and sodium hydride (0.001 to 0.100 g mL$^{-1}$) in dimethylformamide;
  ii. Stir for 50 to 70 minutes and add n-bromobutane (0.008 to 0.800 g mL$^{-1}$);
  iii. Heat up to 55 to 65° C. and stir for 22 to 26 hours;
  iv. Cool at room temperature;
  v. Add water (20 to 30% v/v) and filter the obtained solid;
c. Obtainment of substance 4NO, as illustrated in FIG. 8:
  i. Prepare a solution of the solid obtained in step "b" (0.87 to 87.0% w/v) together with trifluoroacetic acid (1.2 to 120.0% v/v) and steaming nitric acid (1.0 to 100.0% v/v) in dichloromethane;
  ii. Stir for 50 to 70 minutes and pour in distilled water (0.145 to 14.5% w/v);
  iii. Perform the extraction of the product obtained in "ii" using dichloromethane;
  iv. Wash with saturated sodium bicarbonate solution and, later, with saturated sodium chloride solution;
  v. Dry, filter and evaporate the organic phase using preferably distillation at reduced pressure;
  vi. Recrystallize the solid obtained in "v" using chloroform and methanol (2 to 8% w/v).
  vii. Filter the white solid obtained;
d. Obtainment of substance 4NH, as illustrated in FIG. 10:
  i. Prepare a solution of the solid obtained in step "c" (0.2 to 20.0% w/v) together with hydrazine (2.0 to 200.0% v/v) and palladium (catalytic quantity) in ethanol;
  ii. Heat up to 80° C. and stir for 48 hours;
  iii. Remove the catalyst by filtration;
  iv. Evaporate the organic phase and wash the solid obtained with distilled water;
e. Preparation of immunogens V4N1 and V4N2 by the coupling reaction between calixarene 4NH and hapten GNC or GNE, respectively, as illustrated in FIG. 2:
  i. Prepare a mixture of hapten (0.012 to 1,200 g mL$^1$), being hapten GNE (for synthesis of V4N2) and hapten GNC (for synthesis of V4N1), together with diisopropylethylamine (0.004 to 0.400 g mL$^{-1}$) and (benzotriazol-1-il-oxy)-tris(pyrrolidine)-phosphonium hexafluorophosphate (0.02 to 2.00 g mL$^{-1}$) in anhydrous dichloromethane, under inert gas atmosphere, and stir for 30 to 50 minutes at room temperature;
  ii. Prepare a solution of the solid obtained in step "d" (0.003 to 0.300 g mL$^{-1}$) in anhydrous dichloromethane, under inert gas atmosphere and stir for 5 to 15 minutes at room temperature;
  iii. Transfer the solution obtained in step "ii" dropwise, under inert gas atmosphere, to the vessel containing the mixture obtained in step "i", to a final concentration of 0.039 to 3.9 g mL$^{-1}$ and stir at room temperature for 22 to 28 hours;
  iv. Adding dichloromethane and wash with saturated sodium bicarbonate solution and subsequently with distilled water;
  v. Dry, filter and evaporate the organic phase, preferably by distillation. Purify the product using preferably column chromatography.

Figure 28:
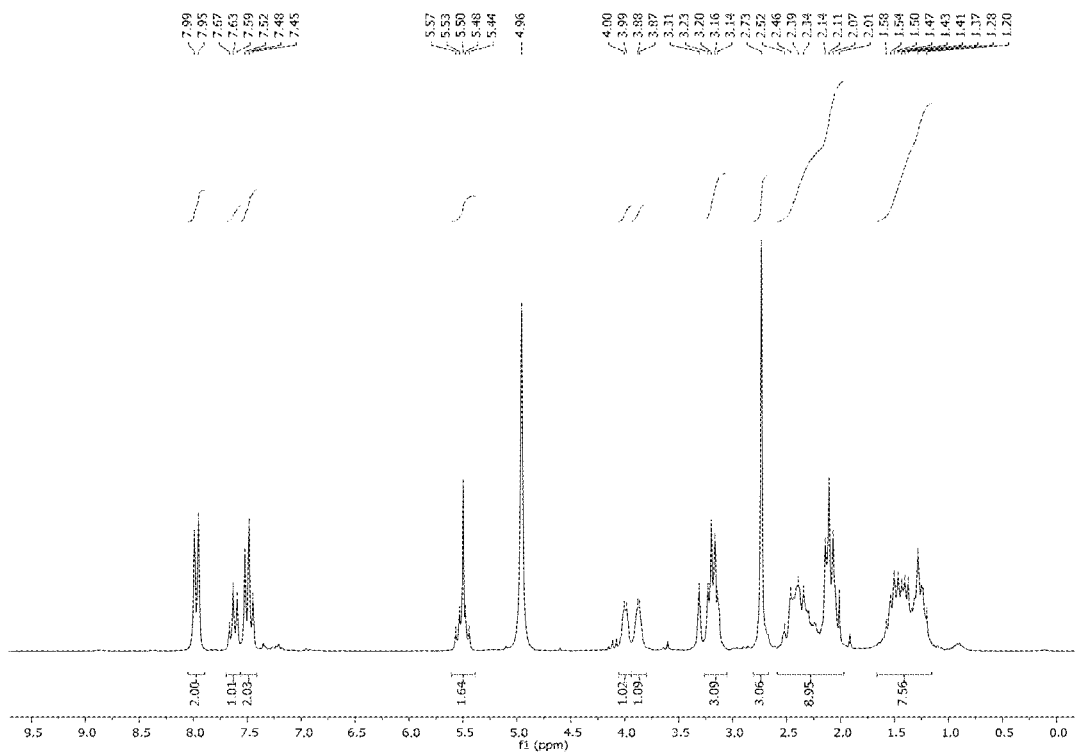
FIG. 28 presents the hydrogen nuclear magnetic resonance spectrum [$^1$H NMR; 200 MHz, CD$_3$OD] obtained for substance GNE.
Figure 31:
FIG. 31 presents the infrared spectrum obtained for substance V4N2.
Figure 32:
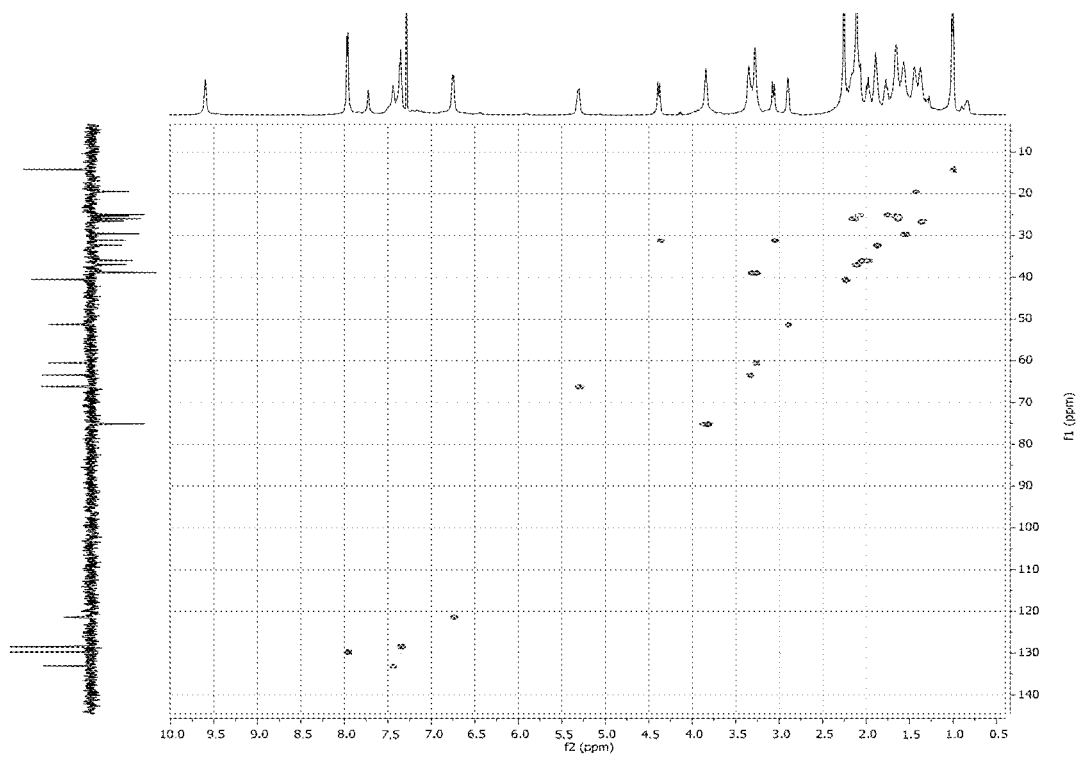
FIG. 32 presents the HSQC contour map obtained for substance V4N2.
Figure 34:
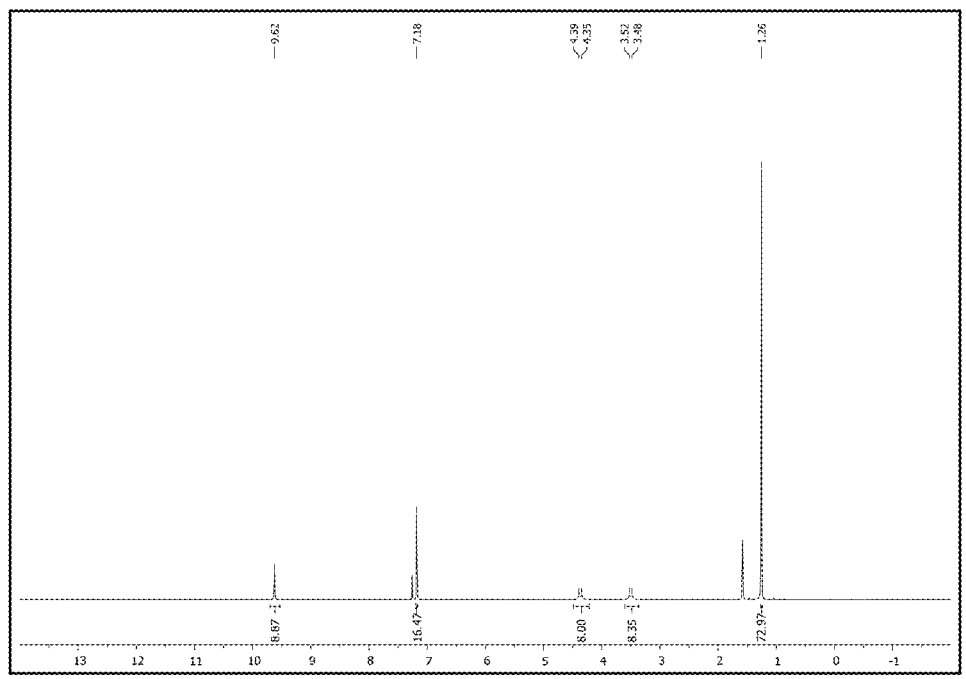
FIG. 34 presents the hydrogen nuclear magnetic resonance spectrum [$^1$H NMR; 200 MHz, CDCl$_3$] obtained for substance 8OH.

The process proposed for the synthesis of the immune system stimulating molecules V8N1 and V8N2 comprises the following steps:

a. Obtainment of substance 8OH, by cyclocondensation reaction of p-tert-butylphenol with paraformaldehyde, as illustrated in FIG. 28:
  i. Prepare a solution of p-tert-butylphenol (25 to 100 g L$^{-1}$) along with paraformaldehyde (10 to 36 g L$^{-1}$) and sodium hydroxide (10 mol L$^{-1}$ aqueous solution; 0.15 to 15 mL) in xylene;
  ii. Stir and maintain under reflux conditions at a temperature of 130 to 150° C., for 4 to 10 hours; iii. Cool to room temperature;
  iv. Filter the precipitate and wash successively with portions of toluene, ethyl ether, acetone and distilled water, at a solid/solvent ratio of 20 to 25'% w/v;
  v. Dissolve the precipitate in chloroform to make a solution of 7.0 to 8.0% w/v and heat (40 to 60° C.);
  vi. Cool the solution to room temperature and filter the recrystallized solid obtained;

b. Obtainment of substance 8TA, from the O-alkylation of 8OH, as illustrated in FIG. 31:
  i. Prepare a solution of the solid obtained in step "a" (3 to 15 g $L^{-1}$) in dimethylformamide;
  ii. Heat at a temperature of 50 to 80° C., add sodium hydride (12 to 50 g $L^{-1}$), stir from 20 minutes to 3 hours and then add n-bromobutane (280 to 560 g $L^{-1}$) and potassium iodide (2 to 50 g $L^{-1}$);
  iii. Cool the solution to room temperature and stir for 72 to 96 hours;
  iv. Add dichloromethane (2.0 to 3.5% w/v);
  v. Wash the organic phase with acid solution of 0.1 mol $L^{-1}$;
  vi. Evaporate the organic phase, preferably by distillation;
  vii. Add acetone (2.0 to 20% w/v);
  viii. Filter the precipitate obtained in "vii";
c. Obtainment of substance 8NO, from the ipso-nitration of 8TA, as illustrated in FIG. 32:
  i. Prepare a solution of the solid obtained in step "b" (50 to 200 g·$L^{-1}$) together with sodium nitrate (260 to 1500 g $L^{-1}$) in acid, preferably glacial acetic acid;
  ii. Keep under stirring at room temperature for 4 to 10 hours;
  iii. Pour in distilled water (1.2 to 2.0% w/v), filter, wash the precipitate with (2.0 to 3.0% w/v) of methanol and then solubilize into ethyl acetate (30.0 to 60.0% w/v), add methanol (20.0 to 30.0% w/v) and filter the solid obtained;
d. Obtainment of substance 8NH, from the reduction of 8NO, as illustrated in FIG. 34:
  i. Prepare a solution of the solid obtained in step "c" (1 to 5 g L-=) along with hydrazine monohydride (90 to 300 g $L^{-1}$) and palladium (0.02 to 1.5 g $L^{-1}$) in a mixture of ethanol and tetrahydrouran (1:1; v/v);
  ii. Keep stirring under reflux conditions for 24 to 36 hours, filter palladium and wash the solid obtained with methanol (from 2.0 to 8.0% w/v) and an acidic methanol solution (2 mol $L^{-1}$; from 2.0 to 8.0% w/v);
  iii. Concentrate at least 50% of the organic phase and add distilled water (2 to 8% w/v);
  iv. Filter the precipitate obtained in "iii" and wash with distilled water;
e. Obtainment of immunogens V8N1 and V8N2 by the coupling reaction between calizarene 8NH and hapten GNC or GNE, respectively, as illustrated in FIG. 2:
  i. Prepare a mixture of hapten GNE or GNC (20 to 80 g $L^{-1}$) together with diisopropylethylamine (5 to g $L^{-1}$) and (benzotriazol-1-il-oxy)-tris(pyrrolidine)-phosphonium hexafluorophosphate (20 to 100 g $L^{-1}$) in anhydrous dichloromethane, under atmosphere of inert gas and stir for 30 to 50 minutes at room temperature;
  ii. Prepare a solution of the solid obtained in step "d" (4 to 25 g $L^{-1}$) in anhydrous dichloromethane, under inert gas atmosphere and stir for 5 to 15 minutes at room temperature;
  iii. Transfer the solution obtained in step "ii" dropwise, under inert gas atmosphere, to the vessel containing the mixture obtained in step "i", to a final concentration of 49 to 240 g $mL^{-1}$;
  iv. Stir at room temperature for 24 to 28 hours;
  v. Add dichloromethane and wash with saturated sodium bicarbonate solution and later with distilled water, dry, filter and evaporate the organic phase, preferably by distillation, and purify the product using preferably column chromatography.

The anti-drug vaccine, specifically anti-cocaine, comprises at least one of the immune system stimulating molecules defined above and pharmaceutically and pharmacologically acceptable excipients. It can be used in the preparation of a vaccine, for treating patients with addiction to drugs of abuse, preferably cocaine, and also to prevent fetal exposure to drugs, in pregnant women who use drugs, preferably cocaine.

The present invention can be better understood through the following not limiting examples.

Example 1—Synthesis of the Immunogen V4N1 and V4N2

The immunogens V4N1 and V4N2 were prepared by the coupling reaction between calixarene 4NH and hapten GNC or GNE, respectively, as represented in FIG. 2: The methodology used in the present invention for linking hapten GNC or GNE to calixarene 4NH is a methodology for forming amide bonds, adapted from Geraci, C.; Consoli, G. M. L.; Galante, E.; Bousquet, E.; Pappalardo, M.; Spadaro, A. Calix[4]arene decorated with four Tn Antigen Glycomimetic Units and P3CS Immunoadjuvant: synthesis, characterization, and Anticancer Immunological Evaluation. Bioconjugate Chem. 2008, 19, p.751-758.

Figure 3:
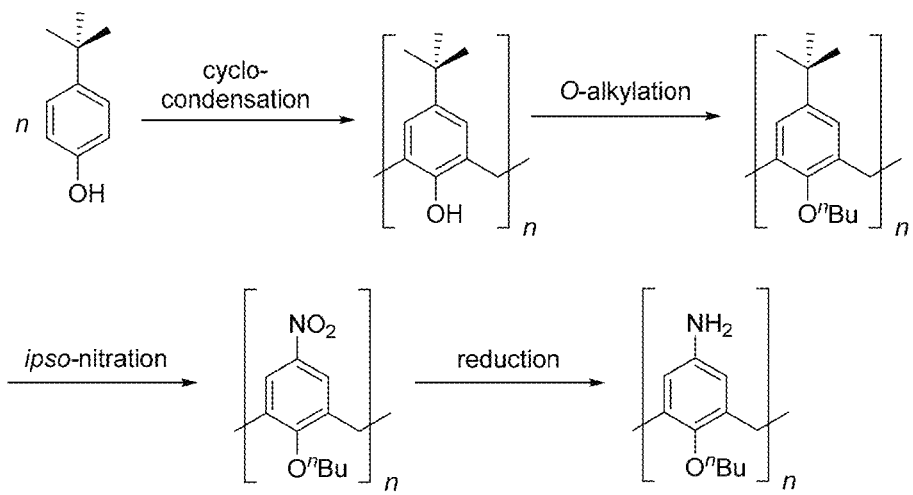
FIG. 3 presents the synthetic route to obtain calixarenes 4NH and 8NH.

Calixarene 4NH was prepared in four stages, from the p-tert-butylphenol, as represented in FIG. 3. The four reactions of the present invention are adaptations of four methodologies from the state of the art (Gutsche, C. D.; Iqbal, M. p-tert-butylcalix[4]arene. Org. Synth. 1990, 68, p.234-236; Kenis, P. J. A.; Noordman, O. F. J.; Schönherr, H.; Kerver, E. G.; Snellink-Ruël, B. H. M.; van Hummel, G. J.; Harkema, S.; van der Vorst, C. P. J. M.; Hare, J.; Picken, S. J.; Engbersen, J. F. J.; van Hulst, N. F.; Vancso, J.; Reinhoudt, D. N. Supramolecular materials: molecular packing of tetranitrotetrapropoxycalix[4]arene in highly stable films with second-order nonlinear optical properties. Chem. Eur. J. 1998, 4, p.1225-1234; Verboom, W.; Durie, A.; Egberink, R. J. M.; Asfari, Z.; Reinhoudt, D. N. Ipso Nitration of p-tert-Butylcalix[4]arenes. J. Org. Chem. 1992, 57, p.1313-1316; Sansone, F.; Dudic, M.; Donofrio, G.; Rivetti, C.; Baldini, L.; Casnati, A.; Cellai, S.; Ungaro, R. DNA Condensation and Cell transfection properties of Guanidinium Calixarenes: Dependence on macrocycle lipophilicity, size, and conformation. J. Am. Chem. Soc. 2006, 128, p.14528-14536).

The substance 4OH was obtained as represented in FIG. 4. The methodology developed in the present invention was adapted from Gutsche, C. D.; Iqbal, M. p-tert-butylcalix[4] arene. Org. Synth. 1990, 68, p.234-236. In a round-bottom flask containing 25.37 g (166.5 mmol) of p-tert-butylphenol, 18 mL of formaldehyde (solution at 37% in water) and 0.31 g (7.5 mmol) of sodium hydroxide were added. The reaction mixture was heated at a temperature of 110-120° C. and kept under mechanical stirring for 60 minutes. As the reaction progressed, the medium acquired a yellowish color and subsequently originated a yellow solid, on which 250 mL of diphenyl ether were added. The reaction system was kept under mechanical stirring for another 60 minutes, with foaming. Then, the reaction mixture was kept under reflux (approximately 260° C.) for 180 minutes and turned very dark. After reaching room temperature, about 500 mL of ethyl acetate were added in the medium and was kept under stirring for 120 minutes. After resting for approximately 12 hours, the solid obtained was removed by vacuum filtration and submitted to consecutive washes using ethyl acetate (100 mL), acetic acid (100 mL) and distilled water (500 mL). The desired product was obtained as a white solid at 51% yield (13.99 g).

The infrared spectrum obtained for the substance 4OH presents a characteristic band of O—H bond stretchings at 3158 cm$^{-1}$. An intense band was observed at the frequency of 1200 cm$^{-1}$, characteristic of C—O bond stretchings in combination with the angular deformations of O—H bonds. The bands related to the C=C bond stretchings of aromatic rings were observed in 1481 and 1462 cm$^{-1}$. Two absorption bands were verified in the frequencies of 1392 and 1361 cm$^{-1}$ possibly due to the angular deformations of C—H bonds of the tert-butyl groups.

Figure 5:
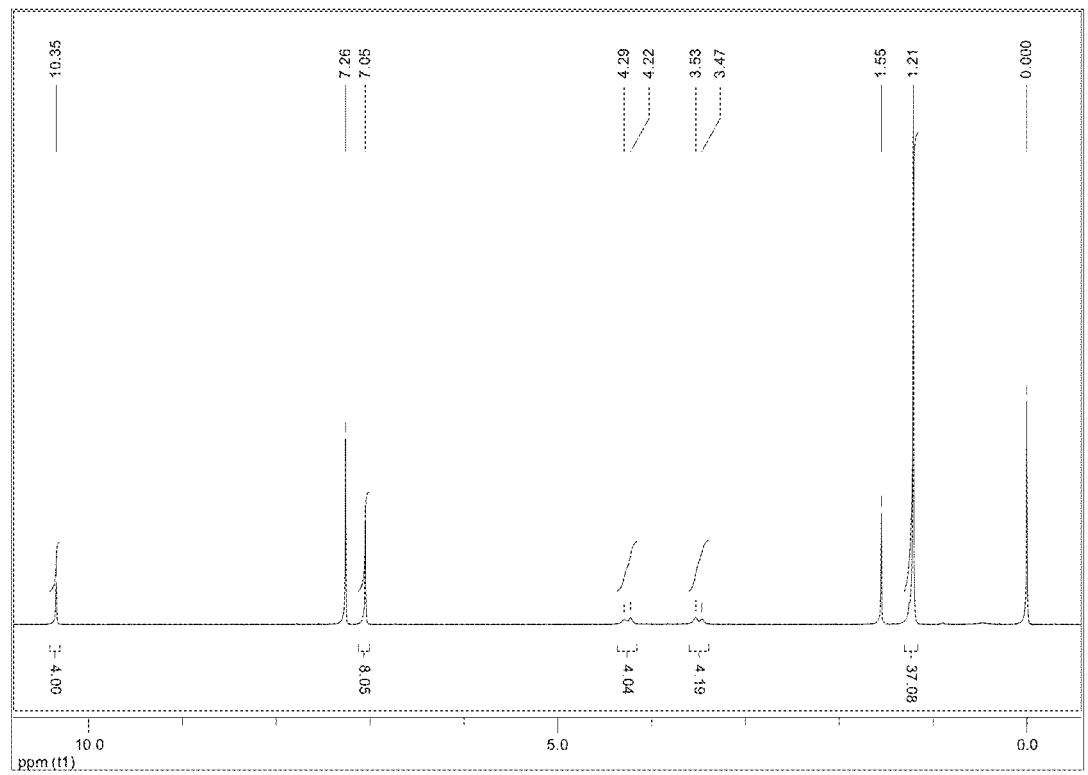
FIG. 5 presents the hydrogen nuclear magnetic resonance spectrum [$^1$H NMR; 200 MHz, CDCl$_3$] obtained for the substance 4OH.

In the $^1$H NMR spectrum of said substance (FIG. 5) the singlet at 1.21 ppm related to the 36 hydrogen atoms of the tert-butyl groups is observed. Centered at 3.50 and 4.26 ppm, two doublets related to hydrogens from methylene groups located between aromatic rings were observed. The singlet at 7.05 ppm, integrated for eight hydrogen atoms, was related to the hydrogens of the aromatic groups. Finally, the most unshielded signal of this spectrum, at 10.35 ppm, was related to the four phenolic hydrogens present in the 4OH structure.

In the $^{13}$C NMR spectrum of the 4OH substance, four signals (125.9; 127.7; 144.4 and 146.7 ppm) belonging to the carbons of the aromatic rings, of which only one (125.9 ppm) is present in the sub spectrum DEPT-135, is observed. The signal for carbon atoms —CH$_3$ at 31.4 ppm was also identified, and the sign for methylene carbons at 32.6 ppm that presents inverted phase in the SUBSPECTRUM DEPT-135 was also observed. At 34.0 ppm, the sign for non-hydrogenated carbons of the groups tert-butyl groups was observed.

The substance 4TA was obtained as represented in FIG. 6. The methodology developed in the present invention relates to an adaptation of Kenis, P. J. A.; Noordman, O. F. J.; Schbnherr, H.; Kerver, E. G.; Snellink-Rual, B. H. M.; van Hummel, G. J.; Harkema, S.; van der Vorst, C. P. J. M.; Hare, J.; Picken, S. J.; Engbersen, J. F. J.; van Hulst, N. F.; Vancso, J.; Reinhoudt, D. N. Supramolecular materials: molecular packing of tetranitrotetrapropoxycalix[4]arene in highly stable films with second-order nonlinear optical properties. Chem. Eur. J. 1998, 4, p.1225-1234. In a 100 mL round-bottom flask containing 0.65 g (1 mmol) of 4OH, 20 mL of anhydrous dimethylformamide (DMF) and 0.20 g (5 mmol) of sodium hydride (60, in mineral oil) were added. The reaction mixture was kept under magnetic stirring for 60 minutes at room temperature and then 0.69 g (5 mmol) of n-bromobutane was added. The system was maintained at 60° C. for 24 hours under magnetic stirring. After cooling to room temperature, stirring was interrupted and approximately 5 mL of cold distilled water was added for solid precipitation. The precipitate was filtered under vacuum and subsequently washed with methanol. 0.67 g of a white solid was obtained, corresponding to 77% reaction yield.

In the infrared spectrum obtained for substance 4TA, it is possible to verify the disappearance of the characteristic band of O—H bond stretchings at 3158 cm$^{-1}$, present in the spectrum of substance 4OH. Stretching bands of C—H bonds from the tert-butyl groups could be identified at 2954 and 2867 cm$^{-1}$. An intense band was observed at 1199 cm$^{-1}$, which is characteristic of C—O—C stretchings of alkyl aril ether bonds.

Figure 7:
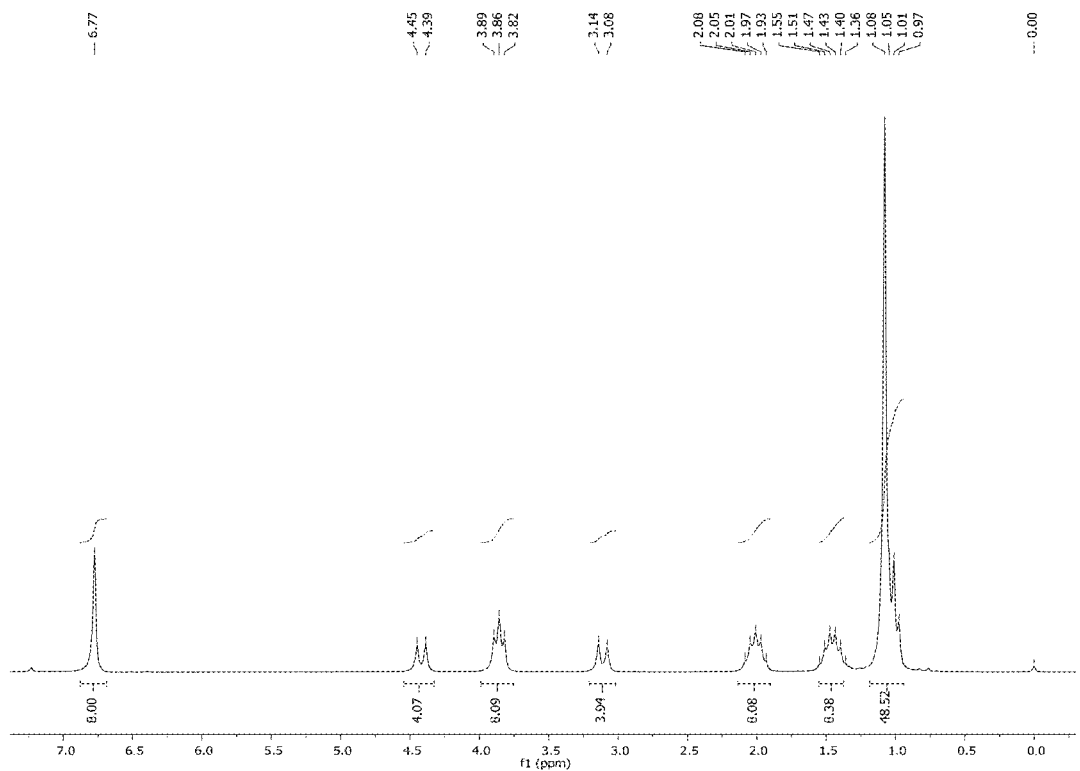
FIG. 7 presents the hydrogen nuclear magnetic resonance spectrum [$^1$H NMR; 200 MHz, CDCl$_3$] obtained for substance 4TA.

In the $^1$H NMR spectrum of said substance (FIG. 7), it is possible to identify a multiplet at 1.08-0.97 ppm, integrated for 48 hydrogens, attributed to —CH$_3$ hydrogens of tert-butyl and n-butyl groups. Methylene hydrogens located between aromatic rings are presented as a pair of doublets at 4.42 and 3.11 ppm (J=12.0 Hz).

The $^{13}$C NMR spectrum of said substance contains the signals of tert-butyl groups (at 31.7 ppm and 34.0 ppm) and the signals of the four carbons of the n-butyl groups, among them, the signal of the terminal carbon at 14.4 ppm.

The substance 4NO was obtained as represented in FIG. 8. The methodology of the present invention was adapted from Verboom, W.; Durie, A.; Egberink, R. J. M.; Asfari, Z.; Reinhoudt, D. N. Ipso Nitration of p-tert-Butylcalix[4] arenes. J. Org. Chem. 1992, 57, p.1313-1$^{316}$. 0.87 g (1.0 mmol) of 4TA, 1.2 mL of trifluoroacetic acid (TFA), 1 mL of steaming HNO; (dropwise) and 10 mL of DCM were added to a round-bottom flask. After one hour under magnetic stirring at room temperature, the reaction was ended, pouring it into a beaker containing 50 ml of iced water. Then, a liquid-liquid extraction was carried out using 50 mL of DCM. The organic phase was washed with saturated solution of NaHCO$_3$ (2×20 mL) and saturated solution of NaCl (2×20 mL) and subsequently dried with anhydrous MgSO$_4$ and filtered. After concentrating the organic phase using the rotary evaporator under reduced pressure, the raw product was recrystallized in a mixture of CHCl$_3$/MeOH. After performing a filtration under reduced pressure, the desired product was obtained as a white solid at 91% yield (0.75 g).

In the infrared spectrum obtained for the substance 4NO, two important bands at 1515 and 1343 cm$^{-1}$ were identified, which are probably and respectively related to the asymmetric and symmetrical stretchings of the nitro groups.

Figure 9:
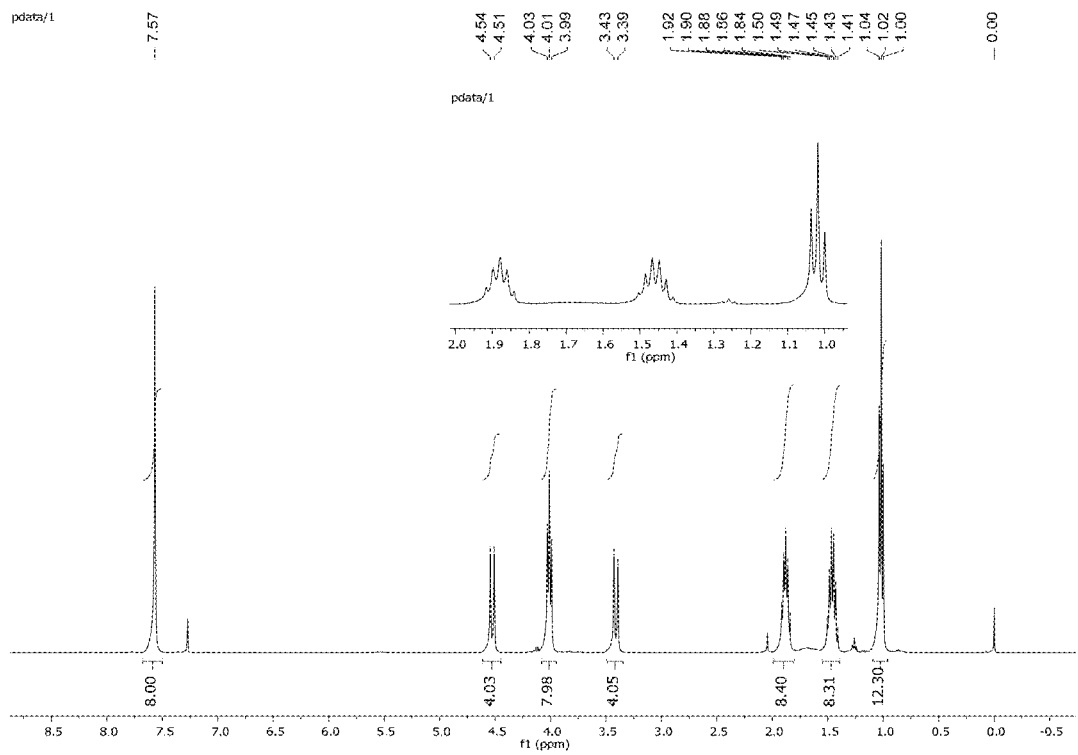
FIG. 9 presents the hydrogen nuclear magnetic resonance spectrum [$^1$H NMR; 400 MHz, CDCl$_3$] obtained for substance 4NO.

In the $^1$H NMR spectrum of said substance (FIG. 9), the main change in the spectrum of the starting material 4TA is the disappearance of the multiplet sign related to the hydrogens from tert-butyl group (1.08-0.97 ppm, integrated for 48 hydrogens). The triplet at 1.02 ppm, integrated for 12 hydrogen atoms, was related to —CH$_3$ hydrogens from the n-butyl group. The sign of aromatic hydrogens at 7.57 ppm, integrated for 8 hydrogens, is justified by the high withdrawing effect of the electronic density, promoted by nitro groups. The other signs present in the spectrum were attributed to methylene hydrogens between the rings (4.53 ppm and 3.41 ppm) and to the aliphatic hydrogens of the n-butyl group.

The analysis and interpretation of the $^{13}$C NMR spectra of $^{13}$C and DEPT-135 of 4NO indicated the presence of four signals of aromatic carbons (161.9; 143.1; 135.6 and 124.2 ppm); however only one of them, at 124.2 ppm, is hydrogenated. This data is consistent with the proposed structure for the 4NO product. The two-dimensional HSQC experiment allowed the correlation of signs with very close 5 (32.3 and 31.3 ppm).

The substance 4OH was obtained as represented in FIG. 10. The methodology developed in the present invention was adapted from Sansone, F.; Dudic, M.; Donofrio, G.; Rivetti, C.; Baldini, L.; Casnati, A.; Cellai, S.; Ungaro, R. DNA Condensation and Cell transfection properties of Guanidinium Calixarenes: Dependence on macrocycle lipophilicity, size, and conformation. J. Am. Chem. Soc. 2006, 128, p.14528-14536. 0.50 g (0.60 mmol) of 4NO was weighted and added to a round-bottom flask. Then, 5.0 mL of hydrazine monohydride, 25 mL of absolute ethanol and a catalytic amount of palladium/carbon 10% were added. The reaction mixture was kept under magnetic stirring at a temperature of 80° C. for 48 hours. After this period, the catalyst was removed by simple filtration and the filtered organic phase concentrated in a rotary evaporator. The solid obtained was washed with distilled water, providing the product of interest with 94% yield (0.40 g).

Figure 11:
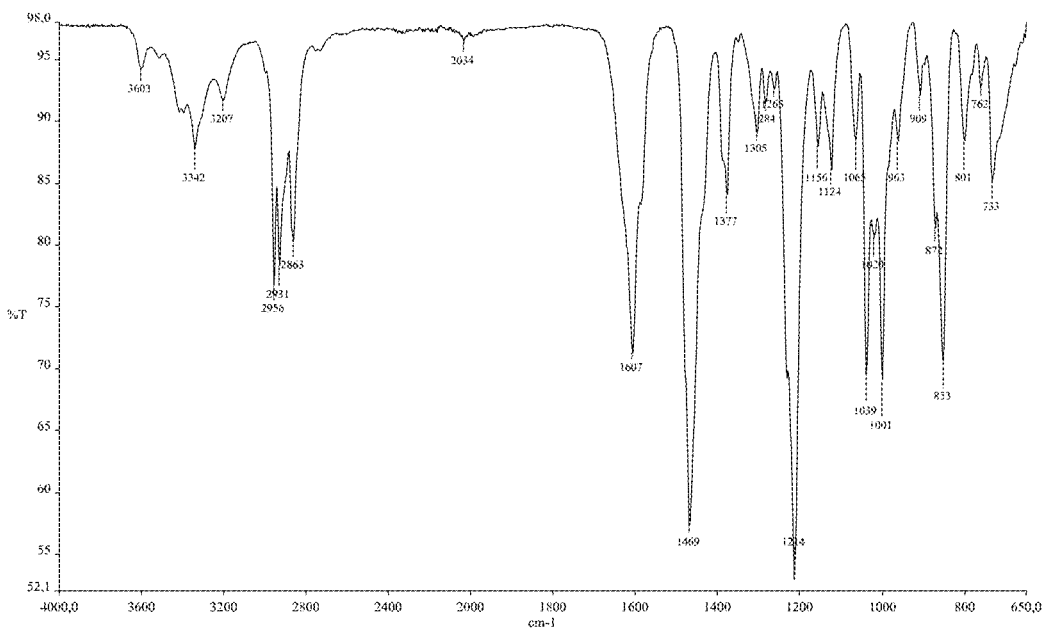
FIG. 11 presents the infrared spectrum obtained for substance 4NH.

In the infrared spectrum obtained for the substance 4NH (FIG. 11), the absence of absorption bands at 1515 and 1343 cm$^{-1}$ is noted, which are characteristics of the nitro groups and present in the 4NO precursor spectrum. In addition, it is possible to identify in the 4HN spectrum bands around 3342 cm$^{-1}$, possibly associated with stretchings of aromatic primary amines.

Figure 12:
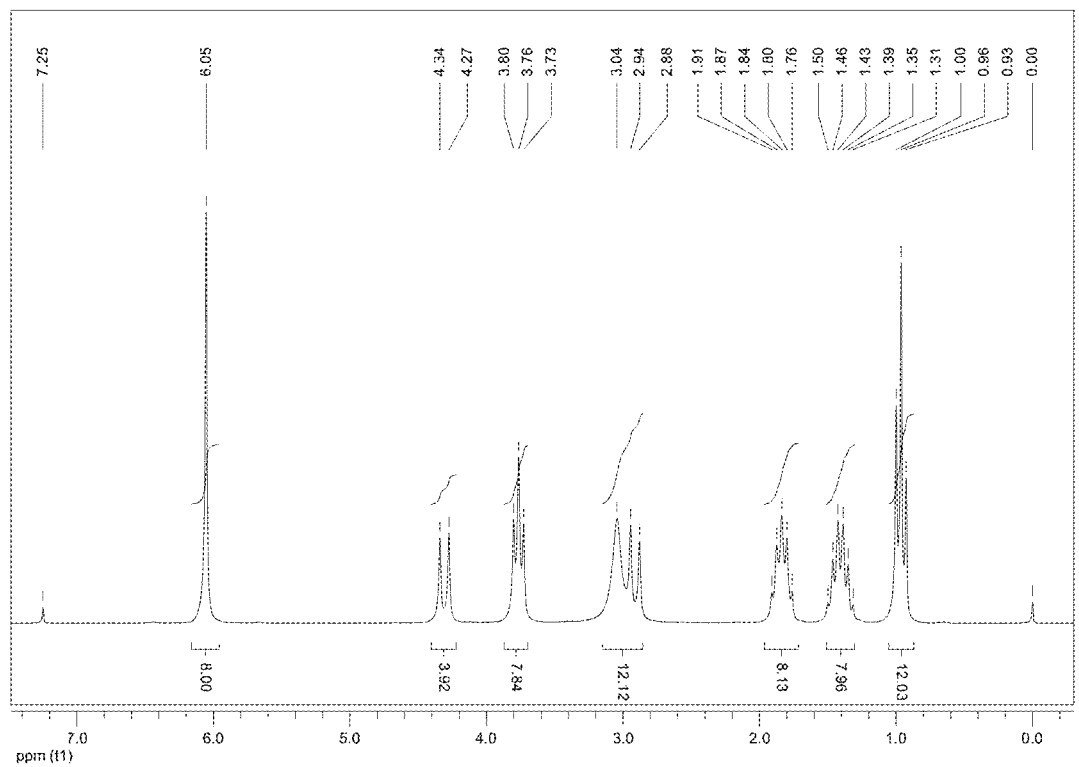
FIG. 12 presents the hydrogen nuclear magnetic resonance spectrum [$^1$H NMR; 200 MHz, CDCl$_3$] obtained for substance 4NH.

In the $^1$H NMR spectrum of said substance (FIG. 12), the singlet signal is observed, which is related to the eight aromatic hydrogens, at 6.05 ppm, while this same signal, in the 4NO precursor (FIG. 9), is observed at 7.58 ppm. This signal is verified in a more shielded region in the 4NH spectrum, probably by the donor effect caused by the electronic density of the amino groups. It is further possible to verify the broad signal attributed to hydrogens form the NH: group at δ 3.04, superimposed to the doublet of one of the hydrogens of the methylene bridge.

Figure 13:
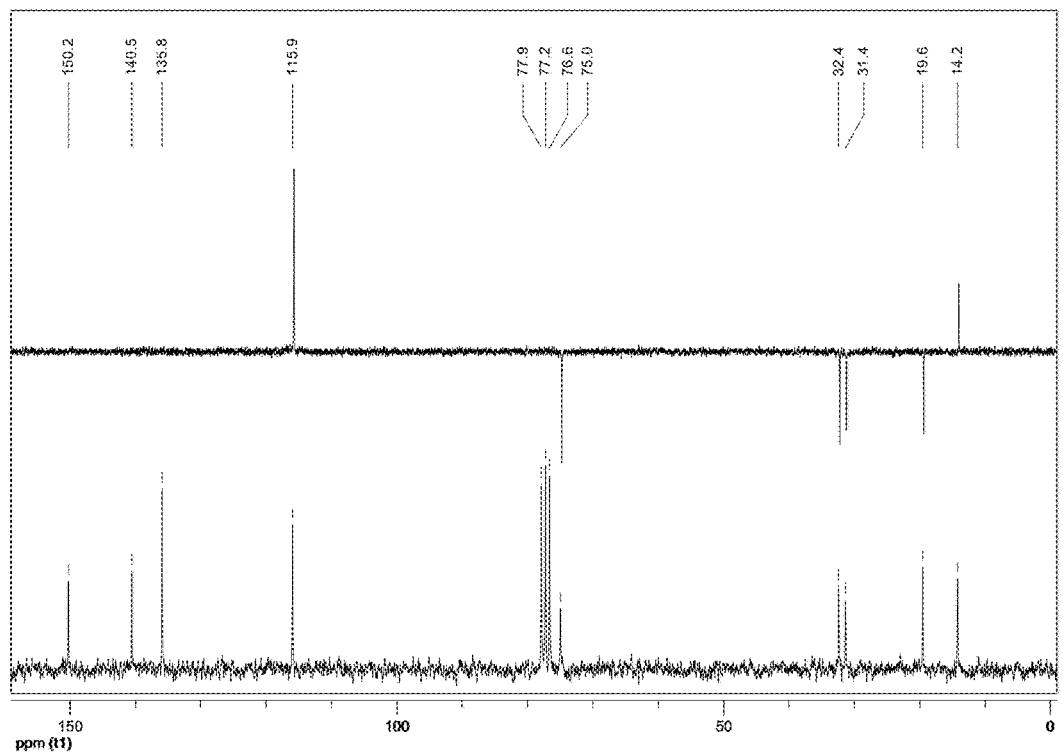
FIG. 13 presents the carbon nuclear magnetic resonance spectrum [$^{13}$C NMR; 50 MHz, CDCl$_3$] obtained for substance 4NH.

It is observed in the $^{13}$C NMR spectrum of said substance (FIG. 13), when compared with the 4NO precursor spectrum, that there is a change in the value of chemical shifts of aromatic carbons, especially in the carbons of the ortho and para positions. The amino group increases the electronic density on the carbons of these positions due to the resonance effect and, for this reason, these are observed in a more shielded region of the spectrum.

Figure 14:
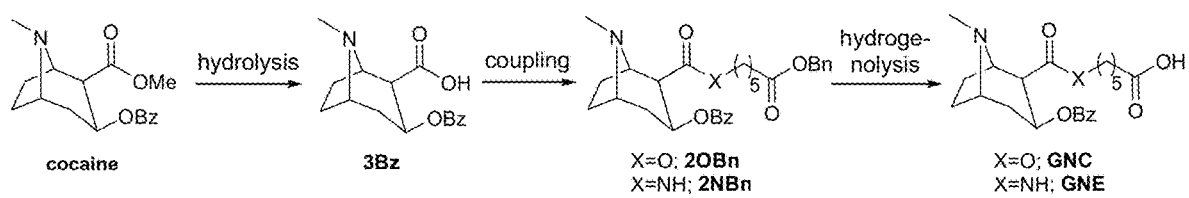
FIG. 14 presents the synthetic route for obtaining the haptens GNE and GNC.

The preparation of GNE hapten, a cocaine analogue, was performed as represented in FIG. 14. The reactions of FIG. 14 were developed in the present invention based on Findlay, S. P. The three-dimensional structure of the Cocaines: Part I. Cocaine and Pseudococaine. J. Am. Chem. Soc. 1954, 11, p.2855-2862; Sakurai, M.; Wirsching, P.; Janda, K. D. Design and synthesis of a cocaine-diamide hapten for vaccine development. Tetrahedron Lett. 1996, 37, p.5479-5482; Cai, X.; Whitfield, T.; Hixon, M. S.; Grant, Y.; Koob, G. F.; Janda, K. D. Probing active cocaine vaccination performance through catalytic and noncatalytic hapten design. J. Med. Chem. 2013, 56, p. 3701-3709.

The preparation of GNC hapten, another cocaine analogue, was performed as represented in FIG. 14. These reactions were developed in the present invention based on the works of Findlay, S. P. The three-dimensional structure of the Cocaines: Part I. Cocaine and Pseudococaine. J. Am. Chem. Soc. 1954, 11, p.2855-2862; Sakurai, M.; Wirsching, P.; Janda, K. D. Design and synthesis of a cocaine-diamide hapten for vaccine development. Tetrahedron Lett. 1996, 37, p.5479-5482; Cai, X.; Whitfield, T.; Hixon, M. S.; Grant, Y.; Koob, G. F.; Janda, K. D. Probing active cocaine vaccination performance through catalytic and noncatalytic hapten design. J. Med. Chem. 2013, 56, p. 3701-3709.

Figure 15:
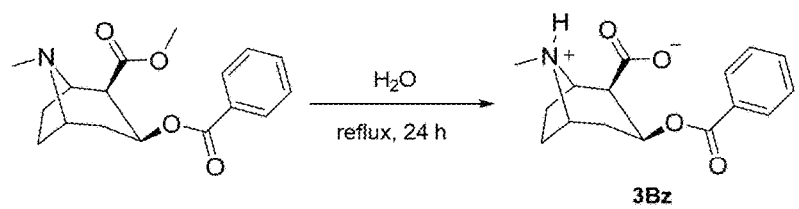
FIG. 15 presents the reaction scheme for obtaining substance 3Bz.

The 3Bz substance was obtained from cocaine hydrolysis, as represented in FIG. 15 (Findlay, S. P. The three-dimensional structure of the Cocaines: Part I. Cocaine and Pseudococaine. J. Am. Chem. Soc. 1954, 11, p. 2855-2862).

In this methodology, 3.87 mmol of cocaine were added to 20 mL of distilled water and the system was heated and kept under reflux and magnetic stirring for 24 hours. After removing the solvent and adding 80 mL of acetone, the desired product 3Bz was obtained at 84% yield.

The infrared spectrum obtained for the 3Bz substance presented a characteristic stretching band of N—H bonds at 3224 cm$^{-1}$, the stretching band of carbonyls of ester groups (1718 cm$^{-1}$) and also an asymmetric stretching band of carboxylate groups (1590 cm$^{-1}$).

Figure 16:
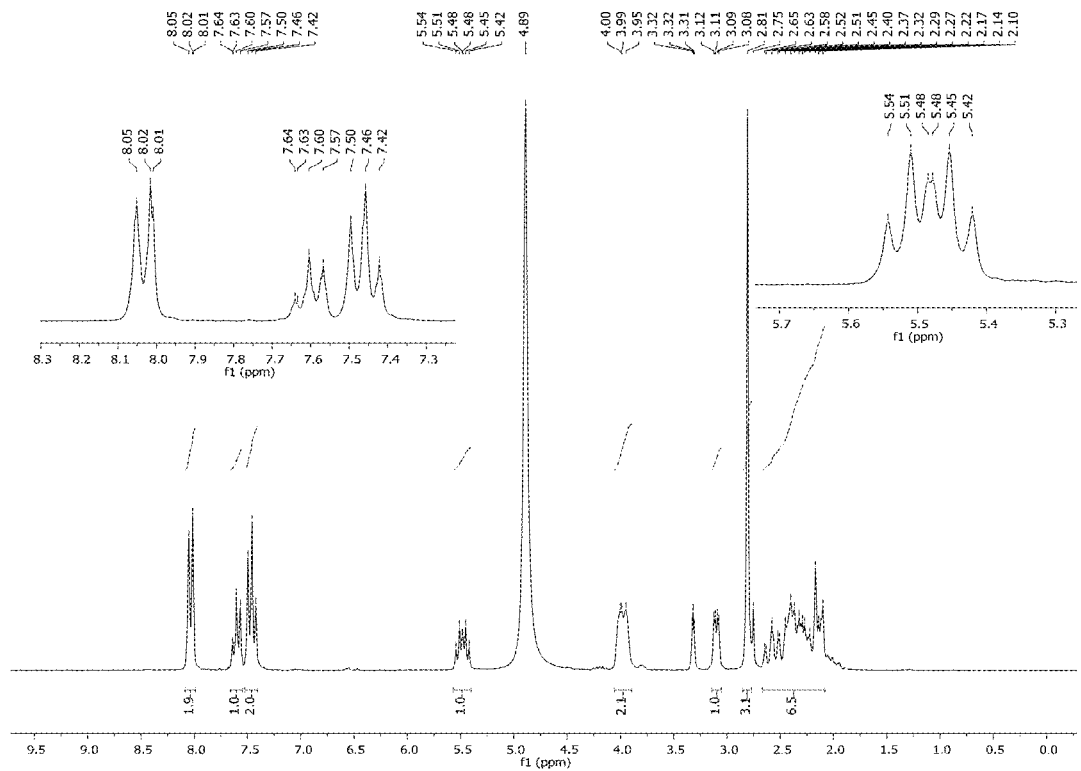
FIG. 16 presents the hydrogen nuclear magnetic resonance spectrum [$^1$H NMR; 200 MHz, CD$_3$OD] obtained for substance 3Bz.

In the $^1$H NMR spectrum of said substance (FIG. 16), the hydrogen signals of the benzoyl group were observed: a multiplet at 8.05-8.01 ppm (attributed to ortho hydrogens to the substituent), a multiplet at δ 7.64-7.57 ppm (related to para hydrogen to the substituent) and a triplet at 7.46 ppm (attributed to meta hydrogens to the substituent).

14 signals in the $^{13}$C NMR spectrum of said substance are observed, and this is consistent with the proposed structure for 3Bz, especially the signal at 177.2 ppm of the carbon from the benzoyl ester group and the sign at 50.3 ppm from the methyl carbon linked to the nitrogen atom. Three carbon signals with inverted phase were observed in the DEPT-135 spectrum at 34.4, 25.1 and 24.7 ppm, related to the three methylene carbons of the structure.

Figure 17:
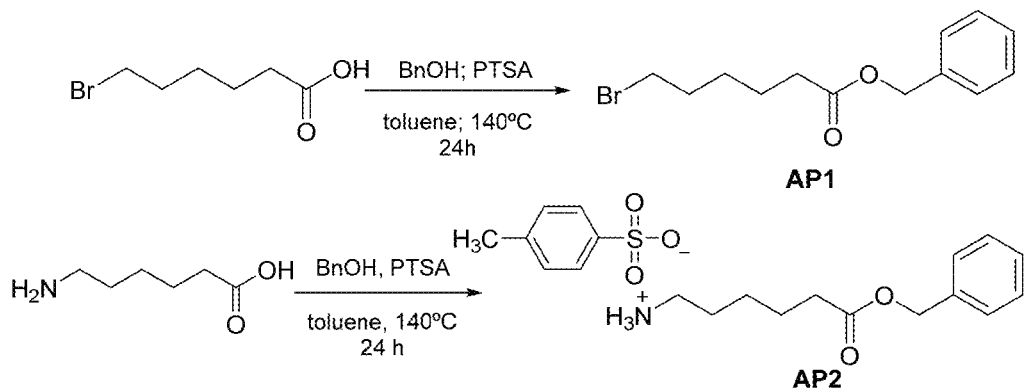
FIG. 17 presents the reaction scheme for obtaining substances AP1 and AP2.

The AP1 substance was obtained from 6-bromo hexanoic acid (Bezwada, R. S. Functionalized Biodegradable triclosan monomers and oligomers for controlled release. Patent US 2009/0105352 A1, 2009), as represented in FIG. 17. In a 125 mL round-bottom flask containing 2.34 g (12 mmol) of 6-bromo hexanoic acid, 1.30 g (12 mmol) of benzyl alcohol was added, along with 0.06 g (0.30 mmol) of p-toluene sulfonic acid monohydrate and 50 mL of toluene. The condenser system and the Dean-Stark apparatus were attached to the round-bottom flask. The system was heated and kept under reflux under magnetic stirring for 24 hours. After the end of the reaction, liquid-liquid extraction was performed using a 5% NaHCO$_3$ solution (2×50 mL). The organic phase was dried with anhydrous sodium sulfate, filtered and evaporated using a rotary evaporator. The light brown color desired product was obtained with 69% yield (2.36 g).

In the AP1 spectrum in the infrared region performed at ATR, an absorption band at 1731 cm$^{-1}$ was observed, related to the C═O bond stretching of benzyl ester. The bands present at 1496 and 1454 cm$^{-1}$ were associated with C═C bond stretching of the aromatic ring. The band at 3032 cm$^{-1}$ was related to C—H stretching of the aromatic ring. The band at 1253 cm$^{-1}$ was related to C—O benzyl ester bond stretching.

Figure 18:
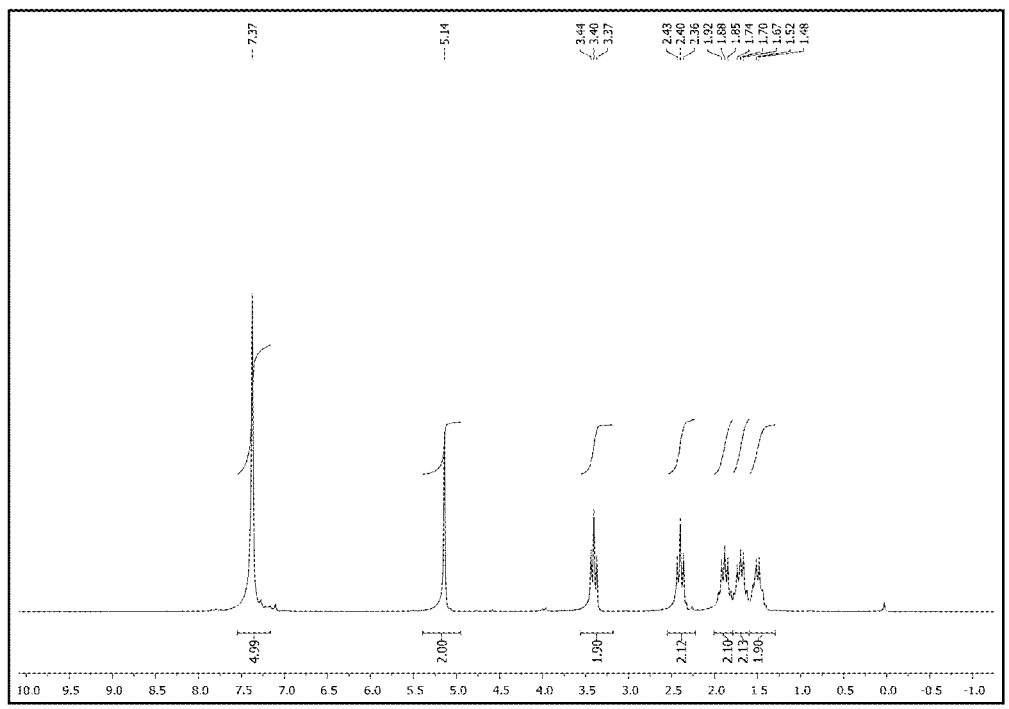
FIG. 18 presents the hydrogen nuclear magnetic resonance spectrum [$^1$H NMR; 200 MHz, CDCl$_3$] obtained for substance AP1.

In the $^1$H NMR spectrum of product AP1 (FIG. 18) a broad signal at 7.37 ppm, integrated to 5H, was related to the hydrogen atoms of the aromatic ring. A singlet at 5.14 ppm, integrated for 2H, was related to the methylene hydrogens of the benzyl protecting group.

In the C NMR spectrum of product AP1, the benzyl ester carbonyl signal was identified at 173.1 ppm, which disappeared, as it has been already expected, in the sub spectrum DEPT-135. Only two signals of hydrogenated carbons (128.1 and 128.5 ppm) were identified in the region of aromatic carbons. However, according to the product structure, three signs were predicted in this region. As the signal intensity at 128.1 ppm is higher than the signal at 128.5 ppm, it is concluded that the first sign is probably attributed to three out of the five atoms of the aromatic ring of AP1.

The substance AP2 was obtained from 6-aminohexanoic acid, as it is represented in FIG. 17. In a 50 mL round-bottom flask containing 1.32 g (10.1 mmol) of 6-aminocaproic acid, 3.82 g (35.3 mmol) of benzyl alcohol was added, along with 2.01 g (10.6 mmol) of p-toluene sulfonic acid and 25 mL of toluene. The condenser system and the Dean-Stark apparatus were attached. The system was heated and kept under reflux under magnetic stirring for 24 hours. Then, the precipitate obtained was filtered under reduced pressure and the solid was washed with approximately 50 mL of ethyl ether. The solid formed, with slightly yellowish color, was obtained with 99% yield (3.93 g).

The infrared spectrum obtained for the substance AP2 presents characteristic bands of the NH; stretching at 3262 and 3186 cm$^{-1}$ and a band characteristic of ester carbonyls at 1725 cm$^{-1}$. The bands present at 1194 and 1161 cm$^{-1}$ were associated with ester C—O bond stretchings.

In the $^1$H NMR spectrum of said substance (FIG. 18) signals are observed at 5.07 ppm and 7.32 ppm, which are attributed respectively to the methylene and aromatic hydrogens of the benzyl group. It is also possible to identify in the region of aromatic hydrogens of this spectrum two doublets (7.73 and 7.15 ppm; J=8.0 Hz) related to the aromatic hydrogens of the tosylate group.

It is observed, in the $^{13}$C NMR spectrum of that substance, the signal at 173.3 ppm related to the carbonyl of the formed ester group. Seven signals were identified in the region of aromatic carbons; however, eight signals would be expected, according to the proposed structure. The sign at 128.3 ppm has an intensity approximately 30% higher than the signal intensity at 128.7 ppm, suggesting that the most intense sign is related to two distinct aromatic carbons. Other signals present, as the one in 21.4 ppm related to the methyl group of tosylate, confirmed the obtainment of the desired product.

Figure 20:
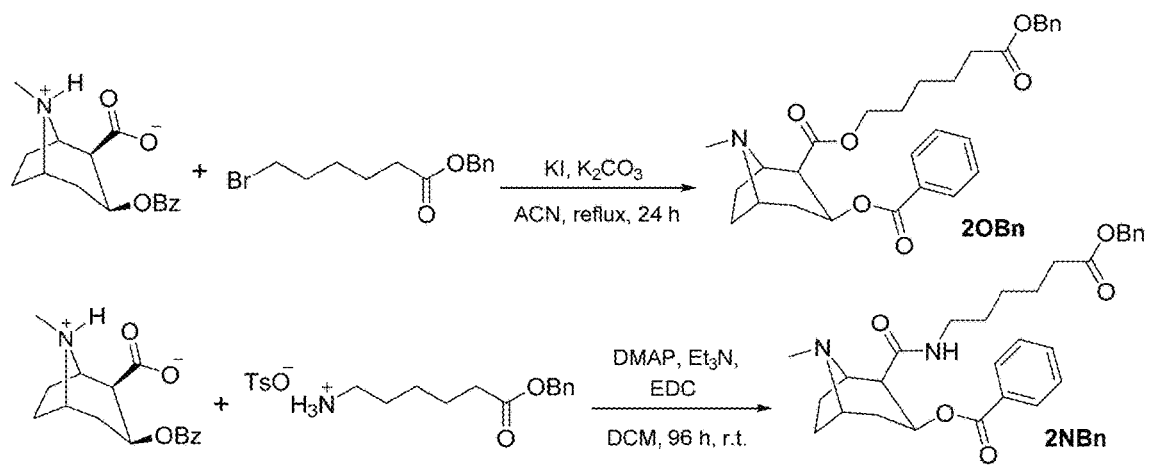
FIG. 20 presents the reaction for obtaining intermediates 2NBn and 2OBn.

The substance 2OBn was obtained by submitting AP1 and 3Bz fragments to an acetonitrile reaction under reflux, in the presence of potassium carbonate and, in catalytic amounts, potassium iodide, as represented in FIG. 20 (Meijler, M. M.; Kaufmann, G. F.; Qi, L.; Mee, J. M.; Coyle, A. R.; Moss, J. A.; Wirsching, P.; Matsushida, M.; Janda, K. D. Fluorescent cocaine probes: a tool for the selection and engineering of therapeutic antibodies. *J. Am. Chem. Soc.* 2005, 127, p. 2477-2484). In a 125 mL round-bottom flask containing 0.58 g (2 mmol) of 3Bz, 0.57 g (2 mmol) of AP1, 0.28 g (2 mmol) of potassium carbonate, 0.33 g (0.2 mmol) of potassium iodide and 15 mL of acetonitrile were added. After coupling the condenser to the round-bottom flask, the reaction was initiated at a temperature of 80° C. and under magnetic stirring. After 72 hours, the reaction was ended and the solvent was evaporated in the rotary evaporator. The reaction crude was solubilized in 30 mL of ethyl acetate and the organic phase was washed with distilled water (3×15 mL). Then, it was dried with anhydrous magnesium sulfate, filtered and concentrated in the rotary evaporator. The solid obtained was purified in a chromatography column using DCM/MeOH (98:2; v/v) as eluent, thus obtaining 0.71 g (72%) of the desired product.

The infrared spectrum of compound 2OBn presents characteristic bands of C=O ester bond stretchings at 1736 and 1712 cm$^{-1}$. Another band observed at 1275 cm$^{-1}$ was related to the C—O bond stretchings of ester groups.

The $^1$H NMR spectrum analysis of the product 2OBn (FIG. 21) confirmed the chemical structure proposed for 2OBn. At 5.10 ppm a singlet related to the hydrogens of methyl carbon of the benzyl protection group is observed. The region of aromatic hydrogens include some overlapping signals: at 7.45 ppm, a broad signal was related to aromatic hydrogens from the benzyl protecting group, whereas at 7.52 ppm a triplet was related to the aromatic hydrogen of benzyl ester.

The analysis of the $^{13}$C NMR spectrum and of the DEPT-135 sub spectrum of the substance 2OBn indicated the presence of the three carbonyls: 173.3, 170.3 and 166.3 ppm.

The substance 2NBn was obtained from the coupling between substances 3Bz and AP2 (Sakurai, M.; Wirsching, P.; Janda, K. D. Design and synthesis of a cocaine-diamide hapten for vaccine development. *Tetrahedron Lett.* 1996, 37, p. 5479-5482). 1.16 g (4 mmol) of 3Bz, 1.57 g (4 mmol) of AP2 and 0.50 g (4 mmol) of dimethylaminopyridine (DMAP) were added to a three-neck round-bottom flask. Then, 20 mL of anhydrous CH$_2$Cl$_2$ were added and the system was kept under argon atmosphere and magnetic stirring for 90 minutes in an ice bath. 0.86 g (4.4 mmol) of EDC was added to another round-bottom flask, along with 0.56 mL (4 mmol) of triethylamine and 10 mL of anhydrous CH$_2$Cl$_2$. After 10 minutes under magnetic stirring, the content was transferred to the three-neck round-bottom flask dropwise, under inert gas atmosphere. After 96 hours of magnetic stirring at room temperature, the reaction was ended and the organic phase was washed using 10% citric acid aqueous solution (3×15 mL). Then, the organic phase was washed using, respectively, 20 mL of distilled water and 20 mL of concentrated aqueous solution of NaCl. The organic phase was dried with anhydrous Na$_2$SO$_4$, filtered and concentrated under reduced pressure in the rotary evaporator. After column chromatography [ethyl acetate/hexane/triethylamine (30:10:4)], the desired product was purified and obtained with 71% yield (1.39 g).

Figure 19:
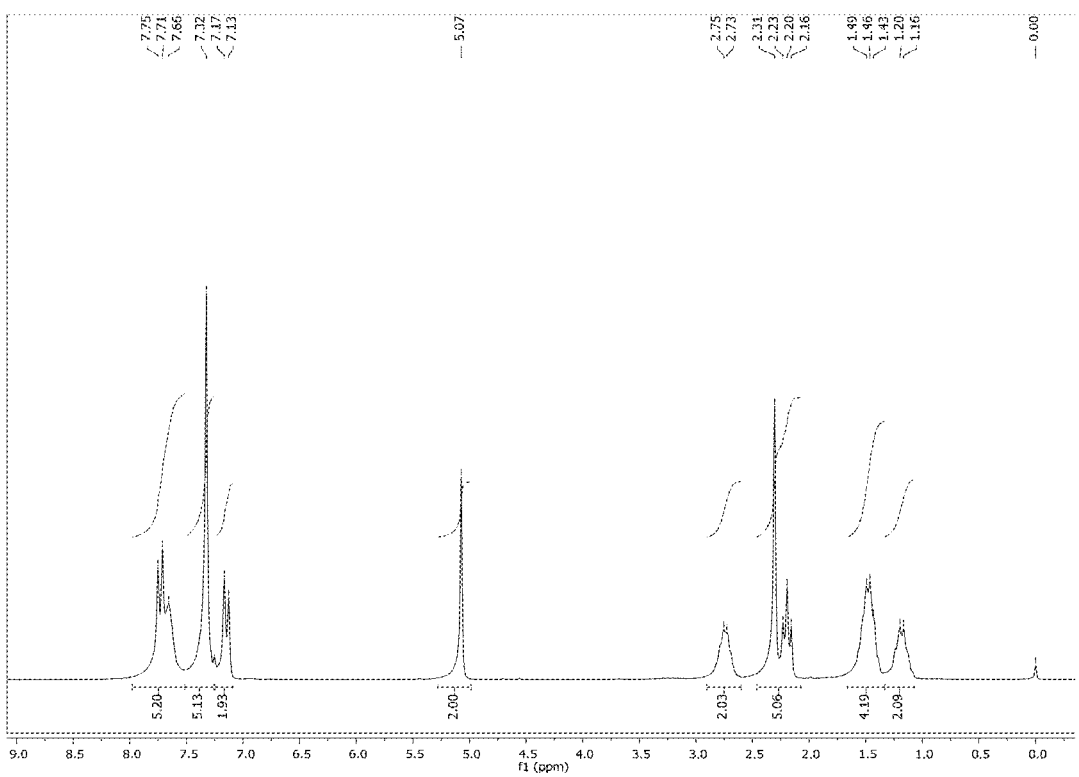
FIG. 19 presents the hydrogen nuclear magnetic resonance spectrum [$^1$H NMR; 200 MHz, CDCl$_3$] obtained for substance AP2.

The infrared spectrum obtained for substance 2NBn (FIG. 19) presents characteristic bands of C=O amide bond stretchings at 1663 cm$^{-3}$. Other bands observed at 1718 and 1276 cm$^{-1}$ were related, respectively, to the C=O and C—O bond stretchings of the ester groups.

In the $^1$H NMR spectrum of substance 2NBn, a signal is observed at 9.54 ppm related to the hydrogen of the amide bond formed. The doublet integrated for two hydrogens at 7.98 ppm was related to H$_{11}$. The other aromatic hydrogens were related to the multiplet centered at 7.41 ppm (integrated for eight hydrogens). Two other important signs are the double triplet at 5.31 ppm, related to H., and the singlet at 5.10 ppm of H$_{21}$.

The analysis of the $^{13}$C NMR spectrum, along with the DEPT-135 spectrum (FIG. 20) were also able to confirm the product structure of interest. In the region of aromatic carbons, 8 distinct signals were expected; however, only seven signals were identified, a fact explained by the probable overlap of two signals, as it has been previously discussed for the AP2 fragment. As expected, nine signals of methylene carbons were identified, including the C$_{21}$ sign at 65.9 ppm.

Figure 23:
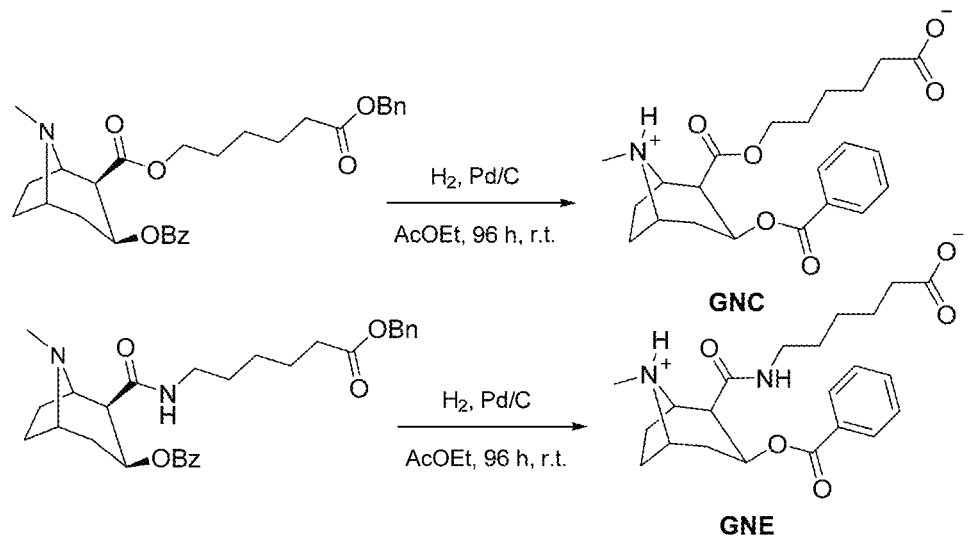
FIG. 23 presents the reactions for obtaining haptens GNC and GNE.

GNC hapten was obtained from the hydrogenolysis reaction of 2OBn, as represented in FIG. 23 (Cai, X.; Whitfield, T.; Hixon, M. S.; Grant, Y.; Koob, G. F.; Janda, K. D. Probing active cocaine vaccination performance through catalytic and noncatalytic hapten design. *J. Med. Chem.* 2013, 56, pages 3701-3709). 0.24 g (0.48 mmol) of 2OBn were transferred to a stainless steel reactor along with 0.06 g of 105 Pd/C and 25 mL of ethyl acetate. The system was subjected to H$_{2\ (g)}$ pressure (50 Kgf·cm$^{-1}$) and magnetic stirring for 48 hours at room temperature. Subsequently, the reaction was filtered in Celite for catalyst removal and the solvent was evaporated in a rotary evaporator under reduced pressure. 0.19 g of the desired product (84% yield) was obtained as a slightly yellowish solid.

The spectrum of the infrared region of GNC compound (FIG. 24) presents a characteristic band that is attributed to the C=O ester bond stretchings (1710 cm$^{-1}$). Two other important bands were observed: one at 1559 cm$^{-1}$ related to the asymmetric stretching of carboxylate group and another at 1272 and 1227 cm$^{-1}$ related to C—O stretchings of carboxylic acids and esters.

Figure 21:
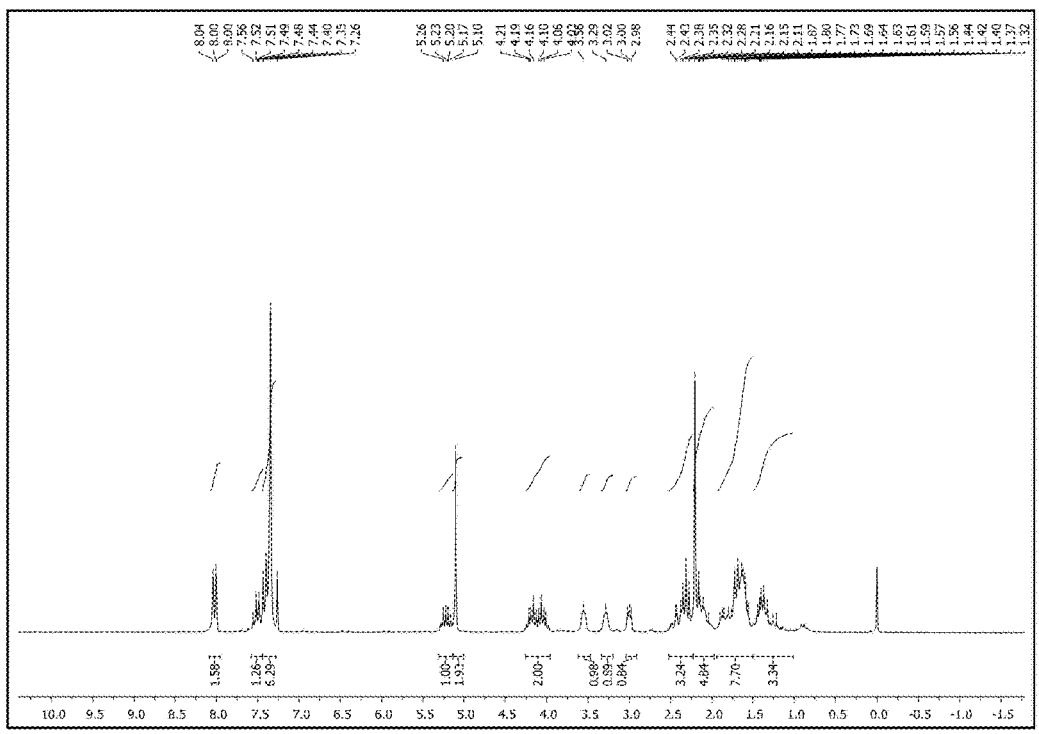
FIG. 21 presents the hydrogen nuclear magnetic resonance spectrum [$^1$H NMR; 200 MHz, CDCl$_3$] obtained for substance 2OBn.

It is noted, in the $^1$H NMR spectrum of hapten GNC (FIG. 25), the disappearance of the characteristic signals of aromatic hydrogens of the benzyl protecting group, that were evident singlets at 7.34 and 7.35 ppm, in the spectrum of its intermediate, product 2OBn (FIG. 21). It is possible to observe, in the $^1$H RMN spectrum of hapten GNC in the region of aromatic hydrogens, the triplets related to hydrogens of the alkaloid benzyl ester.

Figure 26:
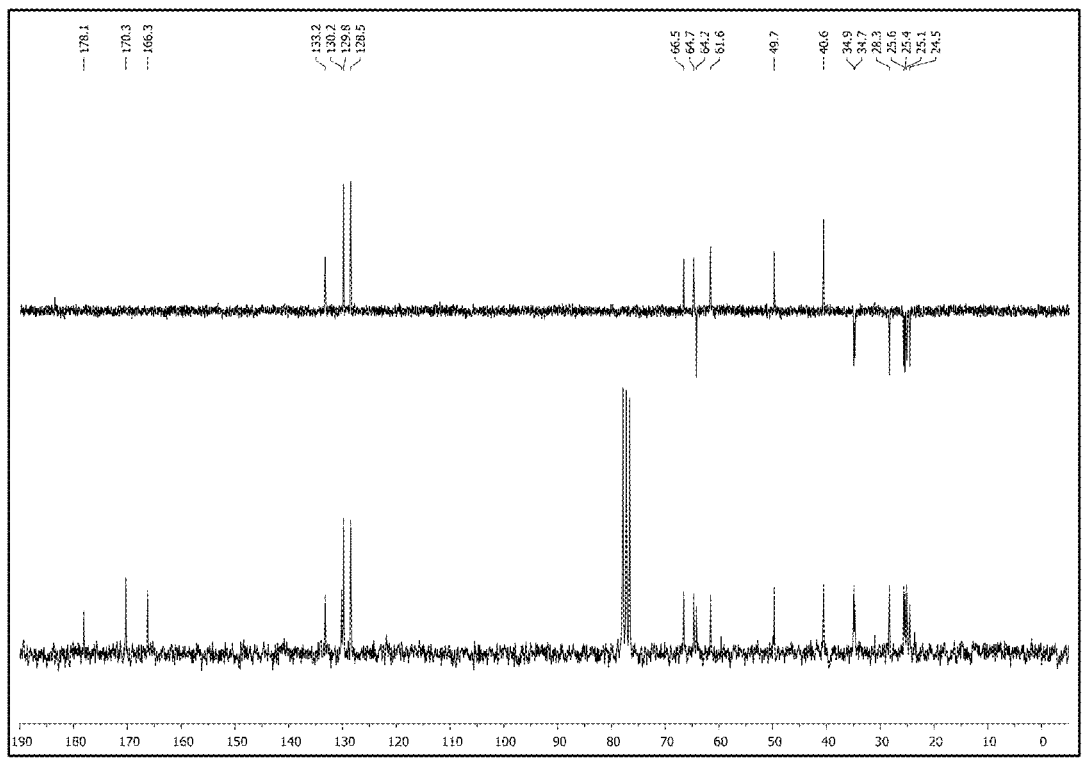
FIG. 26 presents the carbon nuclear magnetic resonance spectrum [$^{13}$C NMR; 50 MHz, CDCl$_3$] obtained for substance GNC.

The analyses of 13C NMR and DEPT-135 sub spectrum were also performed for hapten GNC (FIG. 26). In the region of aromatic carbons, only four signals related to benzyl ester were observed: 133.1, 130.5, 129.9 and 128.4 ppm, and only one of them did not appear in the DEPT-135 sub spectrum, thus demonstrating that the same was carbon bonded to the carboxyl substituent. The absence of more signals in the aromatic carbon region demonstrates that the benzyl protecting group has been actually removed, thus forming the products of interest.

The hapten GNE was obtained from the 2NBn hydrogenolysis reaction (Cai, X.; Whitfield, T.; Hixon, M. S.; Grant, Y.; Koob, G. F.; Janda, K. D. Probing active cocaine vaccination performance through catalytic and noncatalytic hapten design. J. Med. Chem. 2013, 56, pages 3701-3709). 1.35 g (2.7 mmol) of 2NBn were transferred to a stainless steel reactor along with 0.22 g of 10% Pd/C and 40 mL of ethyl acetate. The system was subjected to $H_2$ pressure (50 Kgf·cm$^{-2}$) and magnetic stirring for 96 hours at room temperature. Subsequently, the reaction was filtered in Celite for catalyst removal and the solvent was evaporated in a rotary evaporator under reduced pressure. 0.98 g of the desired product (89% yield) was obtained as a slightly yellowish solid.

The infrared spectrum obtained for hapten GNE (FIG. 21) has characteristic bands related to the amide C=O (1638 cm$^{-1}$) and ester (1716 cm$^{-1}$) stretchings. Two other important bands were observed: one at 1553 cm$^{-1}$ related to the asymmetric stretching of carboxylate group and the other at 3255 cm$^{-1}$ associated with the amine N—H binding.

In the $^1$H NMR spectrum for GNE, when compared with the 1H NMR spectrum of the 2NBn precursor, the absence of the characteristic signals of the benzyl group was observed. The multiplet centralized at 7.41 ppm, which was integrated for eight hydrogens, is now integrated for only 3 hydrogens. Additionally, the singlet at 5.10 ppm related to $H_{21}$, which was present in the 2NBn spectrum, disappeared in the GNE spectrum.

$^{13}$C NMR and DEPT-135 analyses were also performed for GNE. It was observed, in the region of aromatic carbons, four signals of the benzoyl group at 134.9, 130.9, 130.8 and 129.8 ppm, and only one of them did not appear in the DEPT-135. Three signs at 181.4, 173.1 and 166.8 ppm indicated the presence of the three carbonyls of the proposed structure, and eight inverted phase signals in DEPT-135 indicated the presence of the eight methylene carbons in the structure of the expected product.

Figure 29:
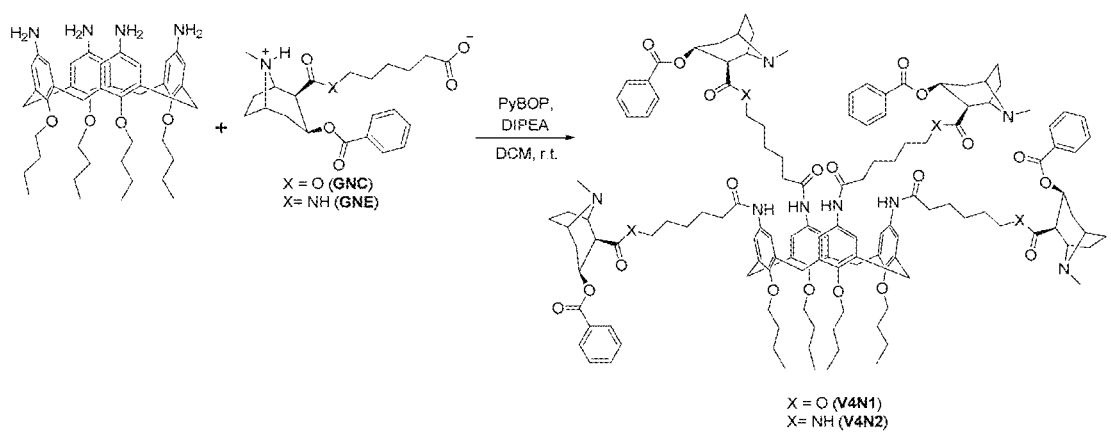
FIG. 29 presents the reaction scheme for obtaining substances V4N1 and V4N2.

For coupling the hapten GNC to calixarene 4NH and, therefore, obtaining the immunogen V4N1, the procedure was performed as represented in FIG. 29. In a round-bottom flask containing 0.29 g (0.72 mmol) of hapten GNC, 0.93 g (0.72 mmol), diisopropylethylamine (DIPEA) and 0.46 g (0.89 mmol) of (benzotriazol-1-yloxy)-tris(pyrrolidine)-phosphonium hexafluorophosphate (PyBOP) were added. Then, 5 mL of anhydrous DCM were added and the system was maintained under argon atmosphere and magnetic stirring for 40 minutes at room temperature. 0.11 g (0.15 mmol) of aminocalix[4]arene 4NH was added to another round-bottom flask, along with 7 mL of anhydrous DCM. After 10 minutes of magnetic stirring, the content was transferred to the first round-bottom flask, dropwise and under argon atmosphere. After 30 hours of magnetic stirring at room temperature, the reaction was ended and diluted to 80 mL of dichloromethane. Then, washes were performed using saturated solution of $NaHCO_3$ (2×25 mL) and distilled water (1×25 mL). After adding anhydrous sodium sulfate and filtering, the organic phase was evaporated using a rotary evaporator. Finally, purification was performed using column chromatography [7% methanol in $CHCl_3$+triethylamine drops], providing the desired product at 74% yield (0.25 g).

Figure 30:
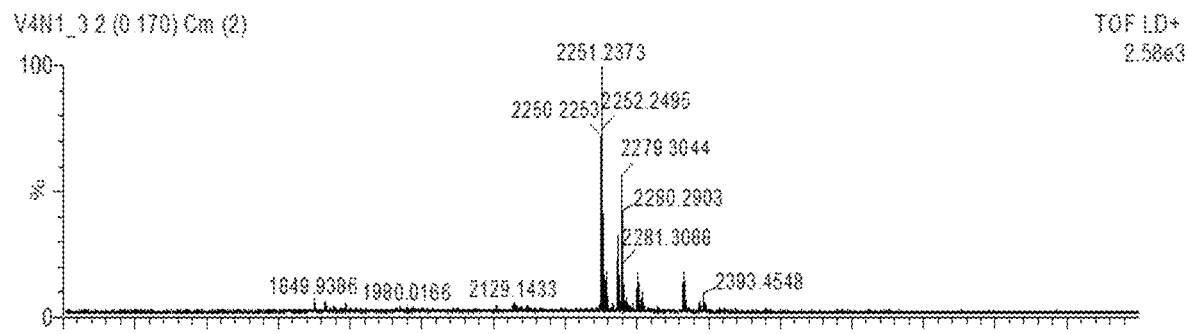
FIG. 30 presents the mass spectrum (MALDI-TOF) for substance V4N1.

MALDI-TOF mass spectrometry analysis (FIG. 30) showed the expected ion peak for the structure V4N1 [M+H$^+$](m/z) calculated 2,251.2278; obtained 2,251.2373.

Figure 22:
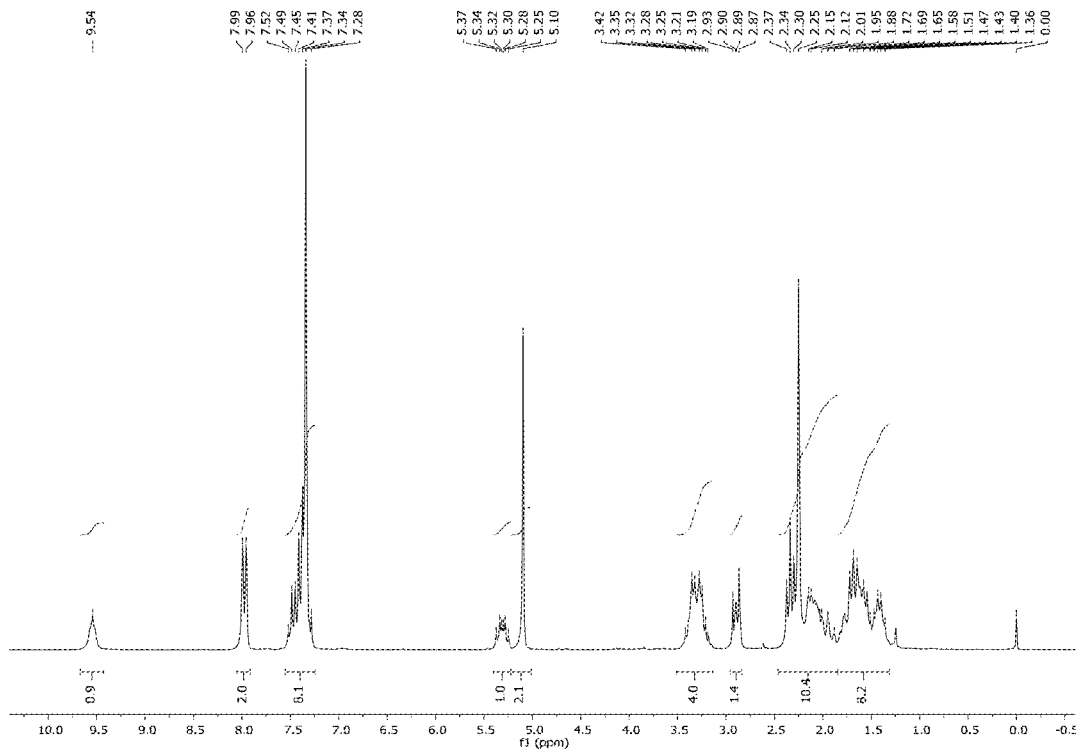
FIG. 22 presents the hydrogen nuclear magnetic resonance spectrum [$^1$H NMR; 200 MHz, CDCl$_3$] obtained for substance 2NBn.

For coupling the hapten GNE to calixarene 4NH and, therefore, obtaining the immunogen V4N2, the procedure was performed as represented in FIG. 22. The reactions of FIG. 22 were developed and adapted in the present invention and are reactions for forming amide bonds, based on Geraci, C.; Consoli, G. M. L.; Galante, E.; Bousquet, E.; Pappalardo, M.; Spadaro, A. Calix[4]arene decorated with four Tn Antigen Glycomimetic Units and P3CS Immunoadjuvant: synthesis, characterization, and Anticancer Immunological Evaluation. Bioconjugate Chem. 2008, 19, p.751-758. In a round-bottom flask containing 0.98 g (2.43 mmol) of hapten GNE, 0.31 g (2.43 mmol), of diisopropylethylamine (DIPEA) and 1.58 g (3.04 mmol) of (benzotriazol-1-yloxy)-tris(pyrrolidine)-phosphonium hexafluorophosphate (PyBOP) were added. Then, 8 mL of anhydrous DCM were added and the system remained under argon atmosphere and magnetic stirring for 40 minutes at room temperature. 0.32 g (0.45 mmol) of aminocalix[4]arene 4NH was added to another round-bottom flask, along with 10 mL of anhydrous DCM. After 10 minutes of magnetic stirring, the content was transferred to the first round-bottom flask, dropwise and under argon atmosphere. After 26 hours of magnetic stirring at room temperature, the reaction was ended and diluted to 80 mL of dichloromethane. Then, washes were performed using saturated solution of $NaHCO_3$ (2×25 mL) and distilled water (1×25 mL). After adding anhydrous sodium sulfate and filtering, the organic phase was evaporated using a rotary evaporator. Finally, purification was performed using column chromatography [7c methanol in $CHCl_3$+triethylamine drops], providing the desired product at 59% yield (0.60 g).

The infrared spectrum obtained for immunogen V4N2 had characteristic bands of C=O bond stretchings of ester (1716 cm$^{-1}$) and amide (1651 cm$^{-1}$). An intense band was verified at 1539 cm$^{-1}$ that can be related to the angular deformation of N—H amide bonds and at 1267 cm$^{-1}$, related to a band attributed to the C—O bond stretching of ester group.

The H NMR spectrum obtained for V4N2 is represented in FIG. 23. It is possible to verify in it the signal at 9.60 ppm related to the neighboring NH of $C_{17}$. Two doublets related to hydrogens $H_{7a}$ and $H_{7b}$, centered at 4.38 and 3.07 ppm, were respectively observed. The region of the signals of aromatic hydrogens includes the doublet at 7.97 ppm of $H_{29}$, the multiplet at 7.44-7.35 ppm (related to $H_{30}$ and $H_{31}$) and two broad signals at 6.75 and 6.75 ppm, probably of aromatic hydrogens $H_3$ of the calix[4]arene. Different signals were related to $H_3$ because the possibility of existing isomers is known due to the resonance of the neighboring amide group. At 5.31 ppm, integrated for four hydrogens, the double triplet related to $H_{21}$ was observed and, at 1.00 ppm, a triplet related to $H_{11}$ (integrated to 12) was observed.

Figure 24:
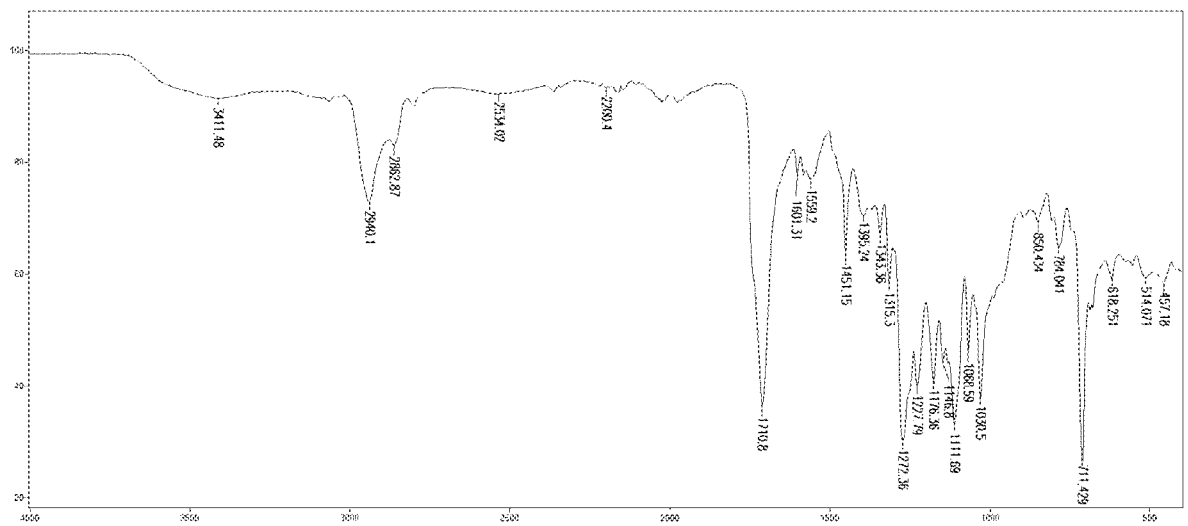
FIG. 24 presents the infrared spectrum obtained for substance GNC.
Figure 25:
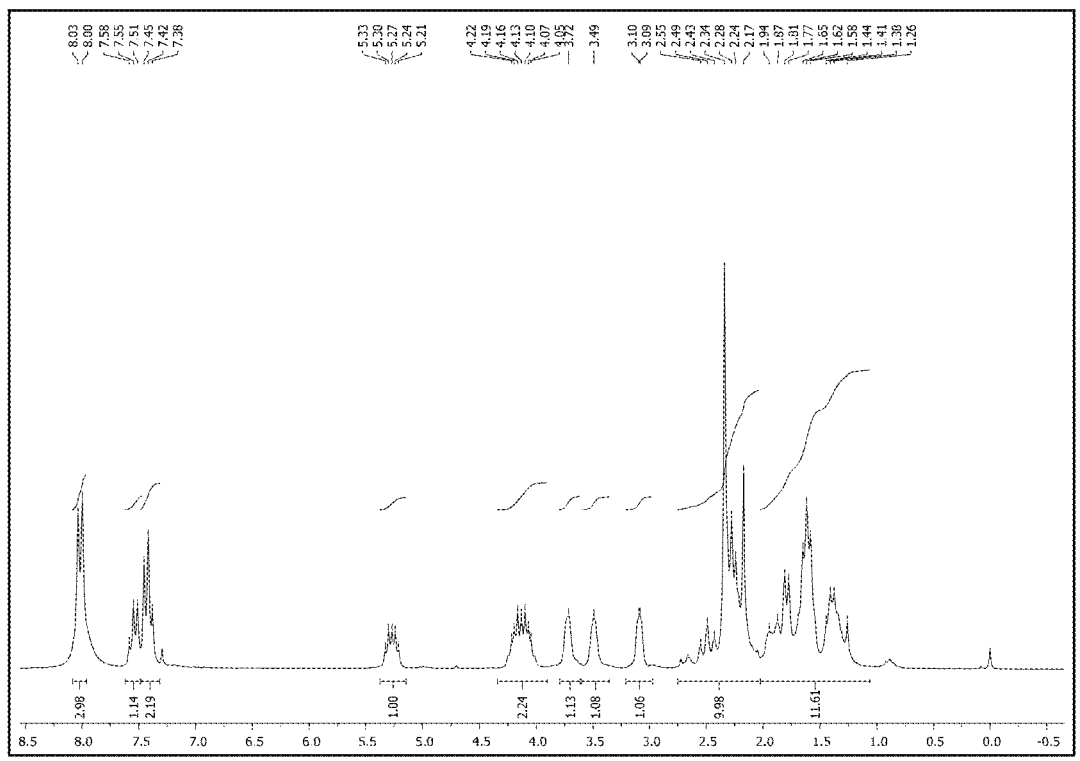
FIG. 25 presents the hydrogen nuclear magnetic resonance spectrum [$^1$H NMR; 200 MHz, CDCl$_3$] obtained for substance GNC.

The $^{13}$C NMR and DEPT-135 spectra for V4N2 are represented, respectively, in FIGS. 24 and 25. The analysis of both spectra allowed us to affirm that the reaction for preparing V4N2 was successfully performed. 29 distinct signals consistent with the proposed structure were observed in the $^{13}$C NMR spectrum, including eight signals in the aromatic region of the spectrum, three signs of carbonyls (at 171.5, 171.2 and 166.1 ppm) and 18 signals of aliphatic carbons. The hydrogenation pattern was verified by the analysis of the DEPT-135 spectrum and it was found that, of the 18 signals of aliphatic carbons, 12 are methylene carbons.

Figure 27:
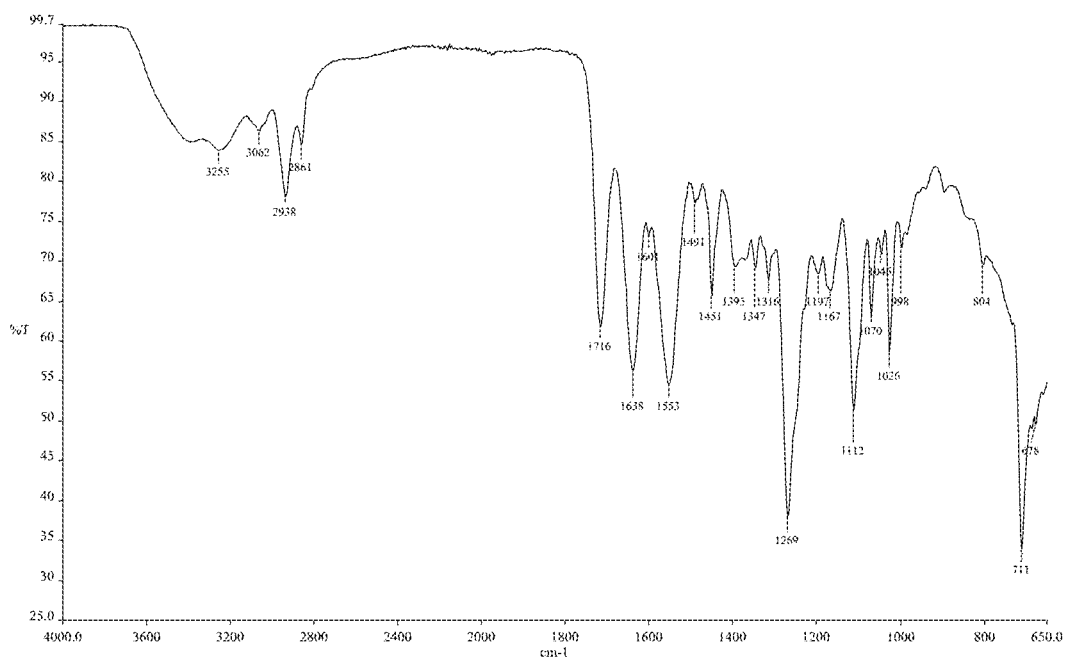
FIG. 27 presents the infrared spectrum obtained for substance GNE.

By means of the analysis of the HSQC contour map (FIG. 26), it was possible to assign some cross peaks, such as $C_3$ at 121.4 ppm, $C_{30}$ at 128.4 ppm, CA at 14.2 ppm, $C_{26}$ at 40.5 ppm, $C_{21}$ at 66.2 ppm and $C_7$ at 31.1 ppm, among others. The analysis of the MALDI-TOF mass spectrum (FIG. 27) showed the peak of the expected ion for the V4N2 structure [M+H]$^+$ (m/z) calculated 2,247.2917; obtained 2,247.2908].

Example 2—Synthesis of the Immunogen V8N2

The immunogens V8N1 and V8N2 were prepared by the coupling reaction between calixarene 8NH and haptens GNC and GNE, respectively, as represented in FIG. 2.

Calix[n]arene 8NH was prepared in four stages, from the p-terc-butylphenol, as represented in FIG. 3.

Figure 33:
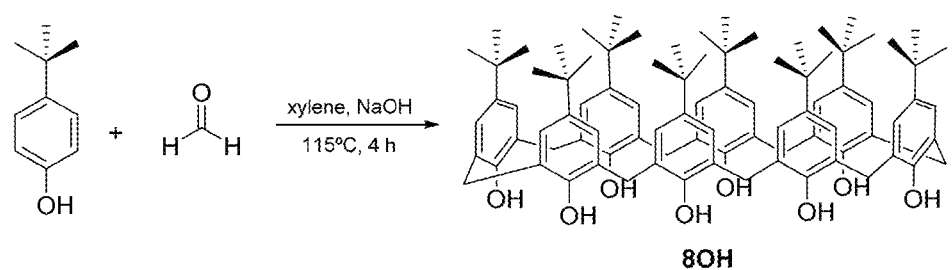
FIG. 33 presents the reaction scheme for obtaining substance 8OH.

The substance 8OH was obtained from the cyclocondensation reaction of p-terc-butylphenol with paraformaldehyde, as represented in FIG. 33 (Gutsche, C. D.; Dhawan, B.; No, K. H.; Muthukrishnan, R. The synthesis, Characterization, and Properties of the Calixarenes from p-tert-butylphenol. J. Am. Chem. Soc. 1981, 103, p.3782-3792). In a 1 L three-neck round-bottom flask containing a magnetic stirrer and adapted for the input of a continuous nitrogen flow, 10 g of p-tert-butylphenol (66.5 mmol), 3.6 g paraformaldehyde (120 mmol), 1.5 mL of a 10 mol/L sodium hydroxide solution and 300 mL of xylene were added. The formed heterogeneous mixture was mechanically stirred for approximately 15 minutes. Subsequently, the round-bottom flask was coupled to a Dean-Stark apparatus (containing 100 mL of xylene) and a ball condenser. The reaction was submitted to reflux at 115° C., with continuous nitrogen flow for approximately 4 hours. After 30 minutes of heating, the reaction became a homogeneous mixture, and after 1 hour, a white precipitate began to form. The mixture was cooled at room temperature and the precipitate formed was collected by filtration. The precipitate was washed successively with portions of 200 mL of toluene, 200 mL of ethyl ether, 200 mL of acetone and finally with 200 mL of distilled water. Subsequently, the filtrate was dried in a rotary evaporator under reduced pressure. At the end of the process, the solid obtained was dissolved in 800 mL of chloroform and was heated until its volume was reduced to 600 mL. The solution was then cooled at room temperature and the formed precipitate was then collected and dried in a high vacuum pump, providing the 8OH product as a white solid with 52% yield.

The infrared spectrum obtained for the substance 8OH presents a broad band at 3225 cm$^{-1}$, which is characteristic of O—H bond stretchings. Bands at 1602, 1486 and 1452 cm$^{-1}$ refer to C=C stretchings of the aromatic rings. The band at 1203 cm$^{-1}$ is characteristic of stretchings of C—O bonds in combination with the angular deformations of O—H bonds. Two related absorption bands were observed at 1391 and 1361 cm$^{-1}$, due to the angular deformations of C—H bonds of the tert-butyl groups.

In the $^1$H NMR spectrum of the substance 8OH, represented in FIG. 34, a singlet is observed at 1.26 ppm related to the 72 hydrogens of —CH$_3$ groups of the tert-butyl substituents (HE). Two doublets are centered at 3.50 and 4.37 ppm attributed to methylene hydrogens located between the aromatic rings: H$_{7a}$ and H$_{7b}$.

The presence of four signals in the aromatic carbons region is observed in the $^{13}$C NMR spectrum of 8OH, which is consistent with the structure proposed for the substance. At 31.4 ppm the intense signal for hydrogens of the groups —CH$_3$ of the tert-butyl substituents is found.

Figure 35:
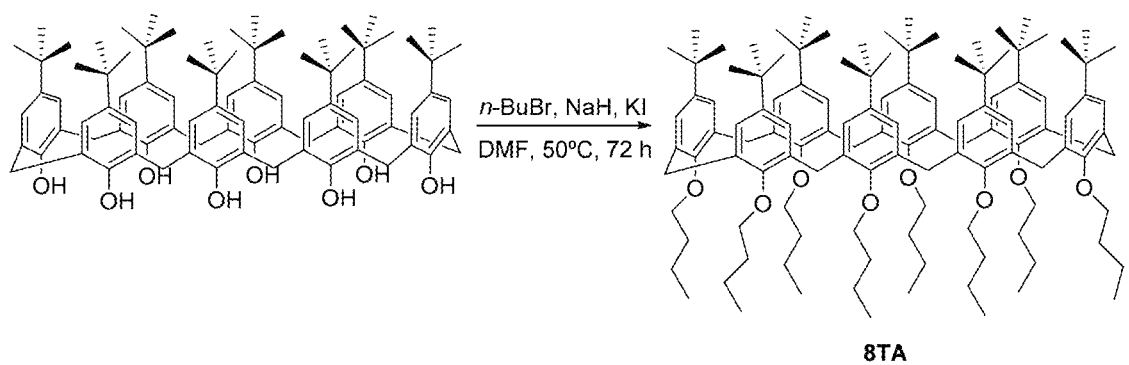
FIG. 35 presents the reaction scheme for obtaining substance 8TA.

The substance 8TA was obtained from O-alkylation of 8OH, as represented in FIG. 35 (Modified from Yi, J.; Tang, K.; Huang, S. Synthesis of p-tert-butylcalix[8]arene ether derivatives. Indian Journal of Chemistry. 2008, 47B, p.1435-1437). In a 500 mL round-bottom flask containing a magnetic stirrer and coupled to a vent, 1 g (0.77 mmol) of p-tert-butilcalix[8]arene (8OH) and 150 mL of dimethylformamide were added. The mixture was heated to 70° C. until a translucent solution was obtained. After this point, 6 g of NaH were added. The mixture remained under stirring at 60° C. for approximately 30 minutes. Subsequently, 50 mL of n-bromobutane (77 mmol) and 5 g potassium iodide (30 mmol) were added to the mixture. The temperature was decreased to 50° C. and the reaction remained under stirring for 72 hours. After this time, 100 mL of dichloromethane were added. This organic phase was washed with 200 mL of acid solution of 0.1 mol L$^{-1}$. The organic phase was separated from the aqueous phase and taken to the rotary evaporator at reduced pressure until half the amount of solvent added was evaporated. Subsequently, 200 mL of acetone was added and the mixture was again taken to the rotary evaporator and remained under low pressure until observing the formation of an off-white precipitate. The precipitate was recovered and washed with acetone, providing a white solid with 80% yield.

In the infrared spectrum obtained for substance 8TA, it is possible to verify the disappearance of the band of O—H bond stretchings at 3225 cm$^{-1}$, when compared with the spectrum of the precursor substance. Stretching bands of C—H bonds from the tert-butyl groups could be identified at 2955 and 2868 cm$^{-1}$. Characteristic bands of angular deformation of tert-butyl groups appeared at 1381 and 1360 cm$^{-1}$. An intense band was observed at the frequency of 1190 cm$^{-1}$, characteristic of C—O bond stretchings.

Figure 36:
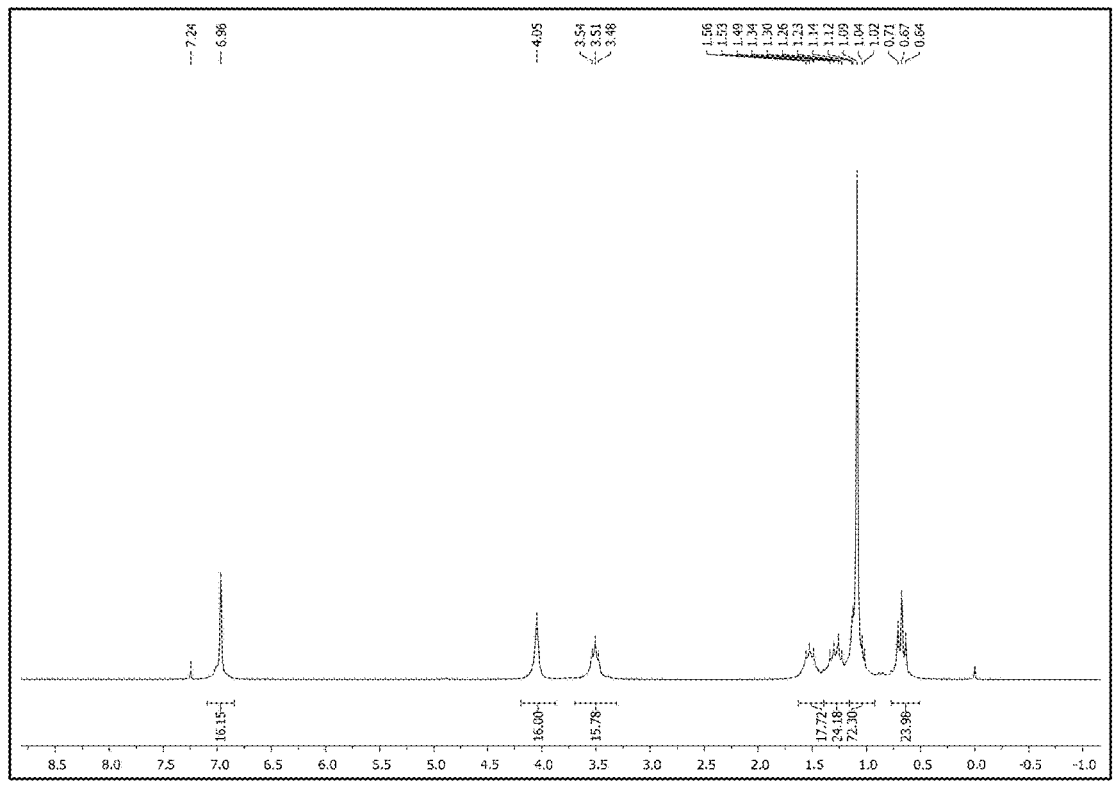
FIG. 36 presents the hydrogen nuclear magnetic resonance spectrum [$^1$H NMR; 200 MHz, CDCl$_3$] obtained for substance 8TA.

The $^1$H NMR spectrum of substance 8TA is represented in FIG. 36. It is observed at 0.67 ppm a triplet attributed to H: hydrogens. A singlet at 1.09 ppm, integrated for 72 hydrogens, is related to the H$_6$ hydrogen nucleus. Diastereotopic hydrogens, H$_a$ and H$_{7b}$, are presented as a singlet at 4.05 ppm. In the region of aromatic hydrogens, there is a singlet at 6.96 ppm related to H$_3$.

In the $^{13}$C NMR and DEPT-135 spectra of substance 8TA, it is possible to determine the signals related to carbons C$_6$ and C$_5$ of tert-butyl substituent: at 31.6 ppm and 34.4 ppm, respectively. In addition, the signals of the four carbons of n-butyl groups were identified, among them, the signal of Cu at 14.0 ppm.

Figure 37:
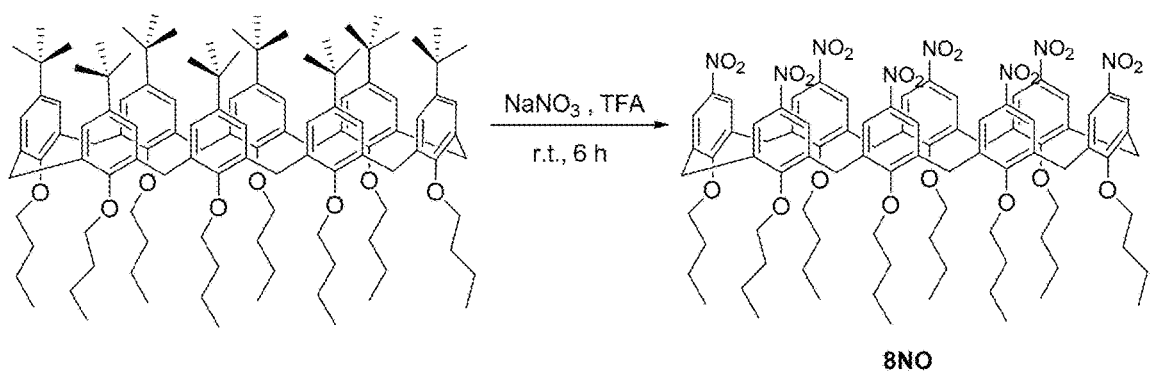
FIG. 37 presents the reaction scheme for obtaining substance 8NO.

The substance 8NO was obtained from the ipso-nitration of 8TA, as represented in FIG. 37 (Modified from Dudic, M.; Colombo, A.; Sansone, F.; Casnate, A.; Donofrio, G.; Ungaro, R. A general synthesis of water soluble upper rim calix[n]arene guanidinium derivatives which bind to plasmid DNA. Tetrahedron. 2004, 60. pages 11613-11618). In a round-bottom flask containing a magnetic stirrer, 500 mg of 8TA (0.385 mmol), 2.60 g of NaNO$_3$ (30.5 mmol) and 2.4 mL of trifluoroacetic acid (TFA) (30.5 mmol) were added. After adding TFA, dropwise, the round-bottom flask was capped with a glass cover and the mixture was kept under stirring for approximately six hours. For the preparation, the mixture thus formed was poured into 200 mL of iced water, a procedure in which the precipitation of the impure product was observed. The precipitate was filtered and washed with 50 mL of distilled water and 50 mL of methanol, and dried in a high vacuum pump. Subsequently, the precipitate was solubilized in 8 mL of distilled ethyl acetate and then another 20 mL of methanol were added. After 24 hours of recrystallization, there was precipitation of a light pink solid as the pure form of the 8NO product with 64"% yield.

The spectrum in the infrared region obtained for substance 8NO presents characteristic bands of asymmetric and symmetrical stretching of the —$NO_2$ groups, respectively, at 1518 and 1340 $cm^{-1}$. It was also possible to observe the carbon C—H stretching bands of $sp^3$ carbon at 2956 and 2872 $cm^{-1}$ and the C—O—C stretching at 1232 $cm^{-1}$.

Figure 38:
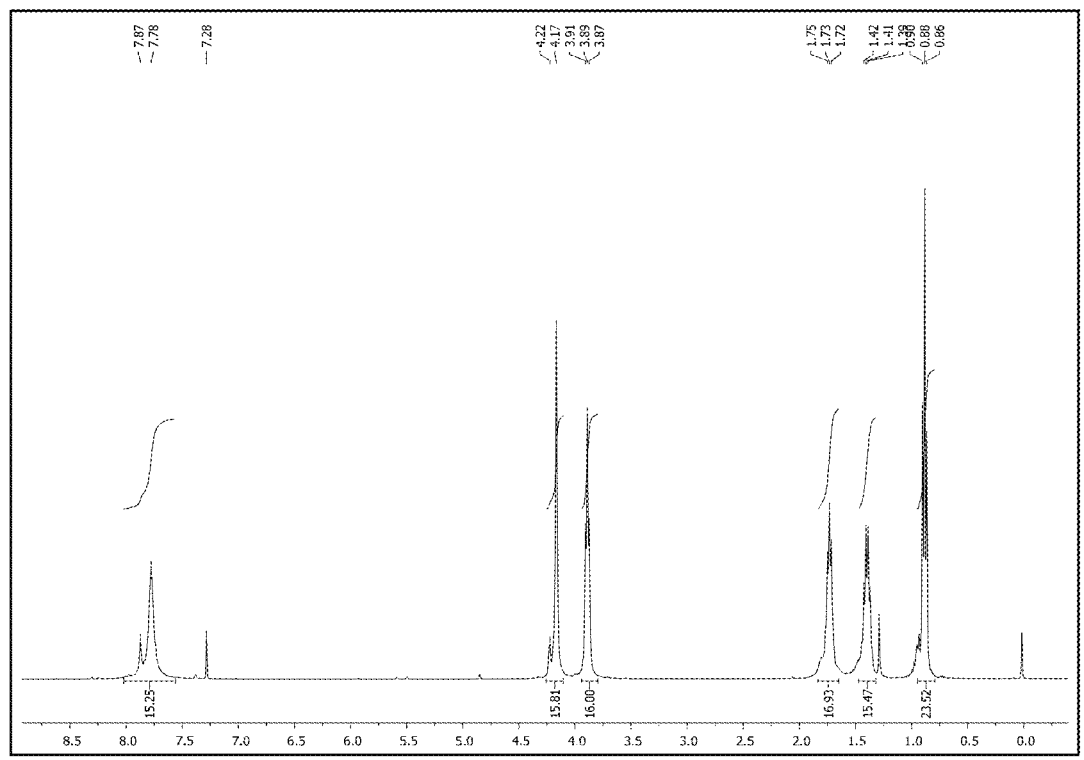
FIG. 38 presents the hydrogen nuclear magnetic resonance spectrum [$^1$H NMR; 200 MHz, CDCl$_3$] obtained for substance 8NO.

It is observed, in the $^1H$ NMR spectrum of substance 8NO, represented in FIG. 38, that the signal related to aromatic hydrogens ($H_3$) is found in a region of the most unshielded spectrum (7.78 ppm), when compared to the 8TA precursor. The other signals present in the spectrum were attributed to methylene hydrogens: $H_{7a}$ and $H_{7b}$, at 4.17 ppm and aliphatic hydrogens: $H_8$: 3.89 ppm; $H_9$: between 1.72-1.75 ppm; $H_{10}$: between 1.39-1.42 ppm and $H_{11}$: 0.88 ppm.

In the $^{13}C$ NMR and DEPT-135 spectra of substance 8NO, four signals are observed in the region of aromatic carbons. By the analysis of the DEPT-135 spectrum only one of them, at 124.8 ppm, is hydrogenated.

Figure 39:
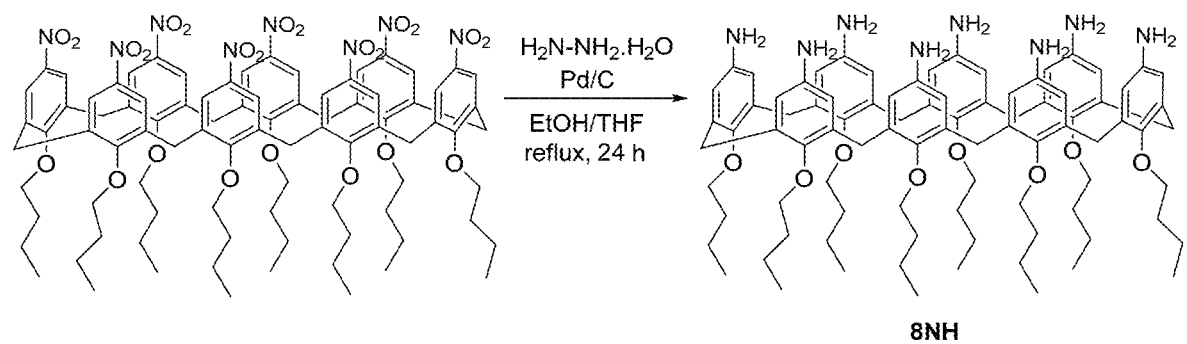
FIG. 39 presents the reaction scheme for obtaining substance 8NH.

The substance 8NH was obtained from 8NO reduction, as represented in FIG. 39 (modified from Podoprygorina, G.; Zhang., J.; Bolte., M.; Janshoff, A.; Bohmer, V. Supramolecular structures formed by calix[8]arene derivatives. *Org. Lett.* 2003, 5(26), pages 5071-5074). In a round-bottom flask containing a magnetic stirrer, 100 mg of 8NO (0.06 mmol), 20 mL of ethanol/THF (1:1; v/v), 5 mL of hydrazine $NH_2NH_2 \cdot H_2O$ (80%) and 20 mg of Pd/C (10%) were added. The mixture remained under stirring and reflux for 24 hours. After this period, the mixture was submitted to a vacuum filtration with quantitative filter paper to remove Pd/C (10%) from the reactionary medium, and was subsequently washed with a mixture of 40 mL of acidified methanol. The filtrate was then concentrated in a rotary evaporator until its solvent volume was halved. Subsequently, 50 mL of distilled water were added and, from there, the formation of a white precipitate was observed, that was filtered, washed with distilled water and dried in a high vacuum pump, providing the 8NH product with 85% yield.

The infrared spectrum obtained for substance 8NH features characteristic bands at 3358 $cm^{-1}$, possibly associated with N—H stretchings of aromatic primary amines as well as bands at 2955, 2930 and 2868 $cm^{-1}$, which are associated with $sp^3$ carbon C—H stretching.

Figure 40:
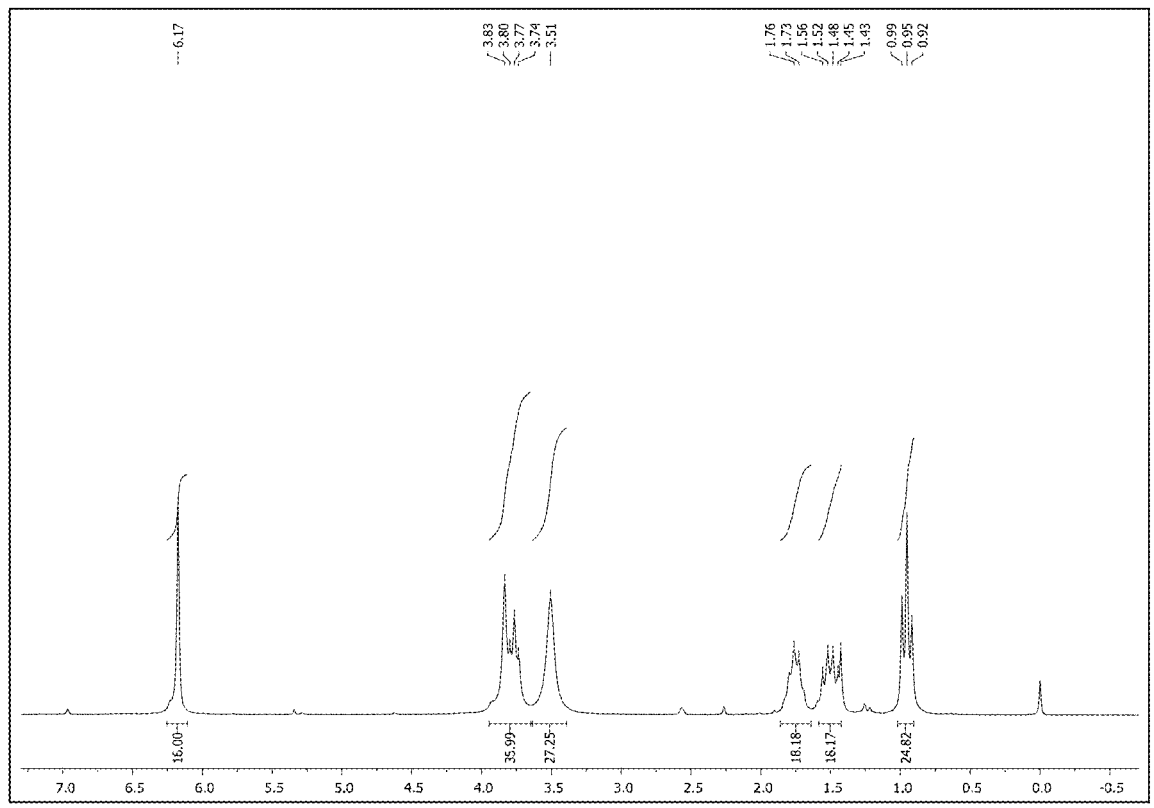
FIG. 40 presents the hydrogen nuclear magnetic resonance spectrum [$^1$H NMR; 200 MHz, CDCl$_3$] obtained for substance 8NH.

In the 1H NMR spectrum of substance 8NH, represented in FIG. 40, a singlet is observed at 6.17 ppm related to the 16 aromatic hydrogens. The signal for the hydrogens of the methylene bridge ($H_{7a}$ and $H_{7b}$), appears as a singlet located at 3.83 ppm and overlaps with the $H_{11}$ signal, which is a triplet located at 3.77 ppm.

In the $^{13}C$ NMR spectrum of substance 8NH, there is a change in the value of chemical shifts of aromatic carbons, especially carbon $C_3$. The amino group increases the electronic density in $C_3$ carbon due to the resonance effect of the non-bonding nitrogen electron pair and the aromatic ring and, for this reason, the signal related to $C_3$ is observed at 115.2 ppm for 8NH.

The procedures for obtaining GNC and GNE haptens were described earlier in example 1.

Figure 41:
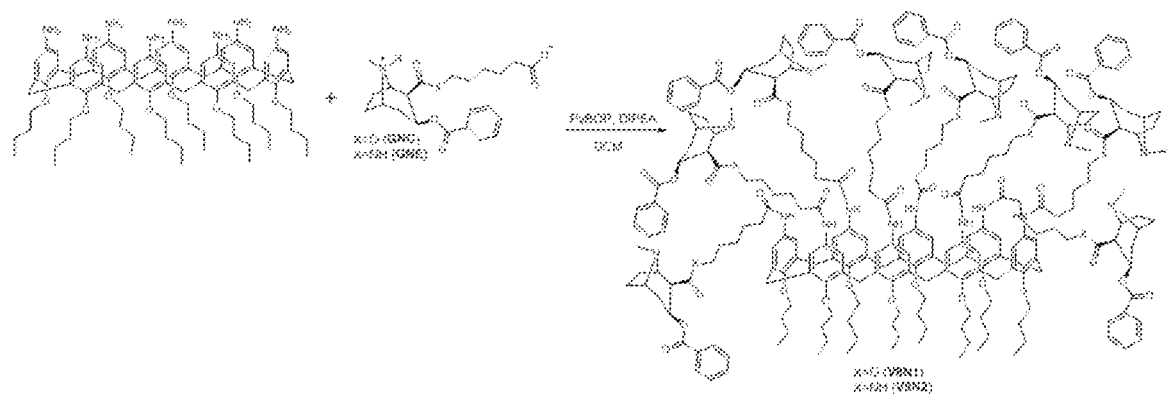
FIG. 41 presents the reaction scheme for obtaining substances V8N1 and V8N2.

For coupling the hapten GNC to calixarene 8NH and, therefore, obtaining the immunogen V8N2, the procedure was performed as represented in FIG. 41. In a round-bottom flask with a magnetic stirrer, 0.433 g (1.08 mmol) of hapten GNC, 300 μL of diisopropylethylamine (DIPEA), 0.700 g (1.34 mmol) of (benzotriazol-1-yloxy)-tris(pyrrolidine)-phosphonium hexafluorophosphate (PyBOP) and 10 mL of anhydrous DCM were added using a syringe. The reaction mixture was kept under stirring for approximately 30 minutes under argon atmosphere. In another round-bottom flask, 0.100 g (0.07 mmol) of 8NH and mL of anhydrous DCM were added, and, under argon atmosphere, the mixture was kept under stirring for 10 minutes. Through a cannula and argon balloons, the mixture of 8NH and anhydrous DCM was transferred, dropwise, to the balloon containing hapten GNC, PyBOP coupling reagent and the DIPEA base. This final mixture was kept under stirring for 48 hours. After this time, the mixture was subjected to two purifications, one using a Sephadex LH-20 column (in $CH_2Cl_2$) and another using a silica-gel column using a chloroform:methanol: triethylamine mixture as eluent (95:4:1 v/v). Through this procedure, a yellowish and crystalline solid was obtained as the V8N1 product with 51% yield.

Figure 42:
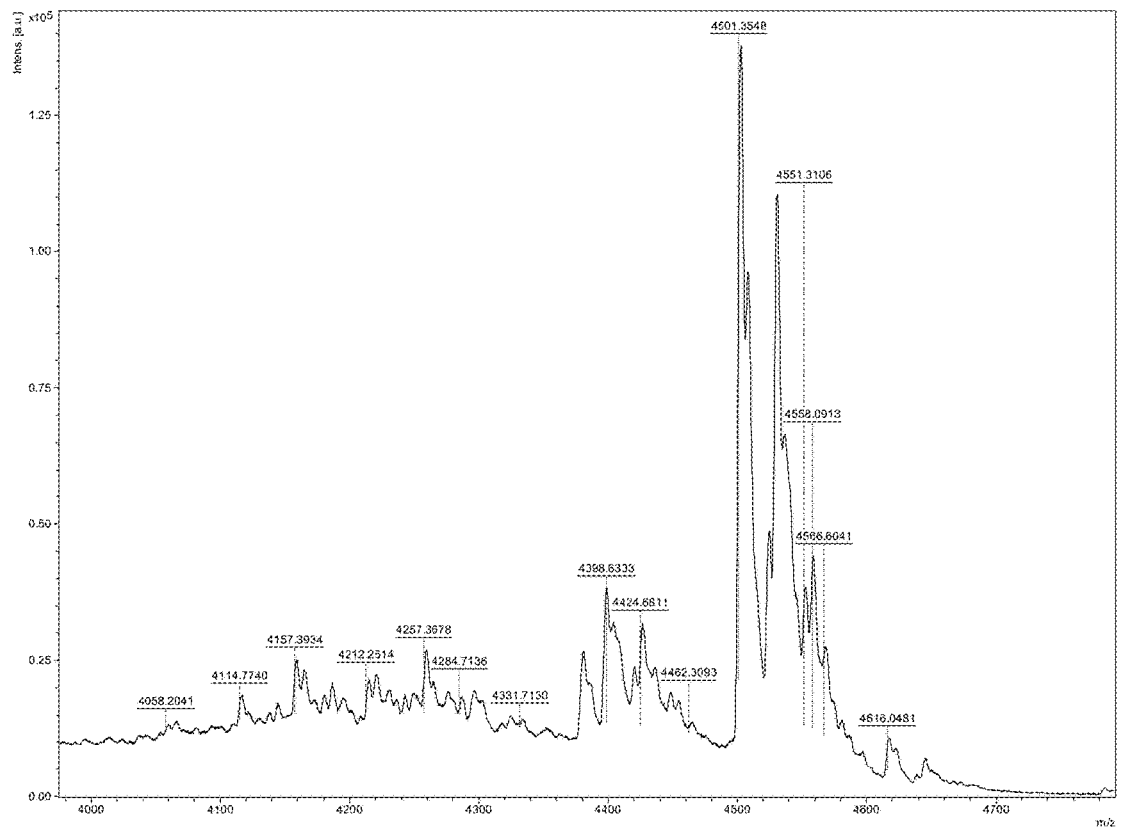
FIG. 42 presents the mass spectrum (MALDI-TOF) for substance V8N1.

MALDI-TOF mass spectrometry analysis (FIG. 42) showed the expected ion peak for the structure V8N1 $[M+H]^+$ (m/z) calculated 4,501.5790; obtained 4,501.3548].

For coupling the hapten GNE to calixarene 8NH and, therefore, obtaining the immunogen V8N2, the procedure was performed as represented in FIG. 41. In a round-bottom flask with a magnetic stirrer, 0.433 g (1.08 mmol) of hapten GNE, 300 μL of diisopropylethylamine (DIPEA), 0.700 g (1.34 mmol) of (benzotriazol-1-yloxy)-tris(pyrrolidine)-phosphonium hexafluorophosphate (PyBOP) and 10 mL of anhydrous DCM were added using a syringe. The reaction mixture was kept under stirring for approximately 30 minutes under argon atmosphere. In another round-bottom flask, 0.100 g (0.07 mmol) of 8NH and mL of anhydrous DCM were added, and, under argon atmosphere, the mixture was kept under stirring for 10 minutes. Then, the transfer of this mixture was carried out, dropwise, to the round-bottom flask containing the hapten GNE, PyBOP coupling reagent and DIPEA base. After 48 hours under stirring, the mixture was subjected to two purifications, one using a Sephadex LH-20 column (in $CH_2Cl_2$) and another using a silica-gel column using a chloroform:methanol:triethylamine mixture as eluent (94:5:1 v/v). Through these procedures, a yellowish and crystalline solid was obtained as the desired product V8N2 with 60% yield.

Figure 43:
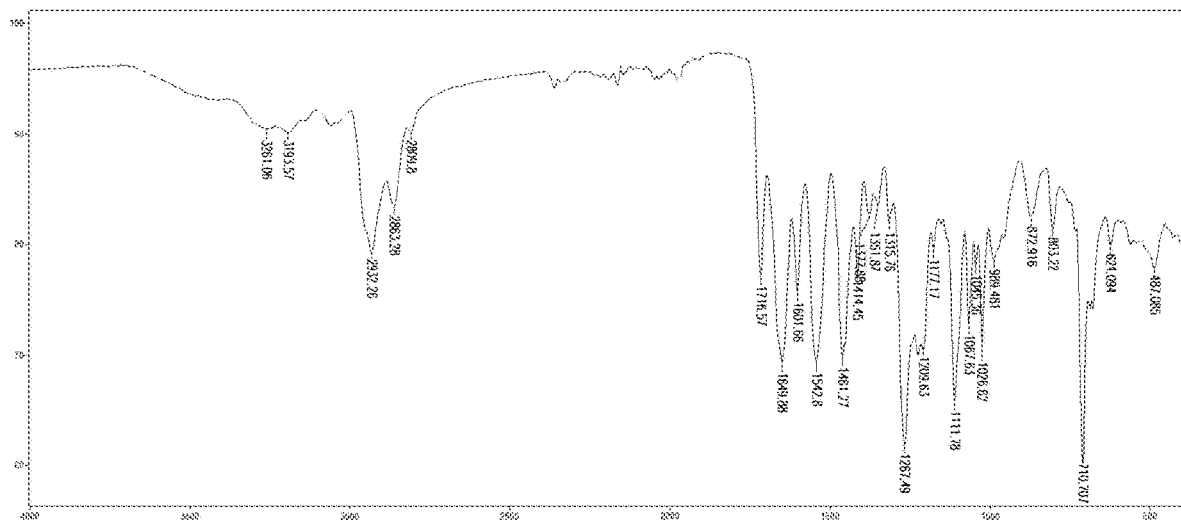
FIG. 43 presents the infrared spectrum obtained for substance V8N2.

In the infrared region spectrum obtained for substance V8N2, represented in FIG. 43, bands were observed at 1711 and 1649 $cm^{-1}$, which refer to carbonyls stretching. At 2932 and 2863 $cm^{-1}$, bands related to the stretching of C—H bonds of the aromatic rings appear. The band at 1267 $cm^{-1}$ refers to the C—O bond of the alkaloid benzyl ester.

Figure 44:
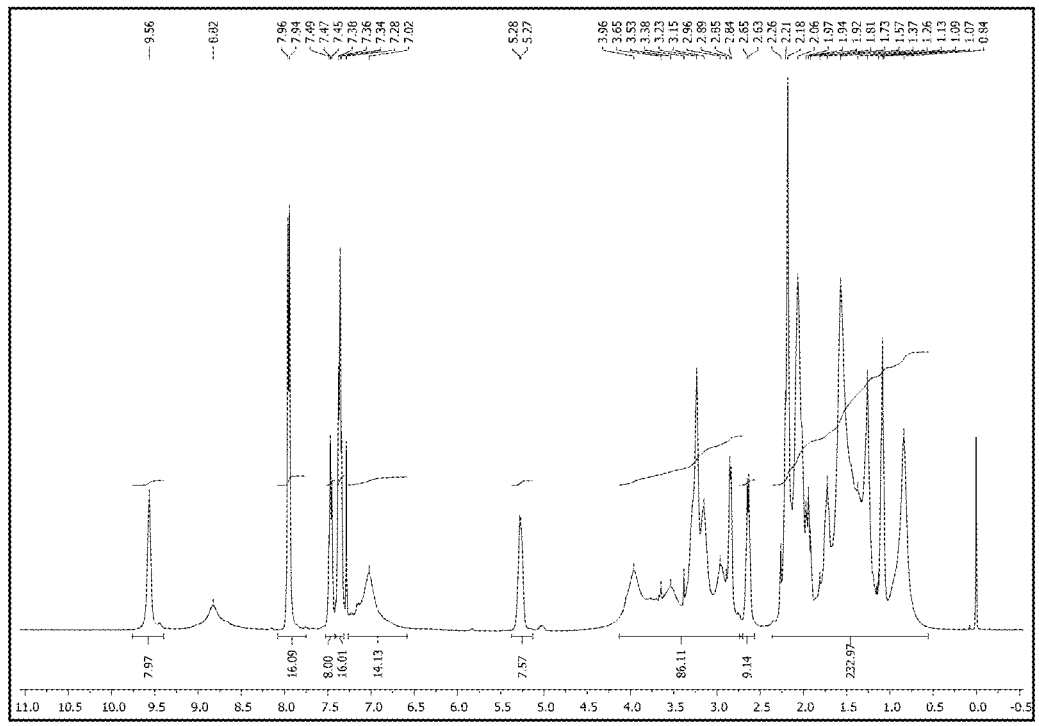
FIG. 44 presents the hydrogen nuclear magnetic resonance spectrum [$^1$H NMR; 400 MHz, CDCl$_3$] obtained for substance V8N2.

In the $^1H$ NMR spectrum of substance V8N2, represented in FIG. 44, a triplet is observed at 1.08 ppm related to hydrogens $H_{11}$ of the calix[8]arene macrocycle and the singlet, at 3.23 ppm, related to the hydrogens of the methylene bridge of the calix[8] are macrocycle, $H_{7a}$ and $H_{7b}$. A triplet was observed centered at 9.56 ppm, related to the neighboring N—H of carbon $C_{15}$. In the region of aromatic hydrogens signals, characteristic signs of hapten GNE appeared, a dublet at 7.95 ppm related to $H_{29}$, a triplet at 7.47 ppm related to $H_3$, and a triplet at 7.35 ppm related to $H_{30}$. Still in the region of aromatic hydrogens, a broad signal centered at 7.02 ppm refers to the hydrogens of the aromatic rings of calix[8]arene, $H_3$. A broad sign for 8H, between 5.27-5.28 ppm, refers to the hydrogen of the tropane moiety, $H_{21}$. The intense singlet at 2.18 ppm refers to methyl hydrogens linked to the bicycle's nitrogen, $H_{26}$.

Figure 45:
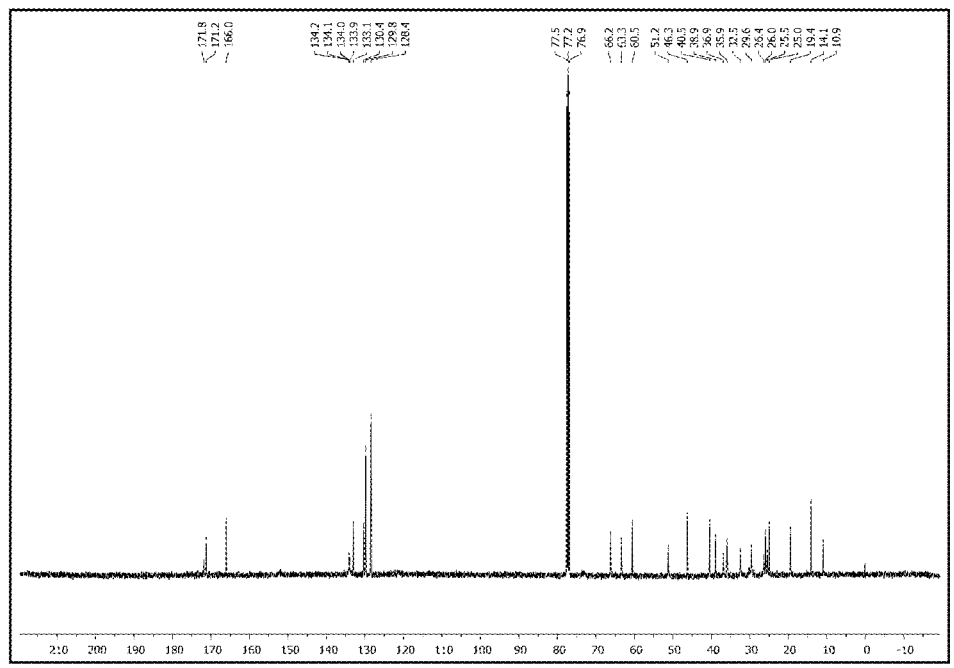
FIG. 45 presents the carbon nuclear magnetic resonance spectrum [HC NMR; 100 MHz, CDCl$_3$] obtained for substance V8N2.

In the $^{13}C$ NMR spectrum of the substance V8N2, represented in FIG. 45, different signs consistent with the proposed structure are noted, among them, 3 signals in the carbonyl region: 166.0; 171.2 and 171.8 ppm: $C_{27}$, $C_{18}$ and $C_{12}$, respectively.

Figure 46:
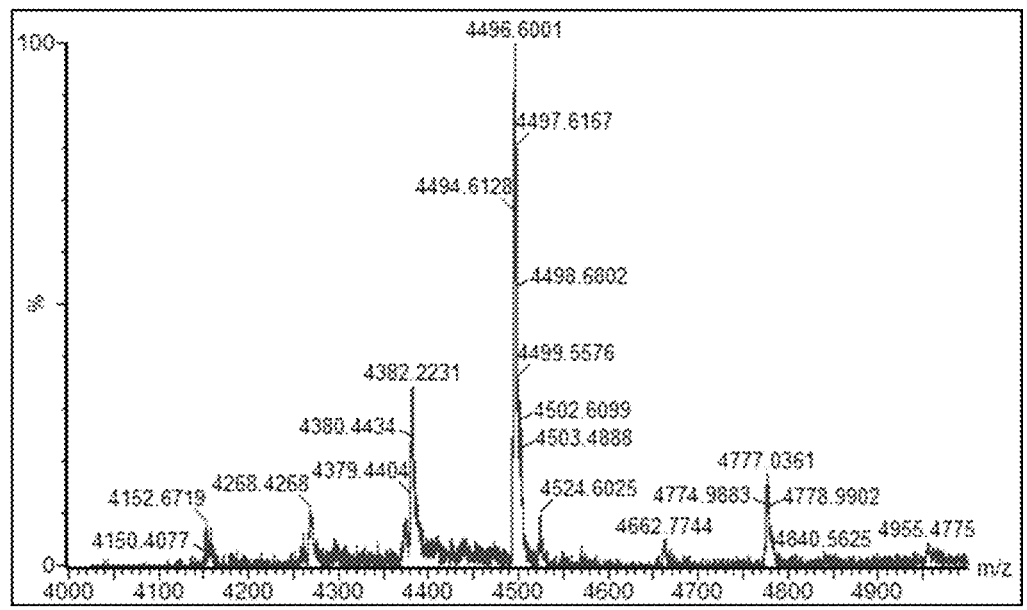
FIG. 46 presents the mass spectrum (MALDI-TOF) for substance V8N2.

The analysis of the mass spectrum (MALDI-TOF) obtained, represented in FIG. 46, showed the peak of the expected ion for the V8N2 structure $[M+H]^+$ (m/z) calculated 4,494.7009; obtained 4,494.6128].

Example 3—Evaluation of Immune Stimulation Capacity for Producing Anti-Cocaine Antibodies To assess the immune stimulation capacity for the production of anti-cocaine antibodies, an experiment of active immunization of mice was carried out. This experiment assessed the ability of the V4N2 molecule to produce anti-cocaine antibodies and the best dose of the molecule to be inoculated for the production of antibodies. Freund's adjuvant was used as a negative comparator and the GNE linked to KLH (KLH-GNE) was used as a positive comparator, as previously described (Wirsching, P.; Janda, K. D. U.S. Pat. No. 6,383,490 B1 2002, Anti-cocaine vaccine).

All animal experiments were carried out following the best management and experimentation practices. The animals used were kept in the bioterium with a 12-hour light cycle at 21° C. with food and water ad libitum. Five groups each composed of 12 Balb-C mice (UFMG Central Bioterium, Brazil) were immunized at 0, 7, 21 and 42 days. On day 0, a volume of 300 microliters of a treatment solution tested in complete Freund adjuvant (Sigma, USA) was inoculated. In the other times, the same volume of a solution composed of the treatment tested and Freund's incomplete adjuvant (Sigma, USA) was inoculated. The groups received the following treatments: 1. Freund's Adjuvant; 2. KLH+GNE; 3. V4N2 30 nM; 4. V4N2 3,0 µM; 5. V4N2 300 µM; 6. V8N2 30 nM; 7. V8N2 3,0 µM; 8. V8N2 300 µM. After anesthesia with a 15 mg $kg^{-1}$ xylazine and 150 mg $kg^{-1}$ ketamine solution, injected intraperitoneally (I.P.), 0.2 mg of blood was collected through the submandibular vein and the treatment was injected I.P. Blood was immediately centrifuged at 4° C. and the plasma was segregated and stored at −80° C. until the analysis.

Anti-cocaine antibody titers were dosed using the enzyme immunoabsorption technique (ELISA), using a technique previously described by Fetissov (Fetissov, S. O. Neuropeptide autoantibodies assay. Methods Mol Biol. 2011; 789: 295-302). On the first day, cocaine fixation was carried out by incubation of 100 microliters of solution of the drug in fixation buffer (0.05 bicarbonate, pH 9.6 with $2 \times 10^{-4}$ g mL-sodium azide) for 12 hours at 4° C. on a plate with 96 micro wells (Maxis orb™ Thermo Fisher Scientific, MA, USA). On the second day, 10 plasma microliters of each sample were diluted in 2 mL of sample buffer (PBS with $2 \times 10^{-4}$ g $mL^-$ sodium azide). The plate was washed 3 times with washing buffer (PBS with Tween 20 (Sigma, USA) at 0.05). Then, 100 microliters of each sample were incubated in duplicate. The plate was incubated for 12 hours at 4° C. On the third day, the plate was washed 3 times with washing buffer and 100 microliters were incubated in a solution of 0.5 microliter of antibodies per mL of sample buffer for 3 hours at 37° C. Antibodies linked to anti-IgG (Anti-Mouse IgG (Fab specific) Alkaline phosphatase, produced in goat, Sigma, USA) and anti-IgM (Anti-Mouse IgG (µ-chain specific) alkaline phosphatase, produced in goat, Sigma, USA) alkaline phosphatase were used. After incubation, the plate was washed 3 times with a washing buffer, 100 microliters of a revealing solution (paranitrophenyl 1 mg $mL^{-1}$, 0.2 M Tris buffer, Sigmafast® p-nitrophenyl phosphate, Sigma, USA), in each well for 40 minutes at room temperature and protected from light. After incubation, 50 microliters of NaOH 3 N were placed in each plate well to stop the reaction. The reading was made by absorbance (optical density) using an automated reader VICTOR Multilabel Plate Reader (PerkinElmer, Wellesley, MA, USA), with 405 nm filter.

Figure 47:
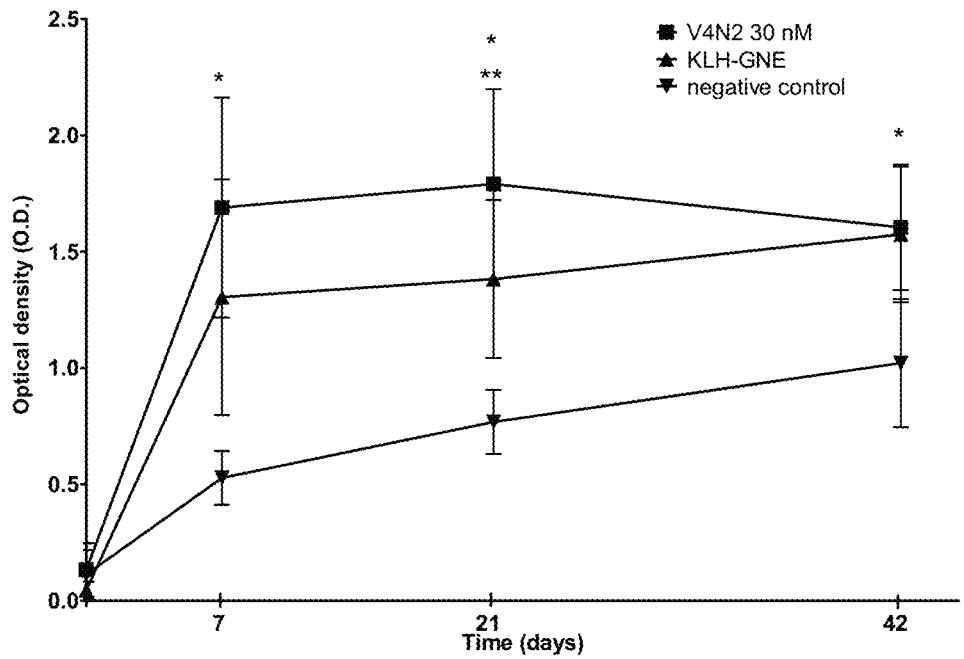
FIG. 47 presents the production of IgG-type anti-cocaine antibodies, measured by ELISA, of the negative and positive control groups and of substance V4N2 at a dose of 30 nM. The anticocaine IgG concentration is significantly higher than the negative control group from the seventh to $42^{nd}$ day after the start of vaccination. *$p \leq 0.001$ V4N2 versus negative control; **$p \leq 0.01$ V4N2 versus KLH+GNE; ANOVA, Bonferroni test.

It is observed in FIG. 47 that treatment with V4N2 at the dose of 30 nM produces a statistically significant response greater than negative control at all times studied and higher than treatment with KLH-GNE at time 21.

Figure 48:
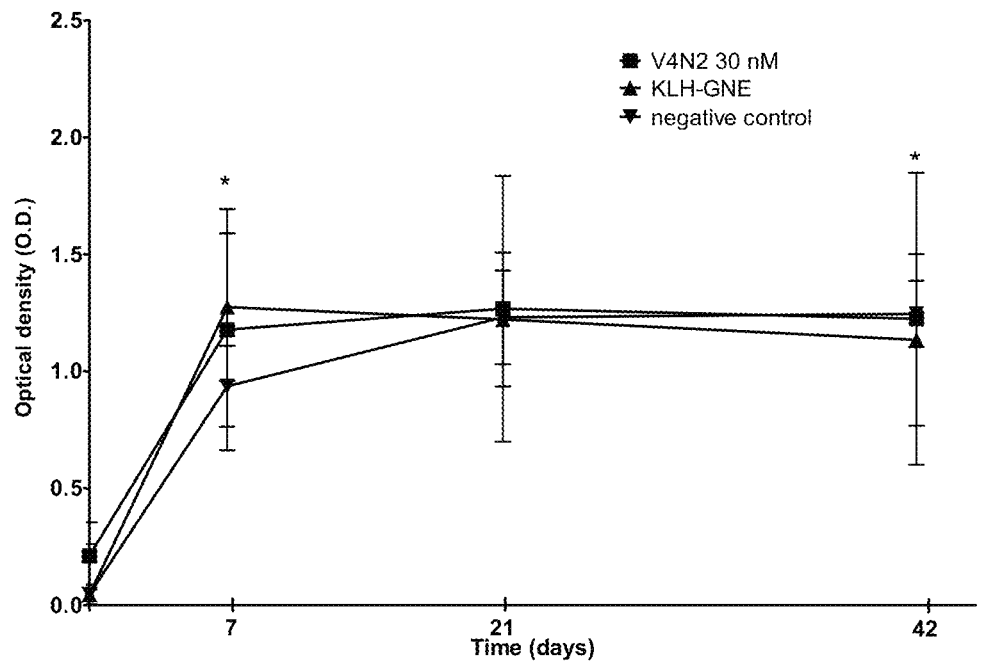
FIG. 48 presents the production of IgM-type anti-cocaine antibodies, measured by ELISA, of the negative and positive control groups and of substance V4N2 at a dose of 30 nM. The anticocaine IgM concentration is significantly lower than the negative control group in the seventh and 42's days after the first vaccination for the positive control groups and V4N2. *$p \leq 0.01$ V4N2 versus negative control; ANOVA, Bonferroni test.

It is observed in FIG. 48 that treatment with V4N2 at the dose of 30 nM is the one that induces the production of anti-cocaine IgM in titles higher than the negative control group], and that this response is statistically significant only on the $7^{th}$ and $42^{nd}$ days.

Figure 49:
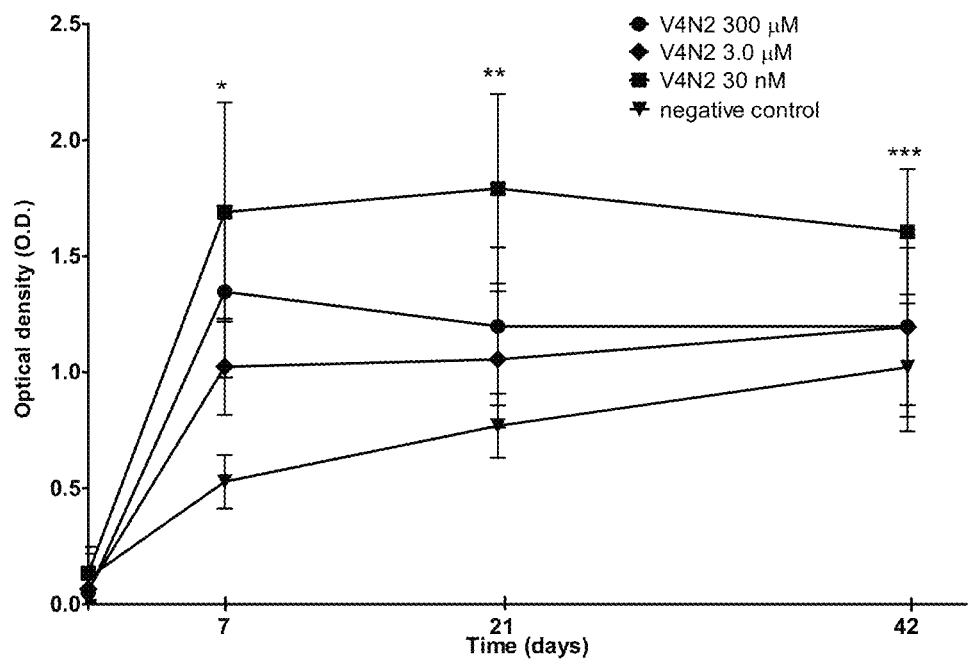
FIG. 49 presents the production of IgG-type anti-cocaine antibodies, measured by ELISA, of the negative control group and different doses of substance V4N2. The IgG anticocaine concentration is significantly higher than the negative control group on the seventh day for all doses. *$p \leq 0.001$ between V4N2 all doses versus negative control; **$p \leq 0.01$ between V4N2 300-Me 30 nM versus negative control; $p \leq 0.001$ V4N2 30 nM versus negative control. ANOVA, Bonferroni test.

It is observed in FIG. 49 that, on the seventh day, all three doses produced a significantly higher immune response than that of the negative control group. This response remains for the dose of 30 nM at all times and is no longer significant for the 3.0 µM dose at the 21-day time and for the 300 µM dose at the 42-day time.

Figure 50:
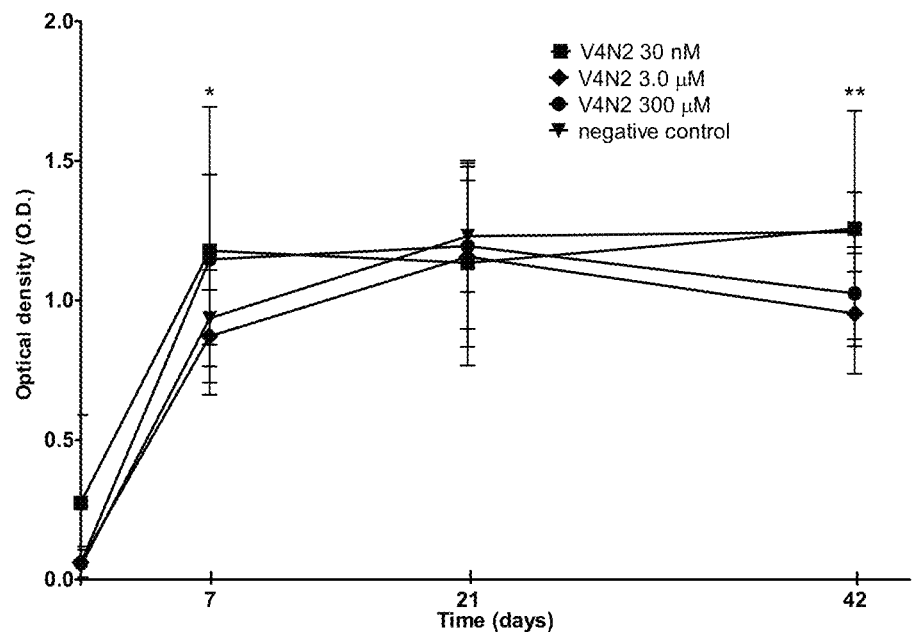
FIG. 50 presents the production of IgM-type anti-cocaine antibodies, measured by ELISA, of the negative control groups and different doses of molecule V4N2. The concentration of IgM anticocaine is significantly higher than the negative control group on the seventh day for the dose 30 nM, on the forty-second day for doses 3.0 µM and 30 nM. *p50.001, V4N2 30 nM versus negative control; **$p \leq 0.05$, V4N2 3.0 µM and 30 nM versus negative control; ANOVA, Bonferroni test.

It is observed in FIG. 50 that the production of anti-cocaine IgM antibodies was higher for the 30 nM dose on days seven and forty-two.

Figure 51:
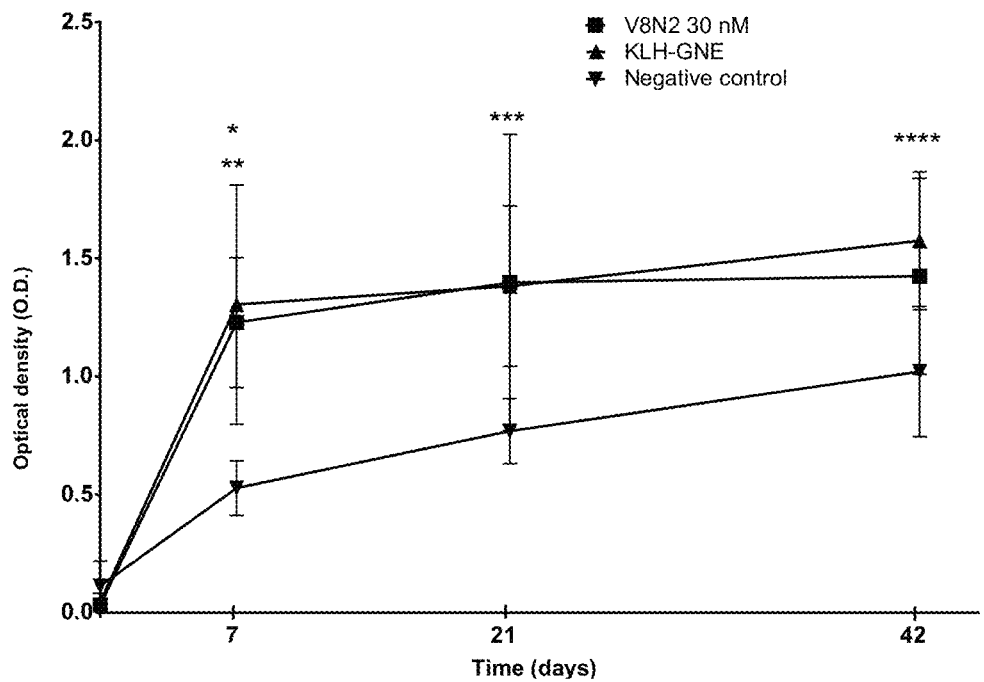
FIG. 51 presents the production of IgG-type anti-cocaine antibodies, measured by ELISA, of the negative and positive control groups and of molecule V8N2 at a dose of 30 nM. The anticocaine IgG concentration is significantly higher than the negative control group from the seventh to the forty-second day of the onset of vaccination.*$p \leq 0.001$ V8N2 versus negative control; $p \leq 0.01$ V8N2 versus KLH+GNE; * $p \geq 0.005$ negative control versus V8N2 and KLH+GNE; $p \geq 0.001$ negative control versus KLH+GNE and $p=0.01$ negative control versus V8N2, ANOVA, Bonferroni test.

It is observed in FIG. 51 that treatment with V8N2 at the dose of 30 nM produces a statistically significant response greater than negative control at all times studied and higher than treatment with KLH-GNE at time 21.

Figure 52:
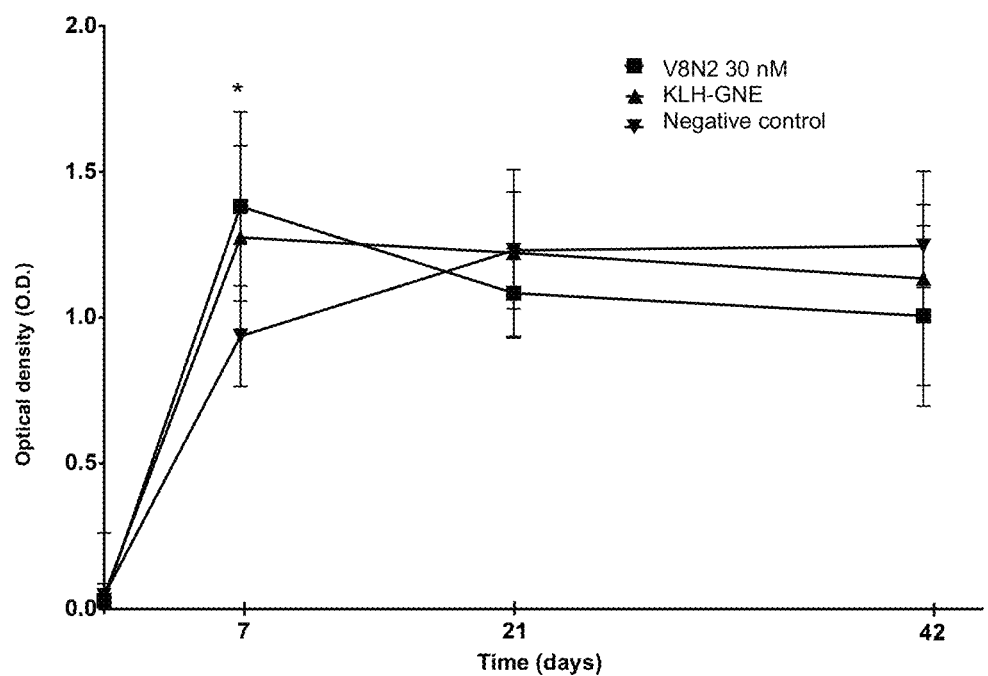
FIG. 52 presents the production of IgM-type anti-cocaine antibodies, measured by ELISA, of the negative and positive control groups and of molecule V8N2. The anticocaine IgM concentration is significantly lower than the negative control group on the seventh day after the first immunization. *$p \leq 0.001$ negative control versus V8N2; ANOVA, Bonferroni test.

It is observed in FIG. 52 that the dose of 30 nM of V8N2 is the one that induces the production of anti-cocaine IgM in titles higher than the negative control group], and that this response is statistically significant only at the 7-day time.

Figure 53:
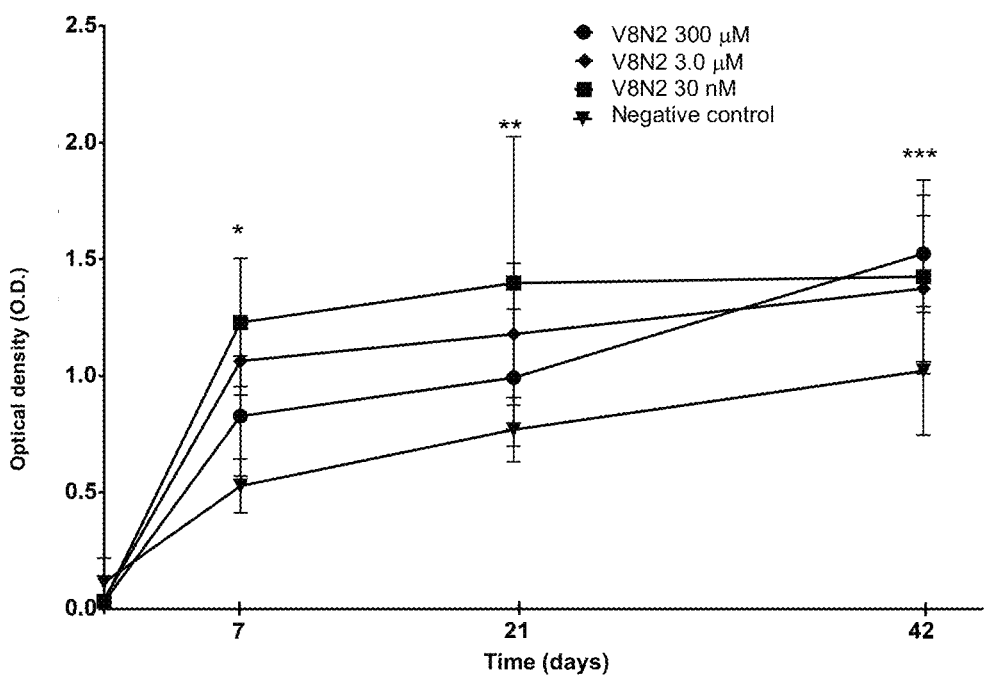
FIG. 53 presents the production of IgG-type anti-cocaine antibodies measured by ELISA, of negative control groups and different doses of molecule V8N2 (300 µM; 3.0 µM; 30 nM). The IgG anticocaine concentration is significantly higher than the negative control group on the seventh day for all doses. *$p \leq 0.001$ negative control versus V8N2, all doses; $p \leq 0.02$ negative control versus V8N2 30 nM and $p=0.047$, negative control versus V8N2 3.0 µM; *$p=0.02$ negative control versus V8N2 30 nM; $p=0.042$ negative control versus V8N2 3.0 µM and $p=0.002$ Negative control versus V8N2 300 µM. ANOVA, Bonferroni test.

It is observed in FIG. 53 that, on the seventh day, all three doses of the molecule V8N2 produced IgG at a concentration significantly higher than that of the negative control group. This response remains for the dose of 30 nM and 3.0 µM at 7, 21 and 42-day times, and for the 300 µM dose, the difference is significant on days 7 and 42.

Figure 54:
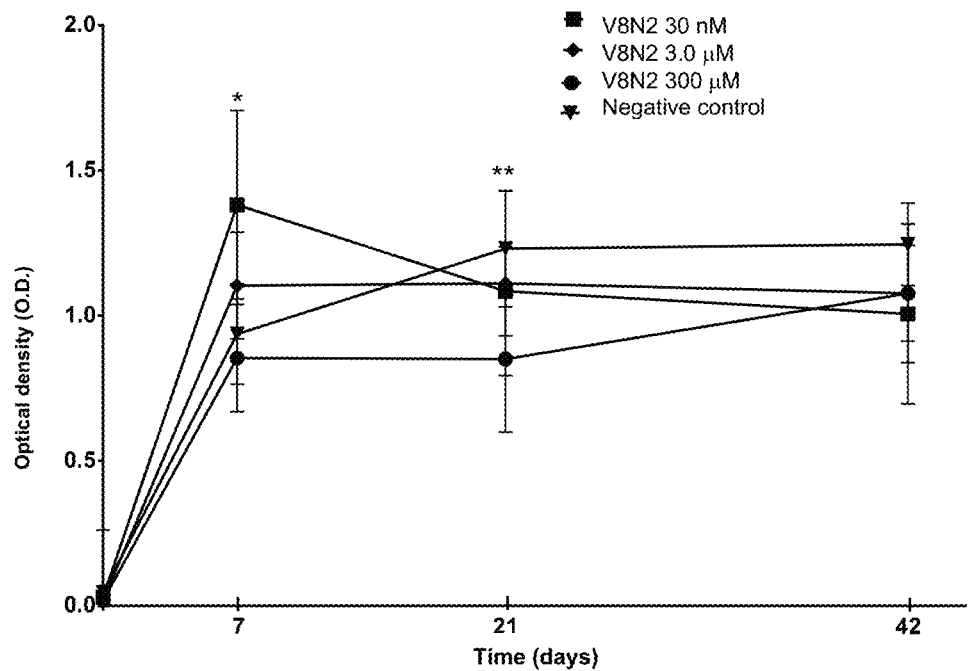
FIG. 54 presents the production of IgM-type anti-cocaine antibodies measured by ELISA, of negative control groups and different doses of substance V8N2 (300 µM; 3.0 µM; 30 nM). *$p \geq 0.001$ negative control versus V8N2 30 nM; **$p=0.002$ negative control versus V8N2 300 µM; ANOVA, Bonferroni test.

It is observed in FIG. 54 that the production of anti-cocaine IgM was significantly higher for the 30 nM dose on day seven and for the dose 300 µM on day 21.

To evaluate whether the response obtained in ELISA is due to the binding of cocaine to the antibody and if this response is dose-dependent, an experiment to analyze the antibody adsorption to cocaine was performed. For this, plasmas of the five mice that achieved the highest titers of anti-cocaine antibodies at 42-day time were mixed. 10 microliters of plasma were incubated in 2,000 microliters of sample buffer with cocaine at $10^{-2}$ to $10^{-9}$ mg $mL^{-1}$ doses for 4 hours at 37° C. After incubation, ELISA was performed, as described above.

Figure 55:
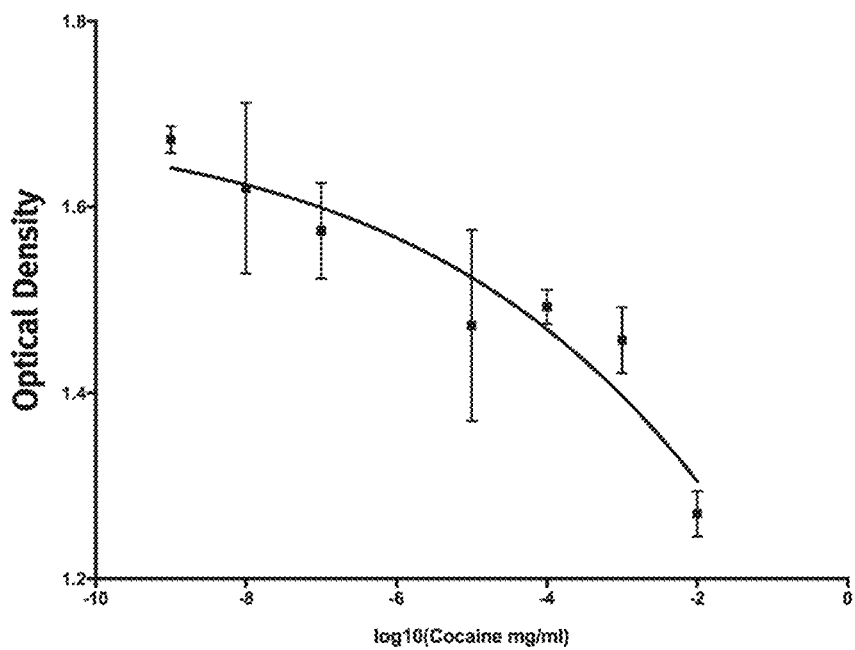
FIG. 55 presents the plasma adsorption assay of animals immunized with cocaine at doses of $10^{-2}$ to $10^{-9}$ mg mL$^{-1}$ of cocaine.
Figure 56:
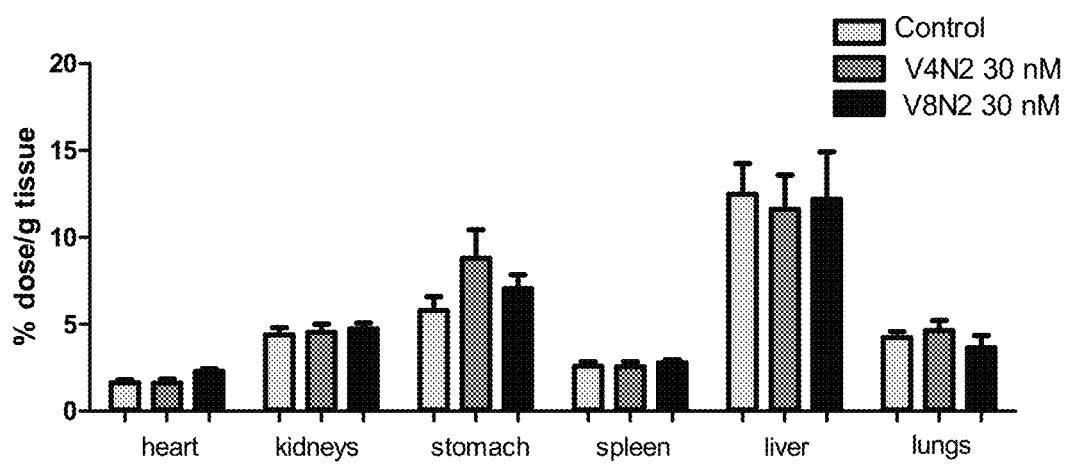
FIG. 56 presents the ex vivo biodistribution studies of the radiotracer, 90 minutes after intravenous administration of [$^{99m}$Tc]-TRODAT-1 in animals previously immunized with V4N2 and V8N2 (n=7). The results were expressed as mean±standard error and analyzed by the one-way ANOVA Test and Newman-Keuls Multiple Comparison Test.
Figure 57:
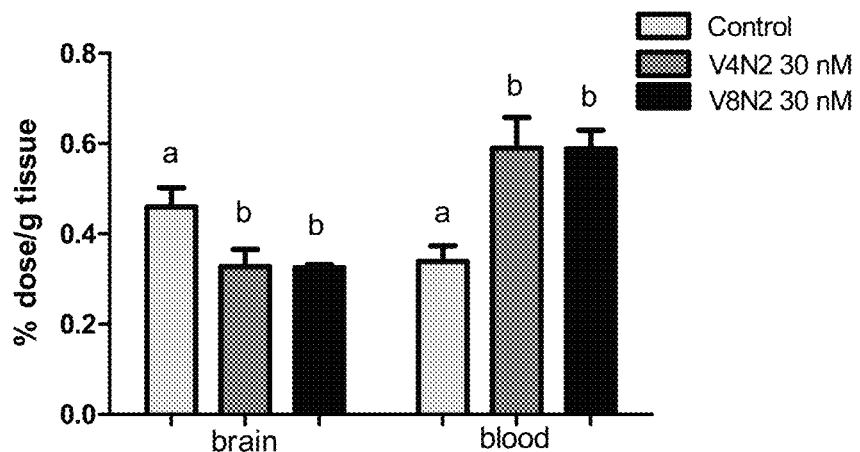
FIG. 57 presents the ex vivo biodistribution of the radiotracer, 90 minutes after intravenous administration of [$^{99m}$Tc]-TRODAT-1 in the brain and blood of animals previously immunized with V4N2 and V8N2 (n=7). The results were expressed as mean±standard error and analyzed by the one-way ANOVA Test and Newman-Keuls Multiple Comparison Test.
Figure 58:
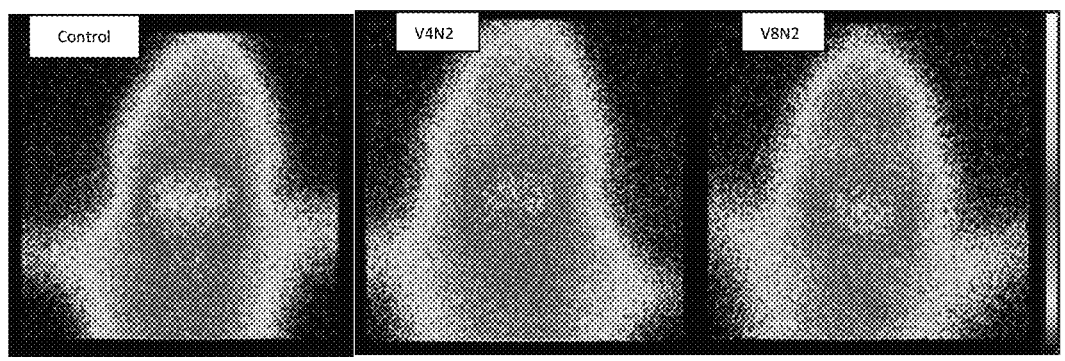
FIG. 58 presents the scintigraphic images of the animals' brains of the control, V4N2 and V8N2 groups. The color scale represents radioactivity levels, with the blue color being the lowest radioactivity capture of the background order. On the other hand, the highest level of radioactivity is represented on the scale by pale pink color.

According to data from FIG. 55, adsorption with cocaine at progressive doses produces a response dose curve, with a decline in antibody titration according to the increased dose of incubated cocaine.

Example 4—Experiments with the TRODAT-1 Marker

To perform biodistribution studies, a cocaine analogue was used, named TRODAT-1, a product available on the market in the form of a diagnostic kit for use in Nuclear Medicine. Therefore, TRODAT-1 has a mechanism of action very similar to cocaine, that is, a great affinity for dopamine (ADHD), presenting high selectivity and specificity for these carriers in the brain. In this sense, in the bloodstream, the radiotracer [$^{99m}$Tc]-TRODAT-1 would behave similarly to cocaine by binding to antibodies present in animal blood that were previously immunized with V4N2 and V8N2 substances. Thus, it is expected that the complex [$^{99m}$Tc]-TRODAT-1-antibodies is less distributed in brain tissue.

The TRODAT-1 reagent was marked with the radioactive technetium-99m isotope, which is a gamma radiation emitter, at 140 keV energy, and has a 6.02-hour physical half-life, presenting ideal features for generating scintigraphic images.

The marking was made in accordance with the instructions for use of the product TRODAT-1, of RPHPHARMA. The kit was reconstituted with 5 mL of a sterile sodium pertechnetate solution (Na$^{99m}$TcO$_4$) recently eluted from the molybdenum-99/technetium-99m generator ($^{99}$Mo/$^{99m}$Tc; IPEN/CNEN), with an activity of 1,628 MBq (44 mCi). Then, the solution was incubated for 30 minutes in a water bath at 100° C.

To determine the radioactive purity (PR) the instructions for the use of product TRODAT-1 of RPHPHARMA were used. Whatman 3 MM paper plates (PLATE 1) and silica gel 60 (PLATE 2) were used. Radiopharmaceutical aliquots (3 μL) of $^{99m}$Tc-TRODAT-1 were applied in each of the plates. The Whatman 3 MM paper plate was placed in a chromatographic pot containing butanone PA. With this method, the percentage of radioactivity related to hydrolyzed and reduced technetium ($^{99m}$TcO$_2$) was determined. The silica gel 60 plate was placed in a chromatographic pot containing 0.9% sodium chloride solution. With this method, the percentage of radioactivity related to pertechnetate ($^{99m}$TcO$_4^-$) was determined. The PR should be ≥90%. Chromatography radioactivity was counted using a curiometer (Capintec CRC 15R, USA). PR was determined as follows:

$$\text{Plate 1: } \%\ ^{99m}\text{TcO}_2 = \frac{\text{activity of fraction } 2 \times 100}{\text{activities of fractions } 1+2}$$

$$\text{Plate 2: } \%\ ^{99m}\text{TcO}_4{}^- = \frac{\text{activity of fraction } 1 \times 100}{\text{activities of fractions } 1+2}$$

After labeling, BALB/c male mice, previously immunized with v4N2 and V8N2 substances at a concentration of 30 nM, were anesthetized with a mixture of ketamine (80 mg kg$^{-1}$) and xylazine (15 mg kg$^{-1}$) and then 0.1 mL (3.7 MBq) of $^{99m}$Tc-TRODAT-1 was injected into the animal tail vein (n=7). After 90 min of injection, the animals were again anesthetized and placed in dorsal decubitus in a gamma-chamber (Mediso, Hungary) equipped with a single hole collimator. The images were obtained using an array size of 512×512×16 pixels over a period of 10 min.

After obtaining the scintigraphic images, the animals were submitted to euthanasia and blood and organ samples from the liver, spleen, stomach, kidneys, lungs and brain were removed, weighed and radioactivity was determined using the Wizard well counter (Turku, Finland). Dose patterns were used to correct the $^{99m}$Ct physical decay and to calculate the dose percentage injected per gram of tissue (% DI/g), according to the formula represented below.

$$\%\ DI/\text{g} = \frac{{}^{*}cpm/\text{g (tissue)}}{cpm \text{ of the dose pattern}} \times 100$$

$^{*}cpm$ = counts per minute

The radiochemical purity of TRODAT-1 radiolabelled with technetium-99m was of the order of 933, meaning that 931 of the technetium-99m atoms were linked to the TRODAT-1 molecules. Therefore, the result was compatible with investigations using scintigraphic images and with biodistribution studies.

There were no statistically significant differences observed in the analysis of FIG. 56 between the organs heart, kidneys, stomach, spleen, liver and lungs of each group investigated (p≥0.05).

The analysis of FIG. 57 allowed us to infer that the brains of animals immunized with substances V4N2 and V8N2 presented lower $^{99m}$Tc-TRODAT-1 in relation to control (p≤0.05). Higher radiotracer uptake was observed in the blood of immunized animals when compared to the animals of the control group (p≤0.05).

The ex vivo biodistribution results suggest that antibodies produced and induced in the administration of V4N2 and V8N2 were bonded to [$^{99m}$Tc]-TRODAT-1 reducing the uptake around 37.0% of this radiotracer in the brain, contributing to increase significantly, that is in the same proportion (44.0%), the concentration of radiotracer in the blood.

A higher radioactivity uptake in the delimited area is observed qualitatively in the scintigraphic images, that is, of [$^{99m}$Tc]-TRODAT-1 represented by the light pink color in the animal's brain of the control group, when compared to the images of animals previously immunized with V4N2 and V8N2 (FIG. 58).

The scintigraphic images (FIG. 58) corroborate the data obtained in the biodistribution studies ex vivo, shown in FIGS. 55 and 56. These results indicate that there was a protection mediated by antibodies produced by active immunization with substances V4N2 and V8N2 regarding the capture of the cocaine analogue [$^{99m}$Tc]-TRODAT-1 by brain tissue.

What is claimed is:

1. An immune system stimulating molecule comprising a calixarene, wherein the calixarene is calix(4)arene or calix(8)arene, coupled to a hapten analogous to cocaine, the hapten being hapten GNE (6-(1R,2R,3S,5S)-3-(benzoyloxy)-8-methyl-8-azabicyclo[3.2.1]octane-2-carboxamido-hexanoic acid) or hapten GNC (6-(((1R,2R,3S,5S)-3-(benzoyloxy)-8-methyl-8-azabicyclo[3.2.1]octane-2-carbonyl)oxy)-hexanoic acid).

2. A process for synthesizing the immune system stimulating molecule according to claim 1, characterized by producing calix(4)arene coupled to the hapten GNC or hapten GNE, named V4N1 and V4N2, respectively, comprising the following steps:

a) obtaining substance 4OH (5,11,17,23-tetra-tert-butyl-25,26,27,28-tetrahydroxicalix(4)arene) by cyclocondensation reaction of p-tert-butylphenol with formaldehyde;

b) obtaining substance 4TA (5,11,17,23-tetra-tert-butyl-25,26,27,28-tetrabutoxicalix(4)arene) by O-alkylation of substance 4OH obtained in "a";

c) obtaining substance 4NO (5,11,17,23-tetranitro-25,26, 27,28-tetrabutoxicalix(4)arene) by ipso-nitration of substance 4TA obtained in step "b";

d) obtaining substance 4NH (5,11,17,23-tetramino-25,26, 27,28-tetrabutoxicalix(4)arene) by reducing substance 4NO obtained in step "c";

e) obtaining immunogens V4N1 and V4N2 by the coupling reaction between substance 4NH obtained in step "d" and hapten GNC or GNE, respectively.

3. A process for synthesizing immune system stimulating molecules, characterized by producing calix(8)arene coupled to hapten GNC (6-(((1R,2R,3S,5S)-3-(benzoyloxy)-8-methyl-8-azabicyclo[3.2.1]octane-2-carbonyl)oxy)-hexanoic acid) or GNE (6-((1R,2R,3S,5S)-3-(benzoyloxy)-8-methyl-8-azabicyclo[3.2.1]octane-2-carboxamido-hexanoic acid), named V8N1 or V8N2, respectively, comprising the following steps:

a) obtaining substance 8OH (5,11,17,23,29,35,41,47-octa-tert-butyl-49,50,51,52,53,54,55,56-octahydroxicalix(8)arene), by cyclocondensation reaction of p-tert-butylphenol with paraformaldehyde;

b) obtaining substance 8TA (5,11,17,23,29,35,41,47-octa-tert-butyl-49,50,51,52,53,54,55,56-octabutoxicalix(8)arene), by O-alkylation of the substance 8OH obtained in "a";

c) obtaining substance 8NO 5,11,17,23,29,35,41,47-octanitro-49,50,51,52,53,54,55,56-octabutoxicalix(8)arene), by ipso-nitration of the substance 8TA obtained in step "b";

d) obtaining substance 8NH (5,11,17,23,29,35,41,47-octaamino-49,50,51,52,53,54,55,56-octabutoxicalix(8)arene), by reduction of the substance 8NO obtained in step "c";

e) obtaining immunogens V8N1 and V8N2 by the coupling reaction between substance 8NH obtained in step "d" and hapten GNC or GNE, respectively.

4. An anti-drug vaccine comprising at least one of the immune system stimulating molecules according to claim 1 and pharmaceutically and pharmacologically acceptable excipients.

5. A method for treating patients addicted to drugs of abuse, comprising administering the anti-drug vaccine according to claim 4 to a patient in need thereof.

6. A method for preventing fetal exposure to drugs in a pregnant woman who used drugs of abuse comprising administering the anti-drug vaccine according to claim 4, to said pregnant woman.

7. The method according to claim 5, wherein said patients are addicted to cocaine.

8. The method according to claim 6, wherein said pregnant woman uses cocaine.

\* \* \* \* \*